United States Patent [19]
Kambara et al.

[11] Patent Number: 5,985,556
[45] Date of Patent: Nov. 16, 1999

[54] DNA SEQUENCING METHOD AND DNA SAMPLE PREPARATION METHOD

[75] Inventors: Hideki Kambara, Hachioji; Kazunori Okano, Shiki, both of Japan

[73] Assignee: Hitachi, Ltd., Tokyo, Japan

[21] Appl. No.: 08/715,461

[22] Filed: Sep. 18, 1996

[30] Foreign Application Priority Data

Sep. 18, 1995 [JP] Japan .................................. 7-238141
Jan. 30, 1996 [JP] Japan .................................. 8-013634

[51] Int. Cl.⁶ .............................. C12Q 1/68; C12P 19/34; C07H 21/04
[52] U.S. Cl. .......................... 435/6; 435/91.1; 435/91.2; 536/24.3; 536/24.33
[58] Field of Search ................................ 435/91.1, 91.2, 435/6, 810; 536/24.3, 24.33

[56] References Cited

U.S. PATENT DOCUMENTS

| | | | |
|---|---|---|---|
| 5,650,274 | 7/1997 | Kambara et al. | 435/6 |
| 5,817,464 | 10/1998 | Kambara et al. | 435/6 |
| 5,824,481 | 10/1998 | Kambara et al. | 435/6 |
| 5,861,252 | 1/1999 | Kambara et al. | 435/6 |

OTHER PUBLICATIONS

Okano et al., Gene 176, 231–235 (1996).
Surikagaku, No. 359, May (1993), pp. 74–81.
Sambrook et al, Molecular Cloning, 2nd Ed. Cold Spring Harbor Laboratory Press (1989), pp. 13–21 –13–23.
Kieleczawa et al Science, 258 (1992), pp. 1787–1791.
Studier, Proc. Natl. Acad. Sci. U.S.A., 86, 6917–6921 (1989).
Furuyama et al. DNA Research, 1, 231–237 (1994).

*Primary Examiner*—Kenneth R. Horlick
*Attorney, Agent, or Firm*—Antonelli, Terry, Stout & Kraus, LLP

[57] ABSTRACT

A kit and a method of DNA sequencing including digesting a sample DNA with a restriction enzyme to obtain a DNA fragment; introducing an oligonucleotide having a definite base sequence into the DNA fragment at the 3' terminus; and performing a complementary strand extension reaction, using a labeled primer. The complementary strand extension reaction uses as a template, a single strand of the DNA fragment having the oligonucleotide introduced thereinto, to obtain a labeled extended primer having a base sequence complementary to the single strand of the DNA fragment. Next a sequencing reaction with the labeled primer and using the single strand of the DNA fragment having the oligonucleotide introduced thereinto, is performed with the extended labeled primer, using as a template, a part of the single strand of the sample DNA having the base sequence of the single strand of the DNA fragment and a contiguous sequence adjacent thereto, or a single strand of the sample DNA. Finally the products of the sequencing reaction are electrophoresed to determine the base sequence of the DNA fragment and at least a part of the base sequence of the sample DNA adjacent to the base sequence of the DNA fragment.

69 Claims, 18 Drawing Sheets fragment length (base)

set of anchor primers ① set of primers ②

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
           (A) LENGTH: 18 base pairs
           (B) TYPE: nucleic acid
           (C) STRANDEDNESS: single
           (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:1:

TGTAAAACGA CGGCCAGT                                                         18

(2) INFORMATION FOR SEQ ID NO:2:

(i) SEQUENCE CHARACTERISTICS:
           (A) LENGTH: 22 base pairs
           (B) TYPE: nucleic acid
           (C) STRANDEDNESS: single
           (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:2:

GTAATACGAC TCACTATAGG GC                                                    22

(2) INFORMATION FOR SEQ ID NO:3:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:3:

TTTTTTTTTT TTTTGCAGGC                                                       20

(2) INFORMATION FOR SEQ ID NO:4:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:4:

TTTTTTTTTT TTTTGCAGGT                                                       20

(2) INFORMATION FOR SEQ ID NO:5:

(i) SEQUENCE CHARACTERISTICS:
           (A) LENGTH: 20 base pairs
           (B) TYPE: nucleic acid (C) STRANDEDNESS: single
           (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:5:

TTTTTTTTTT TTTTTCGCNN                                          20

(2) INFORMATION FOR SEQ ID NO:6:

(i) SEQUENCE CHARACTERISTICS:
           (A) LENGTH: 26 base pairs
           (B) TYPE: nucleic acid
           (C) STRANDEDNESS: single
           (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:6:

GTAAAACGAC GGCCAGTGGA TGCATG                                   26

(2) INFORMATION FOR SEQ ID NO:7:

(i) SEQUENCE CHARACTERISTICS:
           (A) LENGTH: 22 base pairs
           (B) TYPE: nucleic acid
           (C) STRANDEDNESS: single
           (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:7:

CATCCACTGG CCGTCGTTTT AC                                       22

(2) INFORMATION FOR SEQ ID NO:8:

(i) SEQUENCE CHARACTERISTICS:
           (A) LENGTH: 11 base pairs
           (B) TYPE: nucleic acid
           (C) STRANDEDNESS: single
           (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:8:

GGATGCATGN N                                                   11

(2) INFORMATION FOR SEQ ID NO:9:

(i) SEQUENCE CHARACTERISTICS:
           (A) LENGTH: 11 base pairs
           (B) TYPE: nucleic acid
           (C) STRANDEDNESS: single
           (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:9:

GTATGCATGN N　　　　　　　　　　　　　　　　　　　　　　　　　　　　　　11

DNA SEQUENCING METHOD AND DNA SAMPLE PREPARATION METHOD

BACKGROUND OF THE INVENTION

1. Field of the Invention

The present invention relates to a method for DNA analysis based on a complementary extension reaction using a DNA polymerase, and a method for preparation of a DNA sample which can be efficiently used for the DNA sequencing method, as well as a reagent kit for use in therein.

2. Description of the Related Art

With the progress of the human genome projects, a high throughput and highly efficient DNA sequencing technology is required. Conventional DNA sequencing methods involve labeling DNA fragments with a radioisotope and manually determining the size of DNA fragments by gel electrophoresis. In place of such manual DNA sequencing methods, there have been widely employed automated devices (fluorescent DNA sequencers) for an optical detection of DNA fragments through exposure to light during gel electrophoresis using fluorescent labeling of DNA. These devices are used for a DNA sequencing method which comprises hybridizing oligonucleotides called primers, with a target DNA to be sequenced. Then, DNA fragments are prepared having various lengths for use in the DNA sequencing method by a complementary strand extension reaction using a DNA polymerase. Finally, the size of DNA fragments is determined by gel electrophoresis. This DNA sequencing is called the Sanger sequencing method or dideoxy sequencing method. In this method, the size of DNA sequenced in a single operation depends on the separation activity on a gel, however, the DNA sequence base length is in the range of 400 to 700. Sequencing of DNAs over several Kbp is labor intensive and time consuming work.

For sequencing of long DNAs over several Kbp, a shotgun strategy has been employed heretofore. According to the shotgun strategy, a sample DNA is randomly digested by means of ultrasonic vibration, the resulting DNA fragments are cloned into E. coli and cultivated to make colonies. Then, E. coli in each colony is cultivated to increase the copy number of the DNA. Thereafter, the sample DNA is extracted and provided for analysis. In the shotgun method, DNAs in each colony contain DNA fragments of the sample DNA. The portion of the sample DNA which corresponds to the DNA fragments is unidentified until sequencing is completed. Therefore, DNA fragments corresponding to DNA fragment lengths 10 to 20 times longer than the target length, should be analyzed. For this reason, much time and labor is required causing a serious obstacle.

DNA sequencing starts with the preparation of a DNA library which covers all DNAs, and making clones having a length of 10 Kbp to 100 Kbp from the DNAs present in the genome. In the actual sequencing, each clone is further digested to make subclones having a size sufficient to permit analysis with a DNA sequencer. The subclones are then sequenced again. Finally, the DNA fragments sequenced are reconstituted to obtain the intact overall DNA sequence. The method described above is now widespread because of its simplicity.

As is currently observed in the human genome projects, however, the shotgun strategy is not necessarily the best approach for large scale DNA sequencing in view of throughput and automation (SURI KAGAKU, No. 359, May, (1993) pp. 74–81). This is because it is complicated and troublesome to prepare subclones prior to measurements with DNA sequencers. Heretofore, subclones have been prepared by randomly digesting huge DNAs by sonication (Molecular Cloning, second edition, Cold Spring Harbor Laboratory Press (1989), pp. 13.21–13.23). The subclones are cloned into E. coli which is cultivated and the colonies obtained having the desired DNA fragments, were selected. Then, using plasmids carrying the selected DNA fragments, DNA sequencing is performed for every colony. The base length of DNA which can be determined by single DNA sequencing ranges generally from 300 to 500 bases. It is required that a number of subclones be analyzed.

Even though colonies are used, there are many colonies containing the same DNA fragment portion so that overlapping portions of the DNA sequence must be sequenced. For this reason, it is necessary to analyze a base length 10 to 20 times longer than the length of DNA to be actually sequenced. For example, more than 400 plasmids (subclones) should be analyzed to sequence a DNA having a length of 10 Kbp, however, it is impossible to select subclones in such a manner that sequencing information does not overlap with each other. In addition, subclones are prepared utilizing the E. coli host-vector system and hence, operations are complicated and not suitable for automation.

The primer walking method (Science, 258 (1992), pp. 1787–1791; Proc. Natl. Acad. Sci. U.S.A., 86, 6917–6921 (1989)) does not include overlapping sequences of the same base sequence. According to the primer walking method, a huge DNA is employed as a sample DNA, in its intact form. First, a part of the sample DNA is used to determine its base sequence. Next, based on the thus determined DNA sequence, a primer capable of specifically hybridizing with the portion for which the sequence has been determined, is synthesized to determine the DNA sequence of a contiguous portion. That is, in the primer walking method, the base sequence of a DNA fragment to be sequenced is sequentially determined one by one from the terminus thereof. However, the primer walking method requires that primers be synthesized for every sequencing, even though overlapping portions for DNA sequencing are minimized. In addition, the sequencing operations of the primer walking method are sequential so that the method is not always suitable for large scale sequencing.

In order to solve the problems of complicated operations associated with cloning or primer walking, various attempts have been made. In particular, direct sequencing of DNA fragments in mixture form obtained from a sample DNA digested with a restriction enzyme (DNA Research, 1 (1994) pp 231–237) is a promising method, which is briefly explained below. A known sequence oligonucleotide is ligated to a DNA fragment at the terminus thereof, to produce the priming site of each DNA digested with a restriction enzyme. Then sequencing is conducted using a set of primers which can discriminate a restriction cutter recognition sequence from the sequence adjacent to the cutting site (1 to 4 bases). The primer set includes, for example, 16 combinations of all DNA sequences in the case of an unknown base sequence having variable two base sequence at the 3' terminus. In the case of approximately three types of double stranded DNA fragments (6 types in terms of DNA terminus), the base sequence of each DNA fragment can be determined directly from the mixture, using the set of primers described above. After the base sequence of each DNA fragment has been determined, the base sequences of the respective DNA fragments are reconstructed to obtain the overall base sequence. In order to obtain the overall base sequence, a primer having the same base sequence as that of each DNA fragment around the 3' terminus is synthesized, and intact DNA is used as a template for sequencing so that the base sequence between one DNA fragment and another DNA fragment is determined. This determines how the respective DNA fragments are ligated with each other. Alternatively, the base sequence of a DNA fragment digested with another restriction enzyme is determined. With overlapping base sequences as guides, the relationship of one fragment to another is determined.

SUMMARY OF THE INVENTION

As described hereinabove, sequencing of a long DNA has been made heretofore using labor intensive and time consuming processes. The method which uses subclones has been widely employed, since a plurality of DNA fragments (subclones) can be sequenced at the same time using this method. However, the following problems are encountered with this method. Overlapping base sequence parts are read again and again and hence, much labor and time are required as the scale of sequencing increases. On the other hand, when overlapping portions are reduced to improve efficiency, it becomes difficult to link the sequenced DNA fragments with each other and the base sequence of intact long DNA cannot be reconstituted.

The primer walking method is advantageous in that it is clear how to link or joint the sequenced portions, because a next primer is always synthesized from the portion adjacent to the sequenced portion and employed for the next sequencing. However, the primer walking method has problems which limit the operability since a single DNA strand should be sequenced sequentially one by one from one terminus by every portion of several hundred bases. In addition, a primer synthesized based on the sequenced portion does not function satisfactorily which causes difficulty in overall sequencing. The method for DNA sequencing of DNA fragments using restriction enzymes is also disadvantageous in that the reconstitution of DNA fragments is labor intensive.

In order to solve the foregoing problems, a first object of the present invention is to provide a method for the DNA sequencing of a sample DNA characterized by simultaneously determining the base sequence of an objective DNA fragment and at least a part of the contiguous base sequence of the sample DNA adjacent to the objective DNA fragment.

To achieve the first object, the present invention comprises the following steps.

According to DNA sequencing (A) as a first aspect of the present invention, the sequencing method (A) is characterized by comprising:

(A1) a step of digesting a sample DNA with a restriction enzyme to obtain DNA fragments;

(A2) a step of introducing an oligonucleotide having a predetermined base sequence (e.g., an oligonucleotide of single base species) into the DNA fragments at the 3' end thereof;

(A3) a step of performing a complementary strand extension reaction, using a labeled primer (e.g. fluorophore tagged primer) which comprises a first base sequence portion complementary to at least a part of the base sequence of the oligonucleotide, a second base sequence portion complementary to the base sequence recognized by the restriction enzyme and a third base sequence of a possible combination of 1 to 4 bases, by using, as a template, a single strand of the DNA fragment having the oligonucleotide introduced thereinto to obtain a labeled extended primer having a base sequence complementary to the single strand of the DNA fragment;

(A4) a step of proceeding, independently or simultaneously, (a) a step of performing a sequencing reaction using the labeled primer by using, as a template, the single strand of the DNA fragment having the oligonucleotide introduced thereinto, and (b) a step of performing a sequencing reaction using the labeled extended primer by using, as a template, a part of the single strand of the sample DNA having the base sequence of the single strand of the DNA fragment and an adjacent sequence thereto, or the single strand of the sample DNA; and, (A5) a step of subjecting products of the sequencing reaction to electrophoresis to determine the base sequence of the DNA fragment and at least a part of the base sequence of the sample DNA adjacent to the base sequence of the DNA fragment, thereby to determine the base sequence of the sample DNA in the portion longer than the length of the DNA fragment. The sequencing method (A) is further characterized in that in steps (A3) and (A4), the steps (A3) and (A4) are repeated several times, using a thermostable DNA polymerase by varying temperature conditions, respectively, thereby to acquire a sufficient copy number of the labeled extended primers and the sequencing products.

According to DNA sequencing (B) as a second aspect of the present invention, the sequencing method (B) is characterized by comprising:

(B1) a step of digesting a sample DNA with a first restriction enzyme to obtain DNA fragments;

(B2) a step of performing extension using a primer by using a single strand of the DNA fragment as a template and then replacing the 3' end of the DNA fragment with a fluorophore tagged nucleotide;

(B3) a step of digesting the complementary strand formed in the step (B2) with a second restriction enzyme different from the first restriction enzyme to obtain a fluorophore tagged primer having a label at the 3' end thereof;

(B4) a step of performing a sequencing reaction using the fluorophore tagged primer by using, as a template, a part of the single strand of the sample DNA having the base sequence of the single strand of the DNA fragment and an adjacent sequence thereto, or the single strand of the sample DNA; and, (B5) a step of subjecting products of the sequencing reaction to electrophoresis to determine at least a part of the base sequence of the sample DNA adjacent to the base sequence of the DNA fragment thereby to determine a base sequence of the sample DNA in a portion longer than the length of the DNA fragment.

According to DNA sequencing (C) as a third aspect of the present invention, the sequencing method (C) is characterized by comprising:

(C1) a step of digesting a sample DNA with a restriction enzyme to obtain DNA fragments;

(C2) a step of performing a complementary strand synthesis reaction using a primer by using the single strand of the DNA fragment as a template to obtain a primer having a base sequence complementary to the single strand of the DNA fragment;

(C3) a step of performing a sequencing reaction using a primer by using, as a template, a part of the single strand of the sample DNA having the base sequence of the single strand of the DNA fragment and a contiguous sequence adjacent thereto, or the single strand of the sample DNA thereby to introduce a fluorophore tag at the terminus of an extended strand;

(C4) a step of digesting products of the sequencing reaction with a restriction enzyme; and, (C5) a step of subjecting the digested products of the sequencing reaction to electrophoresis to determine at least a part of the base sequence of the sample DNA adjacent to the base sequence of the DNA fragment thereby to determine the base sequence of the sample DNA in the portion longer than the length of the DNA fragment.

According to DNA sequencing (D) as a fourth aspect of the present invention, the sequencing method (D) is characterized by comprising:

(D1) a step of digesting a sample DNA with a restriction enzyme to obtain DNA fragments;

(D2) a step of performing a complementary strand synthesis reaction using a fluorophore tagged primer by using the single strand of the DNA fragment as a template to obtain a primer having a base sequence complementary to the single strand of the DNA fragment;

(D3) a step of performing a sequencing reaction using the primer by using as a template a part of the single strand of the sample DNA having the base sequence of the single strand of the DNA fragment and a contiguous sequence adjacent thereto, or the single strand of the sample DNA; and, (D4) a step of subjecting products of the sequencing reaction to electrophoresis to determine at least a part of the base sequence of the sample DNA adjacent to the base sequence of the DNA fragment thereby to determine the base sequence of the sample DNA in the portion longer than the length of the DNA fragment.

According to DNA sequencing (E) as a fifth aspect of the present invention, the sequencing method (E) is characterized by comprising:

(E1) a step of digesting a sample DNA with a restriction enzyme to obtain DNA fragments;

(E2) a step of performing a sequencing reaction using a first primer labeled with a fluorophore tag which selectively couples with the DNA fragment by the complementary strand, and a second primer labeled with a fluorophore tag which has a base sequence complementary to a single strand of the DNA fragment, by using, as a template, a mixture of a part of the single strand of the sample DNA having the base sequence of the single strand of the DNA fragment and a contiguous sequence adjacent thereto or the single strand of the sample DNA with the DNA fragment; and, (E3) a step of subjecting products of the sequencing reaction to electrophoresis to determine the base sequence of the DNA fragment and at least a part of the base sequence of the sample DNA adjacent to the base sequence of the DNA fragment, thereby to determine the base sequence of the sample DNA in the portion longer than the length of the DNA fragment.

According to DNA sequencing (F) as a sixth aspect of the present invention, the sequencing method (F) is characterized by comprising:

(F1) a step of digesting a sample DNA with a restriction enzyme to obtain DNA fragments;

(F2) a step of performing an extension reaction of a primer by using a single strand of the DNA fragment as a template to obtain a single stranded DNA of the fragment;

(F3) a step of performing a sequencing reaction using the single stranded DNA by using, as a template, a part of the single strand of the sample DNA having the base sequence of the single strand of the DNA fragment and the base sequence adjacent thereto, or the single strand of the sample DNA; and, (F4) a step of subjecting products of the sequencing reaction to electrophoresis to determine at least a part of the base sequence of the sample DNA adjacent to the base sequence of the DNA fragment, thereby to determine the base sequence of the sample DNA in the portion longer than the length of the DNA fragment.

According to DNA sequencing (G) as a seventh aspect of the present invention, the sequencing method (G) is characterized by comprising:

(G1) a step of performing a complementary strand extension reaction using a primer having at the 3' terminus a complementary base sequence to a part of the base sequence of a single strand of the DNA fragment obtained from a sample DNA to obtain an extended primer having a complementary base sequence to a part of the single strand of the DNA fragment;

(G2) a step of proceeding:
(a) a step of performing a sequencing reaction using the primer by using the single strand of the DNA fragment as a template and;
(b) a step of performing a sequencing reaction using the extended primer by using, as a template, a part of the single strand of the sample DNA having the base sequence of single strand of the DNA fragment and a contiguous sequence adjacent thereto, or the single strand of the sample DNA; and, (G3) a step of subjecting products of the sequencing reaction to electrophoresis to determine the base sequence of the DNA fragment and at least a part of the base sequence of the sample DNA adjacent to the base sequence of the DNA fragment thereby to determine the base sequence of the sample DNA in the portion longer than the length of the DNA fragment.

In the sequencing procedures above, the sample DNA is digested with a restriction enzyme to obtain DNA fragments but the present invention is not limited only thereto. DNA fragments may also be obtained by randomly cutting the sample DNA by means of sonication, etc. Any other conventional manner may be likewise employed to obtain DNA fragments from the sample DNA.

The DNA sequencing method in accordance with the present invention is characterized by linking or jointing one base sequence of a DNA fragment to another through extension (hereinafter the DNA sequencing method of the present invention is referred to as a fragment walking method), which will be described hereinbelow in detail. The DNA sequencing method of the present invention comprises:

(1) a step of digesting a sample DNA with a restriction enzyme;

(2) a step of examining the terminal base species of 1 to 4 bases which are recognized by the restriction enzyme and contiguous to the digested portion and the length of the DNA fragment to select a primer used for a sequencing reaction;

(3) a step of electrophoresing DNA fragments digested by the restriction enzyme to fractionate the DNA fragments depending upon fragment length;

(4) a step of introducing a known oligonucleotide into the DNA fragments at the 3' end thereof;

(5) a step of selecting the DNA fragments using a fluorophore tagged primer having at the 3' end thereof the base sequence of 1 to 4 bases for discriminating the DNA fragments at the 3' end thereof, and performing a complementary strand extension reaction using the selected DNA fragment as a template;

(6) a step of proceeding, independently or simultaneously, a sequencing reaction using the labeled primer by using the selected DNA fragment as a template and a sequencing reaction using the complementary strand formed in the step (5) by using as a template a part of the sample DNA having the same base sequence as that of the selected DNA fragment and a contiguous sequence thereto, or the sample DNA; and, (7) a step of analyzing the sequencing products produced in the step (6) to obtain the base sequence of the selected DNA fragment and the adjacent sequence to the selected DNA fragment to determine the order of the respective DNA fragments in the sample DNA thereby to determine the sequence of the sample DNA in the portion longer than the length of the selected DNA fragment.

According to the fragment walking method of the present invention, a lengthy DNA can be efficiently sequenced in a short period of time. In general, many DNA fragments are formed by digestion of DNA with a restriction enzyme but in the present invention, the target DNA sequence can be determined directly from the DNA fragments digested by a restriction enzyme. Further by exploring the overlapping sequence of the determined base sequence, the overall base sequence of a lengthy DNA can be determined with low redundancy without cloning or subcloning.

In the fragment walking method of the present invention, a selective sequencing reaction of DNA fragments which are obtained by digesting a sample DNA with a restriction enzyme is carried out, using a library of 16 kinds of a few primers previously prepared. A plurality of DNA fragments are sequenced in parallel. A fluorophore tagged primer is extended so as to give sequencing products. At the same time, fluorophore tagged and extended long primers complementary to the respective DNA fragments are simultaneously formed. The fluorophore tagged and extended long primers function as primers, in which an intact sample DNA is used as a template. The intact sample DNA as a template is added to each solution for the selective sequencing reaction of the DNA fragment obtained by digesting the sample DNA with a restriction enzyme, whereby the base sequence of each DNA fragment is determined and at the same time. The contiguous sequence of the sample DNA adjacent to the DNA fragment is determined by the sequencing products of the fluorophore tagged and extended long primer using the sample DNA as a template.

Both the base sequence of each DNA fragment and the contiguous sequence of the sample DNA adjacent to the DNA fragment beyond the portion digested with a restriction enzyme can be determined at the same time. Therefore, by searching the overlapping base sequences based on the thus determined base sequences, the overall base sequence of the sample DNA can be determined in such a manner that one DNA fragment walks over to another DNA fragment contiguous thereto. According to the fragment walking method, the length of a readable DNA is determined by a sequencing reaction in which an intact sample DNA is used as a template, not by the length of DNA fragment. Accordingly, the overall base sequence can be determined with extremely low redundancy.

The fragment walking method of the present invention is further explained below. According to the fragment walking method, a sample DNA to be sequenced is fully digested with a restriction enzyme such as a 4-base cutter recognition enzyme, to prepare fragments which do not overlap with each other. Where recognition base sequence parts by a restriction enzyme are removed from the resulting DNA fragments, the remaining base sequences are unknown. These DNA fragments lack particular priming sites with which a primer having a known base sequence hybridizes and becomes the starting position of a complementary strand extension reaction. Accordingly, an oligonucleotide having a known base sequence is introduced into the resulting DNA fragments at the 3' end thereof to form the priming site. It is known that in the case of forming an extended DNA strand through hybridization of a primer with a DNA fragment where the terminal two bases at the 3' end of the primer (called variable and discriminating sequence) are fully complementary to and perfectly hybridize with the DNA fragment, the reaction proceeds, but otherwise the reaction is slow or does not occur at all. Therefore, the base sequence part of two arbitrary bases (there are 16 combinations of the arbitrary base sequence part) is previously inserted into the fluorophore tagged primer at the 3' end (the extended site by a complementary strand extension reaction). By doing so, a specific fragment having a sequence fully complementary to the fluorophore tagged primer can be selected from the DNA fragments for complementary strand extension reaction or for determination of the base sequence (DNA Research, 1, 231–237 (1994)).

Where there are few kinds of DNA fragments and there is one DNA fragment fully complementary to one primer, the base sequence of each fragment can be determined using the primer described above. Where one primer hybridizes with two or more DNA fragments, the foregoing procedure is performed, for example, after the DNA fragments are first fractionated based upon fragment length. As described above, according to the fragment walking method of the present invention, the overall base sequence of the DNA fragments in admixture can be determined in parallel in a simple manner, without causing any overlap, using 16 primers without the necessity for cloning. In order to clarify the relationship between the DNA fragments and determine the overall base sequence of a sample DNA, the following procedure is performed. The previously mentioned 16 fluorophore tagged primers selectively hybridize only with the DNA fragment having a priming site at the terminus thereof, but not with an intact sample DNA. However, when the primer hybridized with the DNA fragment is subjected to a complementary strand extension reaction, the extended part is complementary to the intact sample DNA and hence, hybridizes with the intact sample DNA. Therefore, where a complementary strand extension for sequencing of each DNA fragment is carried out using the primer described above, the reaction is conducted under cycle sequencing conditions which control the reaction temperature. When an intact (non-digested) sample DNA is added to the reaction solution, the contiguous sequence of the intact sample DNA adjacent to the digestion part can also be determined, in addition to the base sequence of the DNA fragment. According to this method, the base sequence of each DNA fragment and the contiguous sequence thereto can be determined simultaneously using the 16 different primers and is thus extremely efficient. This method provides for one DNA fragment walking over to another DNA fragment in order to link them with one another and is thus called the fragment walking method.

The fragment walking method is very efficient but it is necessary to prepare 16 primers which correspond to all possible combinations of the two terminal bases at the 3' end. As the DNA sequencer of fluorescence type, there is a single dye detection method (in which the terminal base species of DNA fragments are discriminated by one fluorophore and DNA fragments having different terminal base species are electrophoresed at different migration paths) and a four dye detection method (in which DNA fragments are discriminated by four fluorophores depending upon terminal base species; DNA fragments are electrophoresed at the same migration path). For a high throughput, the four dye detection method is more advantageous. However, when applying the fragment walking method to the four dye detection method, it is necessary to prepare at least 16×4=64 primers having a fluorophore tag. This is a problem to be solved with the fragment walking method before it is available for practical use.

A second object of the present invention is to provide a DNA sequencing method which can solve the foregoing problem and which can be readily performed using commercially available universal primers or a lesser number of primers, and a method for preparing a sample for use in the DNA sequencing method as well as a reagent kit for use in the DNA sequencing method.

In order to achieve the second object, the present invention comprises the following features.

According to the method of the present invention, a copy number of the DNA fragment that functions as a template is amplified by polymerase chain reaction (PCR) using selective primers having an anchor base sequence of 2 bases at the 3' end thereof (for brevity, hereinafter often referred to as anchored primers). The complementary strand at the anchored portion is introduced at the terminus of a DNA fragment. A fluorophore tagged primer is hybridized to the anchored portion to perform a sequencing reaction. It is not required that the anchored primers (16 primers in total) be labeled with fluorophores. Universal primers labeled with four fluorophores, respectively, which are conventionally used for sequencing may be used as the fluorophore tagged primers.

The 16 anchored primers are employed to hybridize with a specific DNA fragment selected from a mixture of DNA fragments, which are subjected to complementary strand extension, and used to increase the copy number of the specific DNA fragment. The copy number of only the DNA fragment in the mixture that completely hybridizes to the anchored primer is increased so that the specific DNA fragment can be substantially selected. Since the DNA fragment selected has the site with which the fluorophore tagged primer hybridizes, the DNA fragment is ready to perform a sequencing reaction. Thus, the fragment walking method can be readily carried out using universal fluorophore tagged primers having base sequences that can be primers in a conventional polymerase reaction, without increasing the requirement for different kinds of a fluorophore tagged primer. Examples of such fluorophore tagged primers include primers generally called universal primers such as a primer having SEQ ID NO. 1:

5'-TGTAAAACGACGGCCAGT-3'              SEQ ID NO: 1 which is used for M13 bacteriophage series vectors, a primer having SEQ ID NO. 2:

5'-GTAATACGACTCACTATAGGGC-3'         SEQ. ID NO: 2 which is used for T7 bacteriophage vectors, and fluorophore tagged primers having optional or arbitrary sequences. Needless to say, well-known fluorophores may also be used for fluorescent labeling.

As one aspect of the present invention, the method (a) for preparing a sample DNA comprises:

- (a1) a step of digesting a sample DNA with a restriction enzyme to form DNA fragments having a plurality of fragment lengths;
- (a2) a step of introducing an oligonucleotide having a known base sequence into the DNA fragments at least at the 3' end thereof;
- (a3) a step of performing a complementary strand extension reaction using the oligonucleotide and an anchored primer having a substantially complementary sequence to the recognition base sequence part recognized by a restriction enzyme and a discrimination sequence of 1 to 4 bases at the 3' end and having an anchor base sequence of at least 8 nucleotides (octamer) at the 5' end to obtain a DNA strand; and,
- (a4) a step of performing a complementary strand extension reaction using a primer having at least substantially the same sequence as the anchor base sequence that does not hybridize directly with the sample DNA, by using the DNA strand obtained at step (a3) as a template.

As another aspect of the present invention, the method (b) for preparing a sample DNA comprises:

- (b1) a step of digesting a sample DNA with a restriction enzyme to form DNA fragments having a plurality of fragment lengths;
- (b2) a step of introducing an oligonucleotide having a known base sequence into the DNA fragments at least at the 3' end thereof; and,
- (b3) a step of fractionating the DNA fragments depending upon their terminal base sequence and amplifying the DNA fragments by PCR, using an anchored primer having a substantially complementary sequence to the oligonucleotide, and a discrimination sequence of 1 to 4 bases at the 3' end, and having an anchor base sequence of at least 8 nucleotides (octamer) at the 5' end and a primer having substantially the same base sequence as the anchor base sequence that by itself alone does not hybridize stably with the DNA fragment and amplifying by PCR.

As a further aspect of the present invention, the method (c) for preparing a sample DNA comprises:

- (c1) a step of digesting a sample DNA with a restriction enzyme to form DNA fragments having a plurality of fragment lengths;
- (c2) a step of introducing an oligonucleotide having a known base sequence into the DNA fragments at least at the 3' end thereof;
- (c3) a step of amplifying a specific DNA fragment by PCR, using the oligonucleotide and an anchored primer having a substantially complementary sequence to the recognition base sequence part recognized by the restriction enzyme and a discrimination sequence of 1 to 4 bases at the 3' end and having an anchor base sequence of at least 8 nucleotides (octamer) at the 5' end, in which a part of the bases in the recognition base sequence part have been replaced with another base to have the base sequence part which is not digestible with the restriction enzyme, and a primer having a base sequence digestible with the restriction enzyme;
- (c4) a step of obtaining the DNA strand in which one end of the specific DNA fragment amplified has been cut out;
- (c5) a step of performing a complementary strand extension reaction using a fluorophore tagged primer at least having substantially the same sequence as the anchor base sequence that does not hybridize directly with the sample DNA, using as a template the DNA strand obtained at step (c4) to obtain the extended DNA fragment by the complementary strand extension reaction; and, (c6) a step of performing a sequencing reaction using a fluorophore tagged primer and the extended DNA fragment by the complementary strand extension reaction using as templates the DNA strand obtained at step (c4) and the sample DNA.

The method (c) is also characterized by sequencing in which the base sequence of the DNA strand and the contiguous base sequence of the sample DNA in the portion adjacent to that of the DNA strand are determined and further characterized in that the fluorophore tagged primer has, at least, substantially the same sequence as the anchor base sequence.

As a further aspect of the present invention, the method (d) for preparing a sample DNA comprises:

(d1) a step of digesting a sample DNA with a first restriction enzyme to form DNA fragments having a plurality of fragment lengths;

(d2) a step of introducing an oligonucleotide having a known base sequence and having a recognition base sequence part recognized by a second restriction enzyme into the DNA fragments at least at the 3' end thereof;

(d3) a step of amplifying a specific DNA fragment by PCR, using the oligonucleotide and a first anchor primer having a substantially complementary sequence to the recognition base sequence part recognized by the first restriction enzyme and a first discrimination sequence of 1 to 4 bases at the 3' end and having a first anchor base sequence of at least 8 nucleotides (octamer) at the 5' end, in which a part of the bases in the recognition base sequence part has been replaced with another base to have a base sequence part not digestible with the first restriction enzyme, and a second anchor primer having an oligonucleotide, a substantially complementary sequence to the recognition base sequence part recognized by the first restriction enzyme and a second discrimination sequence of 1 to 4 bases at the 3' end and having a second anchor base sequence of at least 8 nucleotides (octamer) at the 5' end, in which a part of the bases in the oligonucleotide has been replaced with another base to have the base sequence part not digestible with the second restriction enzyme;

(d4) a step of digesting the first terminus of the amplified specific DNA fragment with the second restriction enzyme and digesting the second terminus of the amplified specific DNA fragment with the first restriction enzyme to obtain the first and second DNA strands, respectively;

(d5) a step of performing a complementary strand extension reaction using a first fluorophore tagged primer at least having substantially the same sequence as the first anchor base sequence that does not hybridize directly with the sample DNA and a second fluorophore tagged primer at least having substantially the same sequence as the second anchor base sequence that does not hybridize directly with the sample DNA, by using as templates the first and second DNA strands produced at step (d4) to obtain the first and second extended DNA fragments by the complementary strand extension reaction;

(d6) a step of performing a sequencing reaction using the first and second fluorophore tagged primers and the extended first and second DNA fragments by the complementary strand extension reaction using as templates the first and second DNA strands obtained at step (d4) and the sample DNA.

The method (d) is also characterized by sequencing in which the base sequences of the first and second DNA strands and the contiguous base sequences of the sample DNA in the portion adjacent to those of the first and second DNA strands are determined, respectively, and further characterized in that the first and second fluorophore tagged primers have, at least, substantially the same sequence as the first and second anchor base sequences, respectively.

As a still further aspect of the present invention, the present invention relates to a reagent kit (e) comprising a plurality of anchored primers having a complementary base sequence to an oligonucleotide used for ligation, a recognition base sequence part recognized by a restriction enzyme and the same base sequence as that of a universal primer, having a discrimination sequence of 1 to 4 bases at the 3' end and capable of discriminating the terminal base sequence of DNA fragments, wherein the anchored primers are characterized in that the discrimination sequence for selecting the terminal two base sequence in the DNA fragments contains the base sequence of two bases in all combinations.

As a still further aspect of the present invention, the present invention relates to a reagent kit (f) comprising at least an oligonucleotide used for ligation and a primer for complementary strand synthesis, characterized in that the primer for complementary strand synthesis comprises:

a first primer set comprising 16 primers having a substantially complementary sequence to the oligonucleotide, a recognition base sequence part recognized by a restriction enzyme and a discrimination sequence of two bases at the 3' end in the recognition base sequence part, and, a second primer set comprising 16 primers introduced with an anchor base sequence into the 5' end of each primer in the first primer set, in which a part of the bases in each recognition base sequence part has been replaced with another base.

As a still further aspect of the present invention, the present invention relates to a reagent kit (g) comprising at least an oligonucleotide used for ligation and a primer for complementary strand synthesis, characterized in that the primer for complementary strand synthesis comprises:

an oligonucleotide and a first set of anchor primers having a substantially complementary sequence to the recognition base sequence part by a first restriction enzyme, a first discrimination sequence of 1 to 4 bases at the 3' end and a first anchored base sequence of at least 8 oligonucleotides (8-mer) at the 5' end, in which a part of the bases in the recognition base sequence part has been replaced with another base in order to have the base sequence part not digestible with the first restriction enzyme, and, an oligonucleotide and a second set of anchor primers having a substantially complementary sequence to the recognition base sequence part by the first restriction enzyme, a second discrimination sequence of 1 to 4 bases at the 3' end and a second anchored base sequence of at least 8 oligonucleotides (8-mer) at the 5' end, in which a part of the bases in the oligonucleotide part has been replaced with another base to make the base sequence part not digestible with the second restriction enzyme, characterized also in that the first and second discrimination sequences comprise two bases and all combinations of the two base sequences are included.

As a still further aspect of the present invention, the present invention relates to a method (h) for analysis of the sample prepared by method (a) or (b).

Referring to FIG. 1, the method of the present invention is summarized below. In order to achieve the first object of the present invention, a complementary strand extension reaction is performed using DNA fragment 3 and using as a template fluorophore tagged primer 31 to obtain extended DNA strand 32. Using the extended DNA strand as a primer and sample DNA 1 as a template, sequencing is carried out to obtain extended DNA strand 33. The extended DNA strand 33 is electrophoresed to simultaneously determine the base sequence of the DNA fragment and the base sequence of at least a part of sample DNA 1 adjacent to the DNA fragment.

According to the present invention, there may be simultaneously determined, the base sequence of the objective DNA fragment and the base sequence of a part of the DNA fragment adjacent to the objective DNA fragment at the 3' end. The method of the present invention can determine the base sequence of each DNA fragment obtained by a restriction enzyme and at the same time, can determine the base sequence of a part of the DNA fragment adjacent to each DNA fragment thereby to determine the relation between the DNA fragments in base sequences.

Therefore, in this method it is unnecessary to detect any overlap between base sequences of the respective DNA fragments using a plurality of restriction enzymes so that the base sequences can be efficiently determined. In addition, the base sequence of a lengthy sample DNA can all be determined only by reactions in vitro, without subcloning. Furthermore, each DNA fragment can be sequenced to determine the order of base sequences between DNA fragments, without synthesizing a primer for every sequencing, as required for the primer walking method. That is, the base sequence of a sample DNA can be determined without performing redundant and overlapping analysis of the respective base sequences of DNA fragments obtained from a sample DNA.

The present invention is summarized by referring to FIG. 12. In order to achieve the second object of the present invention, the present invention is carried out as follows. Sample DNA 1 is digested with NlaIII. DNA oligonucleotide 304 is added to a solution 320 containing DNA fragment groups 303 to ligate DNA oligonucleotide 304 having a known base sequence with the restriction enzyme digestion part at the 3' end thereof. The resulting solution containing the oligonucleotide ligation products is divided into 16 tubes. Different primers (having discrimination sequences for DNA fragments at the 3' end and in the anchored sequence at the 5' end) are added to the tubes prior to a complementary strand extension reaction. The products obtained are subjected to gel electrophoresis. Using the electropherogram of the products, selective primers for PCR which are necessary to amplify the DNA fragments by PCR, are determined. The solution in tube 323 is fractionated and divided into the required number (k) of vessels which corresponds to the number of combinations for PCR. The selective primer for PCR is incorporated into each vessel. Amplification by PCR is conducted using anchored primers and the combination of the primers in a primer set. The thus obtained DNA fragment is purified by dialysis or the like and used as a template for sequencing by the fragment walking method.

In a multi-dye instrument system for sequencing with a set of primers, a number of primers must be prepared which requires much labor. However, in the present invention, a lengthy sample DNA can be readily sequenced using a small number of known primers, by the anchored primers which function to fractionate DNA fragments. In addition, the method of the present invention is very efficient because sequencing can be simultaneously performed from the both ends of the double strand by PCR using a primer having different digestion sites digestible with different restriction enzymes at both ends of the DNA strand.

DESCRIPTION OF THE PREFERRED EMBODIMENTS

Figure 1:
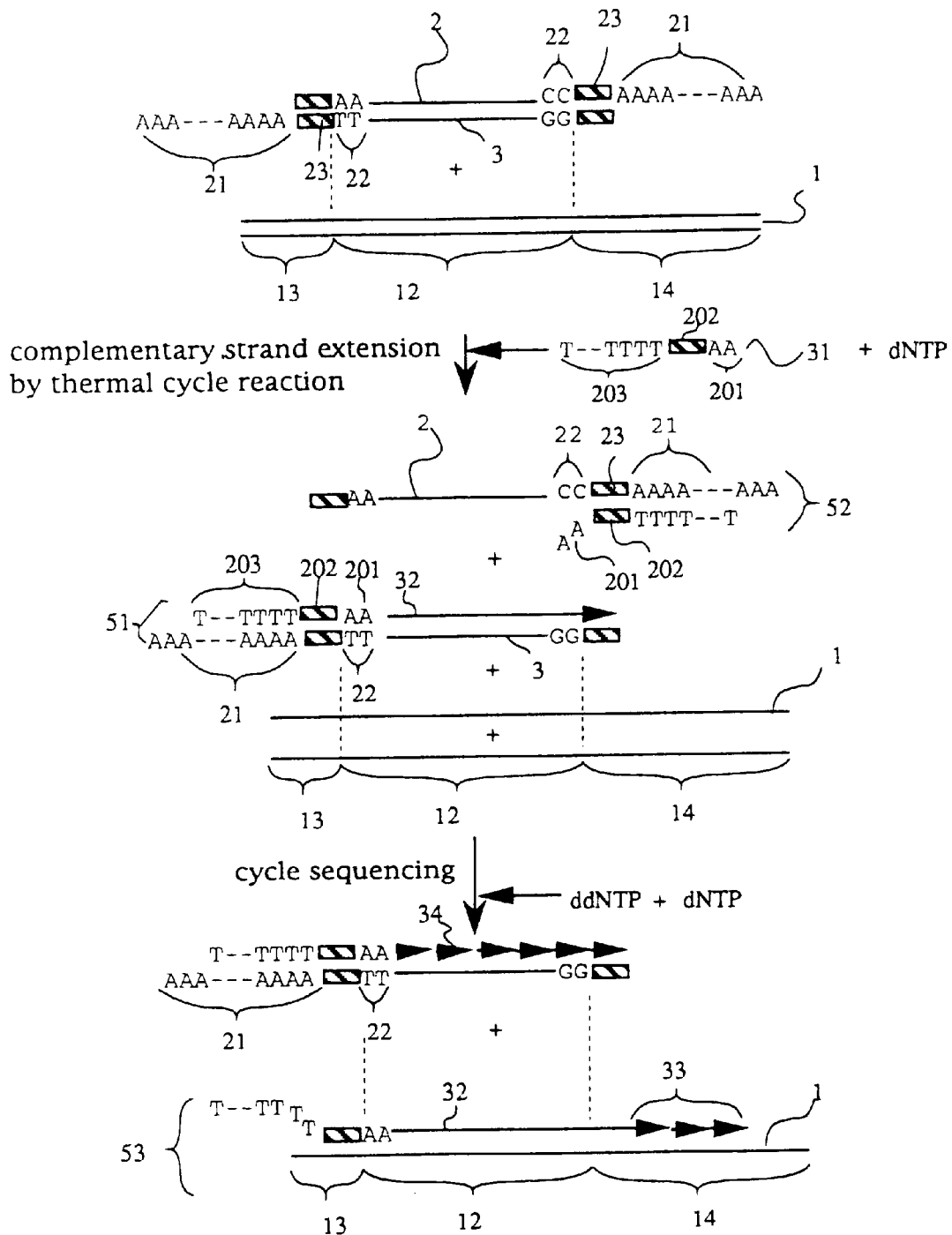
FIG. 1 is a flow chart showing the procedure of Example 1 of the present invention.

Hereinafter the present invention will be described in detail with reference to Examples, by referring to the drawings.

EXAMPLE 1

FIG. 1 is a flow chart showing the procedure in Example 1 of the present invention. In Example 1, steps (5) and (6) described above are continuously carried out to simultaneously determine the base sequence of the selected DNA fragment and the base sequence of a sample DNA adjacent to the base sequence of the selected DNA fragment. Alternatively, steps (5) and (6) can be performed at the same time. As a sample DNA, pUC19 was employed.

Amplification of Sample DNA

Where the amount of sample DNA is small, sample DNA 1 is amplified by PCR. First, in order to make cyclic pUC19 linear, 10 pmols of pUC19 is digested with 100 units of PstI at 37° C. for an hour. Ethanol precipitation is performed in a conventional manner to give linear pUC19. Next, poly A sequence is introduced into the digested pUC19 at the 3' termini using 1 mM ATP and 12 units of terminal deoxynucleotidyl transferase. Primers for PCR hybridize to the poly A region. There are used two primers having the following base sequences:

| TTTTTTTTTTTTTTGCAGGC | (SEQ ID NO. 3) |
|---|---|
| TTTTTTTTTTTTTTGCAGGT | (SEQ ID No. 4) |

PCR was carried out using 96 pmols of each of the two primers, the product of 5 fmol of poly A-tailed pUC19 digested with PstI, 30 nmols each of dATP, dCTP, dGTP and dTTP and 15 units of Taq DNA polymerase. The amount of each reaction solution was 4800 μl. Each reaction solution was divided into 96 aliquots for thermal cycling reaction. The thermal cycling reaction was carried out by repeating twice the cycle of 30 seconds at 94° C., 30 seconds at 47° C. and 5 minutes at 72° C. and then 35 times the cycle of 30 seconds at 94° C., 30 seconds at 55° C. and 5 minutes at 72° C.

In order to remove the unreacted primers and dATP, dCTP, dGTP and dTTP, the reaction mixture was fractionated by 0.7% agarose gel electrophoresis. Approximately 15 pmols of linear pUC19 was obtained as the highly pure PCR product corresponding electrophoretically to a single band of 2.7 Kbp. Hereinafter this linear pUC19, i.e., the PCR product is called sample DNA 1.

Fragmentation of Sample DNA

The PCR product of pUC19 is digested with a restriction enzyme to prepare DNA fragments. In this Example, HhaI is used as a restriction enzyme but a restriction enzyme capable of digesting sample DNA 1 (PCR product of pUC19) is not limited to enzyme HhaI. In FIG. 1, numerals 12, 13 and 14 denote fragments digested by the restriction enzyme. In a solution of 10 mM Tris-HCl (pH 7.5), 10 mM MgCl$_2$, 50 mM NaCl and 1 mM of dithiothreitol 84 units of HhaI is acted on 5.5 pmols of the pUC19 PCR product. The reaction is carried out at 37° C. for an hour. After completion of the reaction, a known base sequence is introduced into the DNA fragments at the 3' end using a part of the reaction solution, in accordance with the method for introducing an oligonucleotide into a DNA fragment at its 3' end, as will be later described.

Figure 2:
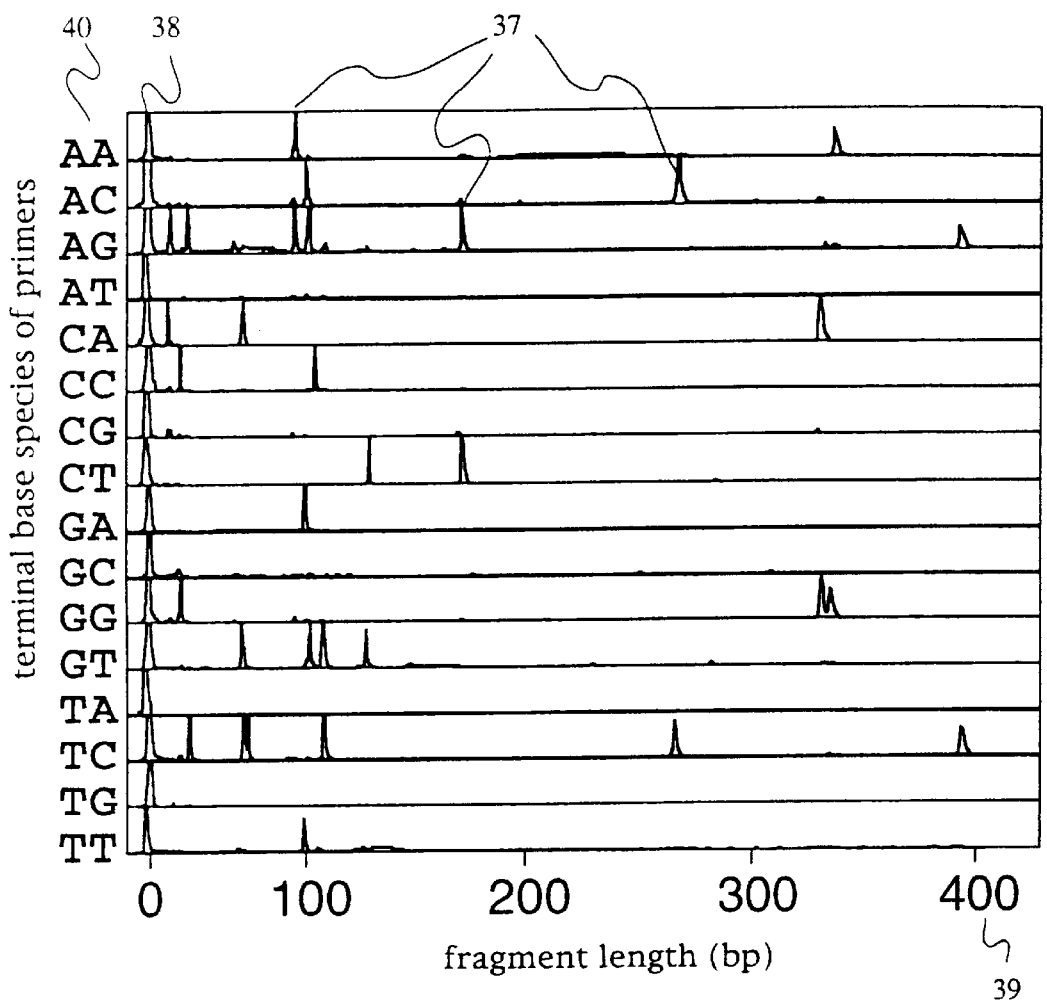
FIG. 2 shows electropherograms of the products by strand extension reaction in Example 1 of the present invention, using fluorophore tagged primers by using as templates the DNA fragments of pUC19 digested with HhaI.
Figure 4:
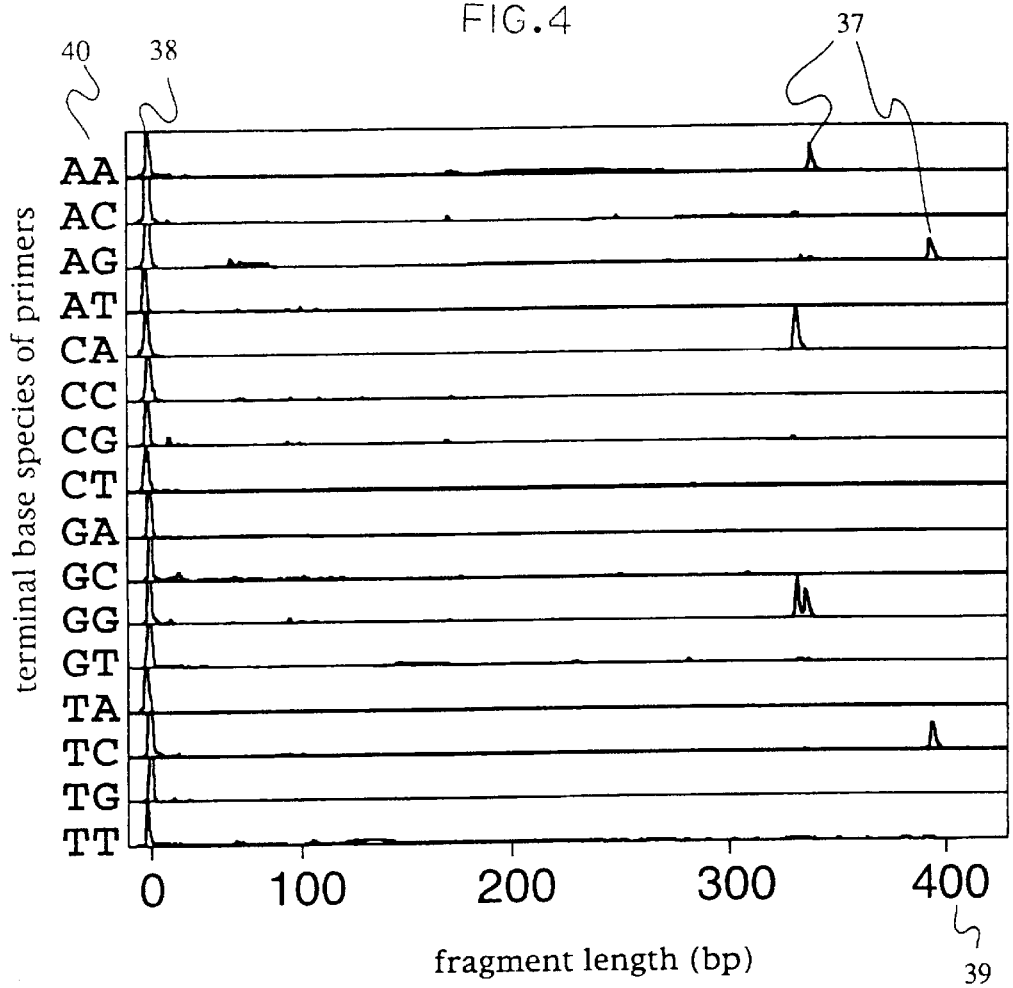
FIG. 4 shows electropherograms of the products by strand extension reaction in Example 1 of the present invention, using fluorophore tagged primers by using as templates the DNA fragments of Fraction 4.

Next, primer extension reaction is carried out using 16 primers TTTTTTTTTTTTTTTCGCXY (SEQ ID NO. 5). The extension reaction products are analyzed on every 16 primers by electrophoresis. FIG. 2 shows the results of the analysis. In FIGS. 2 and 4, numerals 39, 38, 37 and 40 denote base length, electrophoretic peak of each primer, electropherogram of each DNA fragment produced by primer extension reaction, and terminal two base sequence of each primer, respectively. Based on the results shown in FIG. 2, the extension reaction products of the respective primers are fractionated until one kind of the product is given by each primer.

Figure 3:
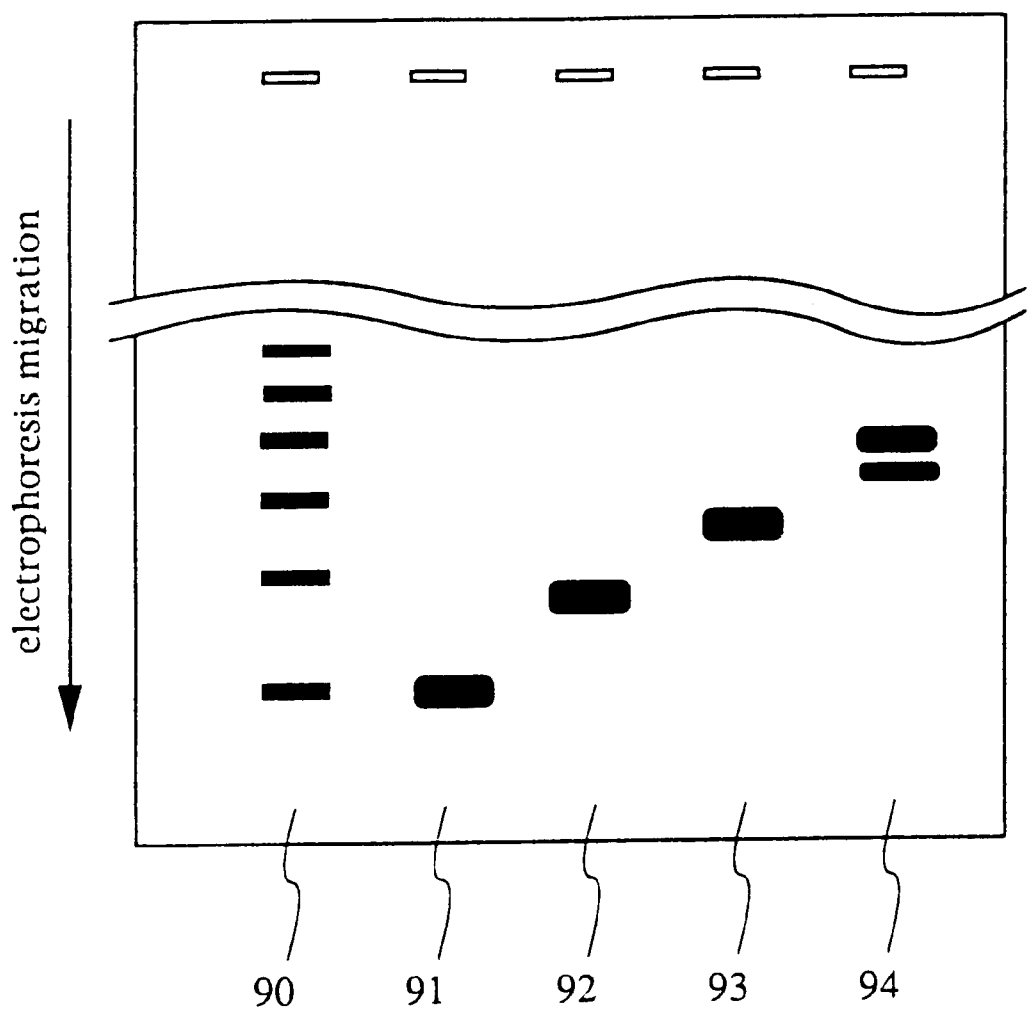
FIG. 3 shows migration patterns of the fractions from the PCR products of pUC19 digested with restriction enzyme HhaI fractionated by agarose gel electrophoresis in Example 1 of the present invention.

For fractionation, the HhaI digestion solution is immediately fractionated by 2% agarose gel electrophoresis to give four fractions of the first to the fourth. As shown in FIG. 3, electropherograms 91, 92, 93 and 94 having four isolated bands are obtained from the first the fourth fractions, respectively. Each band of DNA size marker 90 denotes every 100 base length from the bottom like 100 kb, 200 kb, 300 kb . . . and so on.

Introduction of Oligonucleotide into DNA Fragment at the 3' end Thereof

There are two methods for introducing an oligonucleotide having a known base sequence into a DNA fragment at the 3' end thereof.

A first method comprises introducing an oligonucleotide having a known base sequence into a DNA fragment by ligation. In this method, an oligonucleotide is introduced into a DNA fragment only at the 3' end thereof. Out of a double stranded oligonucleotide for ligation, the 3' end of the double stranded oligonucleotide for use in ligation at the site contiguous to the 5' end of a DNA fragment is converted into a dideoxynucleotide form. Alternatively, the 5' phosphate in a DNA fragment is previously removed. This is because, where a superfluous oligonucleotide is introduced into a DNA fragment at the 5' end, the base sequence missing in the original DNA strand is inserted into the complementary DNA strand formed at step (5) so that step (6) fails to work.

A second method comprises sequentially adding dATP (2'-deoxyadenosine 5'-triphosphate) or dTTP (2'-deoxythymidine 5'-triphosphate) to a DNA fragment at the 3' end thereof using terminal deoxynucleotidyl transferase (hereinafter sometimes referred to as terminal transferase). In this Example, the second method is employed since the second method is simpler and more efficient than the first method.

In order to ensure the site with which a fluorophore tagged primer can hybridize, poly A is introduced into each DNA fragment at the 3' end. For introducing poly A, there is employed terminal deoxynucleotidyl transferase. The reaction conditions are shown below. To approximately 4 pmols of each fraction are added 1 mM dATP, 5 mM CoCl$_2$, 5 mM MgCl$_2$, 0.5 mM mercaptoethanol and 50 mM sodium cacodylate (pH 7.2). Thereafter 12.5 units of terminal deoxynucleotidyl transferase are added to the mixture to react them at 37° C. for an hour.

Discriminating Complementary Strand Synthesis

As shown in FIG. 1, the resulting DNA fragments 2 and 3 have poly A part 21 introduced at the 3' ends, recognition base sequence portion 22 and selected base sequence portion. The selected base sequence portion 22 is a two base portion selected by fluorophore tagged primer 31.

Digestion of a sample DNA with a restriction enzyme gives a plurality of DNA fragments as admixture thereof. For selectively sequencing the objective DNA fragment 3 alone, fluorophore tagged primer 31 is used. In fluorophore tagged primer 31, arbitrary base sequence part 201 is composed of two optional base species and there are 16 combinations in total. Poly T part 203 and recognition base sequence part 303 of fluorophore tagged primer 31 can hybridize completely to poly A part 21 and to recognition base sequence part 23 of DNA fragment 3, respectively.

In complete hybrid 51, the arbitrary base sequence part 201 in fluorophore tagged primer 31 can hybridize only with the DNA fragment 3 having a complementary base sequence 22 to the arbitrary base sequence part 201. Turning to incomplete hybrid 52, however, the arbitrary base sequence part 201 fails to hybridize to a DNA fragment 2 at the terminus thereof. The objective DNA fragment 3 can thus be discriminated by reacting 16 fluorophore tagged primers with DNA fragments.

In practice, only fluorophore tagged primers that can be used for sequencing are previously selected and then sequencing follows. First, 16 μl of a mixture of 0.1 mM dATP, 0.1 mM dCTP, 0.1 mM dGTP and 0.1 mM dTTP and 8 μl of Tris-HCl (250 mM, pH 9.5) supplemented with 75 mM MgCl$_2$ are added to each fraction of the DNA mixture containing approximately 200 fmols of DNA fragments to make the whole volume 48 μl. The mixture is divided by 3 μl each into 16 vessels. To each vessel is added each fluorophore tagged primer (0.001 mM, 0.5 μl) and 2 units/μl of thermostable DNA polymerase (0.5 μl). As the thermostable DNA polymerase, ΔTaq™ and ThermoSequenase™ (both manufactured by Amersham International, Inc.) may be used as they are more effective than Taq polymerase usually employed widely. This is because, with conventional Taq polymerase, an extension reaction often ceases at a specific base sequence portion. A thermal cycle reaction of 94° C., 30 seconds→66° C., 30 seconds→72° C., 60 seconds, is repeated 5 times. The thus obtained products are analyzed by electrophoresis.

FIG. 2 shows the results of the analysis, i.e., migration patterns, prior to fractionation. FIG. 4 shows the migration pattern of Fraction 4 (fraction that gave migration pattern 94 in FIG. 3) after fractionation. FIG. 4 further indicates the migration pattern for two base sequence 40 of the arbitrary base sequence part 201 in each of the primers used.

In the migration patterns of the DNA fragment selected by primers having terminal base species XY (wherein XY denotes the combination of optional two bases) shown in FIG. 4, where no peak other than the primer peak 38 appears at all, this means that any DNA fragment reactive with primers is absent. In FIG. 4, only one peak is detected in the electropherogram of the DNA fragment selected by the primer having two base sequence of AA, meaning that the primer hybridized to only one DNA fragment. Therefore, this procedure enables sequencing as explained hereinbelow.

In FIGS. 2 and 4, the electropherogram in which two peaks or more appear (for example, the migration pattern of the DNA fragment selected by the primer having the terminal two base sequence GG shown in FIG. 4) indicates that the fluorophore tagged primer used hybridizes to a plurality of DNA fragments. The migration pattern of the DNA fragment selected by the primer having the terminal two base sequence GG shown in FIG. 4 indicates that the fluorophore tagged primer having GG as the arbitrary base sequence part 201, acted as a fluorophore tagged primer for two DNA fragments. This fluorophore tagged primer having GG as the arbitrary base sequence part 201 is not appropriate when it is desired to sequence only one kind of DNA fragment having a specific base sequence.

In FIG. 4, however, the left peak of the two contiguous peaks in the migration pattern of the DNA fragment selected by the primer having the terminal two base sequence GG is equal in fragment length to the peak in the migration pattern of the DNA fragment selected by the primer having the terminal two base sequence CA. Likewise, the right peak of the two contiguous peaks in the migration pattern of the DNA fragment selected by the primer having the terminal two base sequence GG is equal in fragment length to the peak in the migration pattern of the DNA fragment selected by the primer having the terminal two base sequence AA. That is, the DNA fragments which provide the same fragment length (migration time) are in relation of + strand and − strand in double strands. Accordingly, the two DNA fragments selected by the primer having terminal two base sequence GG can be discriminated from each other by PCR using primers having terminal base sequences CA and GG or terminal two base sequences AA and GG, which are adjacent to the recognition base sequence part of each DNA fragment.

In the explanation above, the embodiment in which DNA fragments are discriminated from each other using primers having an arbitrary base sequence of two bases XY (wherein XY represents the combination of two optional bases) is used as an example. The DNA fragments may also be discriminated from each other using primers having an arbitrary base sequence of three bases XYZ (wherein XYZ represents the combination of three optional bases) or four bases WXYZ (wherein WXYZ represents the combination of four optional bases). As described above, fluorophore tagged primers for use in sequencing can be readily selected in advance.

Complementary Strand Synthesis and Sequencing

Next, sequencing is carried out using the thus selected fluorophore tagged primer. Herein, the procedure is explained using an example in which Fractions 1 and 4, showing migration patterns 91 and 94 in FIG. 3, respectively, are employed as DNA fragments. The analytical (electrophoretic) results of the fractions after fractionation reveal that in Fractions 1 and 4, the fluorophore tagged primer having AA as the arbitrary base sequence part 201 hybridizes to only one DNA fragment. Accordingly, the base sequence of the DNA fragment to which the fluorophore tagged primer 31 hybridizes is determined as follows, using the primer 31 having AA as the arbitrary base sequence part 201.

A sequencing reaction is carried out by adding the intact PCR product (sample DNA 1) not digested with HhaI, since the fluorophore tagged primer 31 also reads the base sequence of DNA fragment 14 adjacent to DNA fragment 3 or 12. The fluorophore tagged primer 31 completely hybridizes to poly A-tailed DNA fragment 3 but does not hybridize to sample DNA 1. The extended DNA strand 32 obtained by complementary strand synthesis using DNA fragment 3 as a template hybridizes to sample DNA and by sequencing reaction, the extended DNA strand 33 is produced. In DNA sequencing, the number of DNA fragments decreases as the fragment length is prolonged to reduce a signal intensity.

In order to ensure a satisfactory signal intensity from the extended DNA strand 33 obtained by extension of the extended DNA strand 32, it is effective to previously extend the fluorophore tagged primer 31 to the 5' end of DNA fragment 3 using only dNTP (a mixture of DATP, dCTP, dGTP and dTTP) to produce the extended DNA strand 32 in a large quantity. Thereafter sequencing is carried out using the extended DNA strand 32 by using sample DNA 1 as a template to obtain the extended DNA strand 33. That is, after the extended DNA strand 32 which functions as a primer for intact sample DNA 1 is produced in a large quantity, dideoxynucleotide is added thereto followed by sequencing. The details of the reaction are set forth below. To Fraction 1 or 4 containing approximately 100 fmols of each DNA fragment are added 2 µl of the fluorophore tagged primer 31 (1 pmol/µl), 4 µl of dNTP and 2 µl of Tris-HCl (250 mM, pH 9.5) supplemented with 75 mM MgCl$_2$ to make the whole volume 14 µl. The mixture is divided by 3.5 µl each into 4 vessels. To each vessel is added 2 units/µl of Taq DNA polymerase (ΔTaq polymerase (Amersham), 0.5 µl). A thermal cycle reaction of 94° C., 30 seconds→64° C., 30 seconds→72° C., 60 seconds, is repeated 5 times to obtain a large quantity of the extended DNA strand 12 to the 5' end of the DNA fragment 3.

Next, 12.5 fmols of the PCR product (sample DNA 1), dideoxynucleotide (ddNTP) and 4.5 µl of a deoxynucleotide mixture are added to the reaction solution containing large quantities of the extended DNA strand 32, respectively. The dideoxynucleotide and deoxynucleotide used for the reaction are as follows:

for A termination reaction, 0.020 mM dNTP and 1.0 mM ddATP;

for C termination reaction, 0.020 mM dNTP and 0.50 mM ddCTP;

for G termination reaction, 0.020 mM dNTP and 0.10 mM ddGTP; and, for T termination reaction, 0.020 mM dNTP and 1.0 mM ddTTP.

The mixture is subjected to a thermal cycle reaction of 94° C., 30 seconds→64° C., 30 seconds→72° C., 60 seconds, 30 times. Ethanol precipitation is performed to recover the reaction products. The reaction products are subjected to electrophoresis and sequenced with a fluorescent DNA sequencer.

Figure 5:
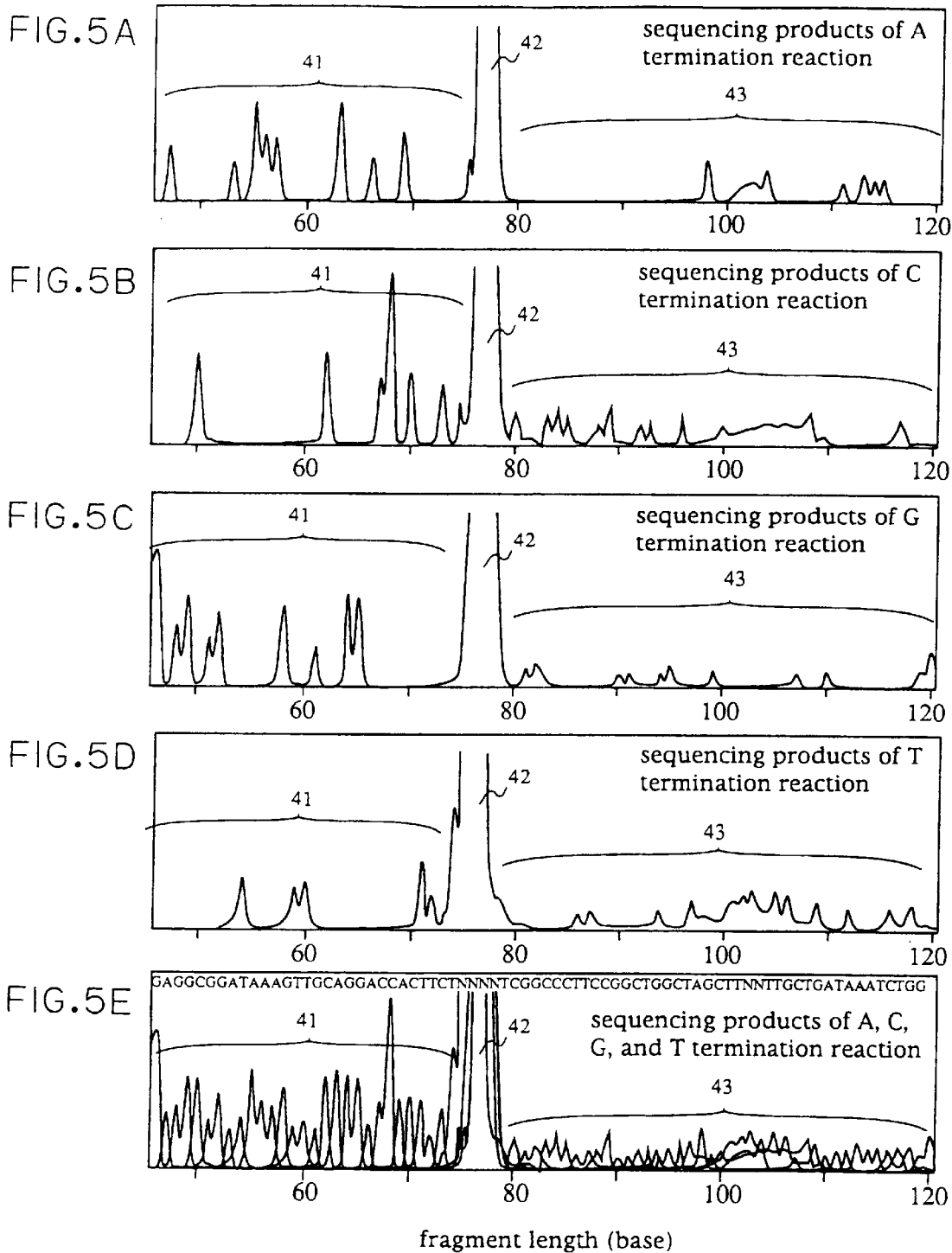
FIGS. 5A, 5B, 5C, 5D and 5E show electropherograms of the sequencing products obtained from Fraction 1 in Example 1 of the present invention.
Figure 6:
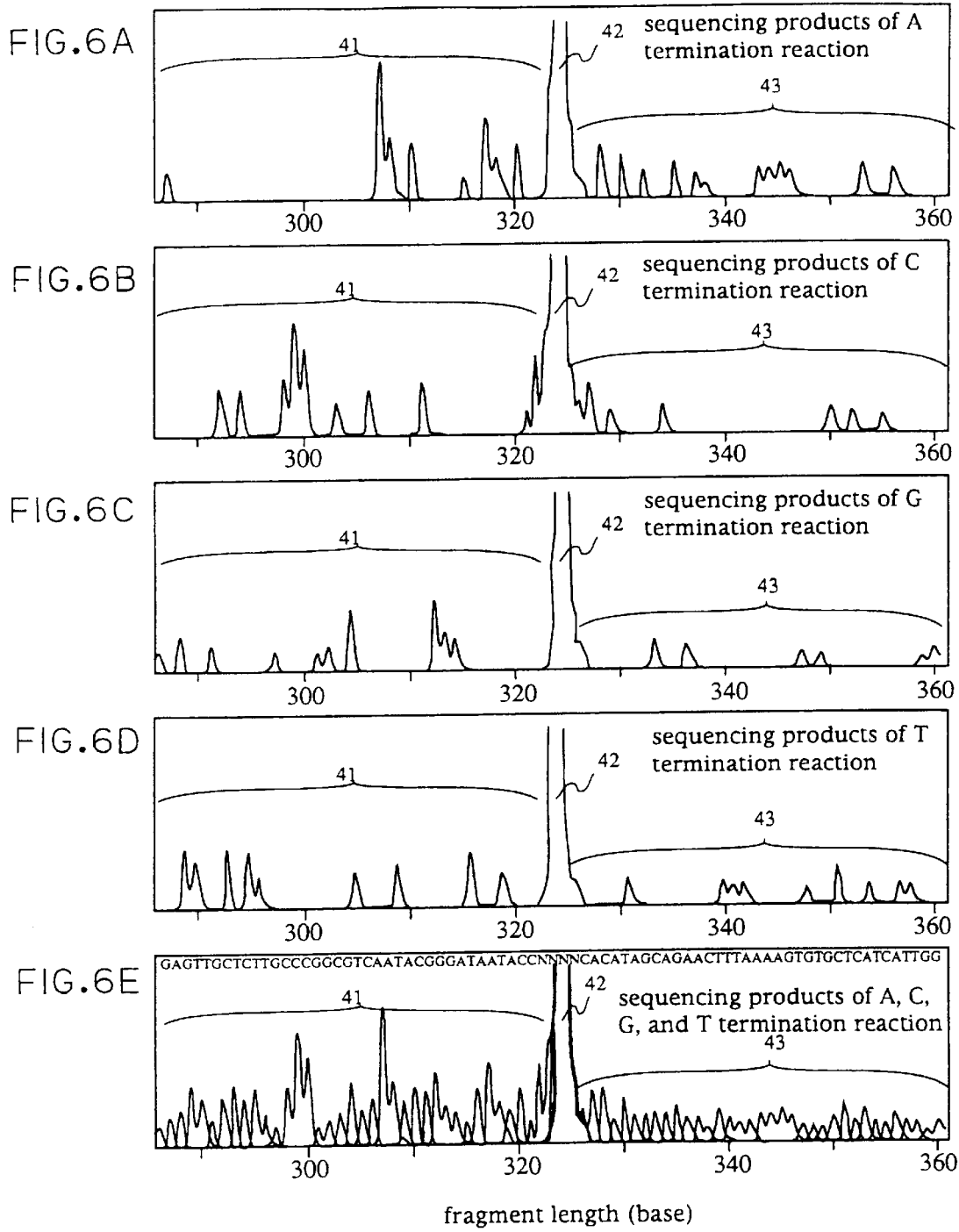
FIGS. 6A, 6B, 6C, 6D and 6E show electropherograms of the sequencing products obtained from Fraction 4 in Example 1 of the present invention.

The electrophoresis of the mixed DNA fragments in Fractions 1 and 4 gives clear electropherograms shown in FIGS. 5A through 5E and FIGS. 6A through 6E. FIGS. 5A and 6A, 5B and 6B, 5C and 6C, and 5D and 6D show the electropherograms of fragment A groups terminated with A, the electropherograms of fragment C groups terminated with C, the electropherograms of fragment G groups terminated with G and the electropherograms of fragment T groups terminated with T, respectively, at the 3' end by extension of fluorophore tagged primer 31. FIGS. 5E and 6E indicate the overlaid electropherograms of the respective DNA fragment groups of A, C, G and T. The migration patterns 41, 42 and 43 are given by the DNA fragment sequencing products produced using DNA fragment 3 as a template (extended DNA strand 34 in FIG. 1), the DNA fragment produced by extension of fluorophore tagged primer 31 to the 5' end of DNA fragment 3 in which the extension reaction terminated (extended DNA strand 32 shown in FIG. 1) and extended DNA strand 33 by further extension of the extended DNA strand 32 (FIG. 1) ligated with DNA, respectively.

In conventional sequencing, only migration patterns 41 and 42 are obtained. However, in this Example, the base sequence of DNA fragment 3 can be determined and at the same time, the contiguous sequence of sample DNA adjacent to DNA fragment 3 can also be determined. In the embodiment, it is assumed that a lengthy sample DNA is fully digested with a 4-base cutter restriction enzyme. Even if the sample DNA is not completely digested with a 4-base cutter restriction enzyme, there is no problem for sequencing if, e.g., 20 to 30% of the sample DNA is digested with a 4-base cutter restriction enzyme. Furthermore, beyond the portion ideally digested with a restriction enzyme, at least a part of the contiguous sequence of the digested DNA fragment by a restriction enzyme can also be determined.

In this embodiment, the DNA fragments complementary to the 3'-terminal arbitrary base sequence part 201 of fluorophore tagged primer 31 and to the selected base sequence part 22 adjacent to recognition base sequence part 22 recognized by a restriction enzyme can be selected by fluorophore tagged primer 31 from the fragments of sample DNA 1 digested by a restriction enzyme to effect selective sequencing. The selectivity can be improved by setting an annealing temperature for formation of complementary strand at 60° C. or higher, preferably in the range of 62 to 68° C.

The complementary strand extension reaction proceeds from the 3' terminus to the 5' terminus of DNA fragment 3 with which fluorophore tagged primer 31 has hybridized. In conventional DNA sequencing, dideoxynucleotide is added as any one of particular base species A, C, G and T so that the extension reaction terminates at the site where the dideoxynucleotide is introduced. The extended DNA strand 32 is a DNA strand which reached the 5' terminus of DNA fragment 3. When no dideoxynucleotide is added to the reaction system, the extended DNA strand 32 reaches the 5' terminus of DNA fragment 3. Using sample DNA 1 as a template, the sequencing reaction using the DNA fragment-extended DNA strand 32 as a primer reaches also DNA strand part 14 beyond the part digested with a restriction enzyme and hence, the base sequence of the DNA strand part 14 can also be determined. In order for the extended DNA strand 32 produced by one complementary strand synthesis to function as a primer for sample DNA 1, it is necessary that the extended DNA strand 32 should isolated from DNA fragment as the template and dissociated into a single strand by heat denaturation. Thermal cycle sequencing is used for the isolation. A cycle sequencing comprising the steps of hybridization (e.g., 64° C. for 30 seconds) of primer (fluorophore tagged primer 31 and extended DNA strand 32) to the template DNA (DNA fragment 3 and sample DNA 1), performing complementary strand extension reaction (e.g., 72° C. for 60 seconds) and dissociating the extended primer from the template DNA by heat denaturation is repeated, for example, 30 times. Using cycle sequencing, DNA fragment 34 extended on the way to DNA fragment 3 using DNA fragment 3 as a template, and extended DNA strand 33 obtained by extension of the extended DNA strand 32 using sample DNA 1 as a template, can be obtained simultaneously. As the result, the base sequence of DNA fragment 3 and at least a part of the base sequence of the sample DNA adjacent to the 3' terminus of DNA fragment 3 can be determined. With respect to other DNA fragments, the base sequence of each DNA fragment and at least a part of the base sequence of the sample DNA adjacent to the 3' terminus of each DNA fragment, can also be determined.

The base sequence of each DNA fragment formed by a restriction enzyme and the contiguous sequence of sample DNA adjacent to the 3' terminus of each DNA fragment overlap the base sequence of another DNA fragment around the 5' terminus thereof so that the base sequences of the respective DNA fragments can be readily linked with each other. Furthermore, the restriction enzyme site in a sample DNA can be easily detected since the peak of the primer extension products 32 extended to the terminus of DNA fragment 3 by a complementary strand extension reaction is observed intensively. In actuality, some of the DNA fragments of pUC19 by HhaI can be sequenced in such a manner as described in this embodiment so as to examine how to link the base sequences with each other. Therefore, the overall full-length base sequence of pUC19 can be determined without cloning.

Figure 7:
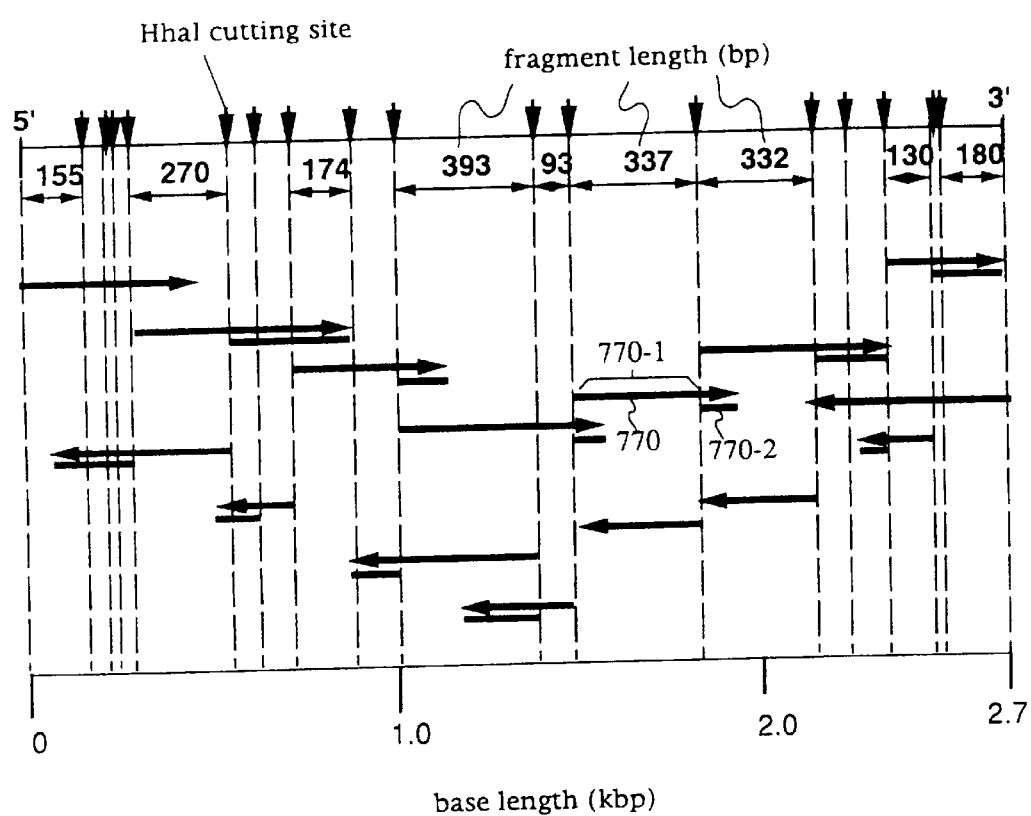
FIG. 7 is a drawing for explaining the sequencing of pUC19 in Example 1 of the present invention.

FIG. 7 is a drawing explaining the sequencing of pUC19 (2.7 Kbp in full length) in Example 1 of the present invention. In FIG. 7, symbol ↓ denotes cutting site with HhaI, numeral values such as 270, 393, etc. around symbol ←--→ denote the length between the cutting sites of the restriction enzyme (the number of bases), the abscissa denotes base length and symbols --→ and ←-- denote the portion to be sequenced in this embodiment, respectively, and symbol --→ and symbol -, shown parallel to symbol ←-, denote the base sequence part adjacent to the HhaI-digested DNA fragment to be sequenced in the embodiment (the base sequence part which provides information how to link the base sequences of the respective DNA fragments with each other). Further in FIG. 7, the sequencing site 770 is the portion determined by the migration patterns shown in FIG. 6 and composed of the base sequence part of DNA fragment 770-1 and the base sequence 770-2 which is a part of the DNA fragment adjacent to DNA fragment 770-1. As shown in FIG. 7, information from the base sequence part shown by—which provides information how to link the base sequences of the respective DNA fragments with each other, can be efficiently utilized, whereby the pre-base sequence of pUC19 having full base length of 2.7 Kbp can be determined.

EXAMPLE 2

In this embodiment, where a sample of lengthy DNA is obtained by cloning, a long DNA fragment obtained by digesting the sample DNA with the restriction enzyme used for cloning is used as sample DNA 1. The method of the present invention will be described below, taking as an example the case in which the method is applied to lambda DNA. A key for successful sequencing lies in first performing complementary strand synthesis using 16 primers (in the case that the arbitrary base sequence part for selecting DNA fragments are two bases) and properly judging how many DNA fragments of what length are present and which DNA fragment should be taken out by fractionation.

Figure 8:
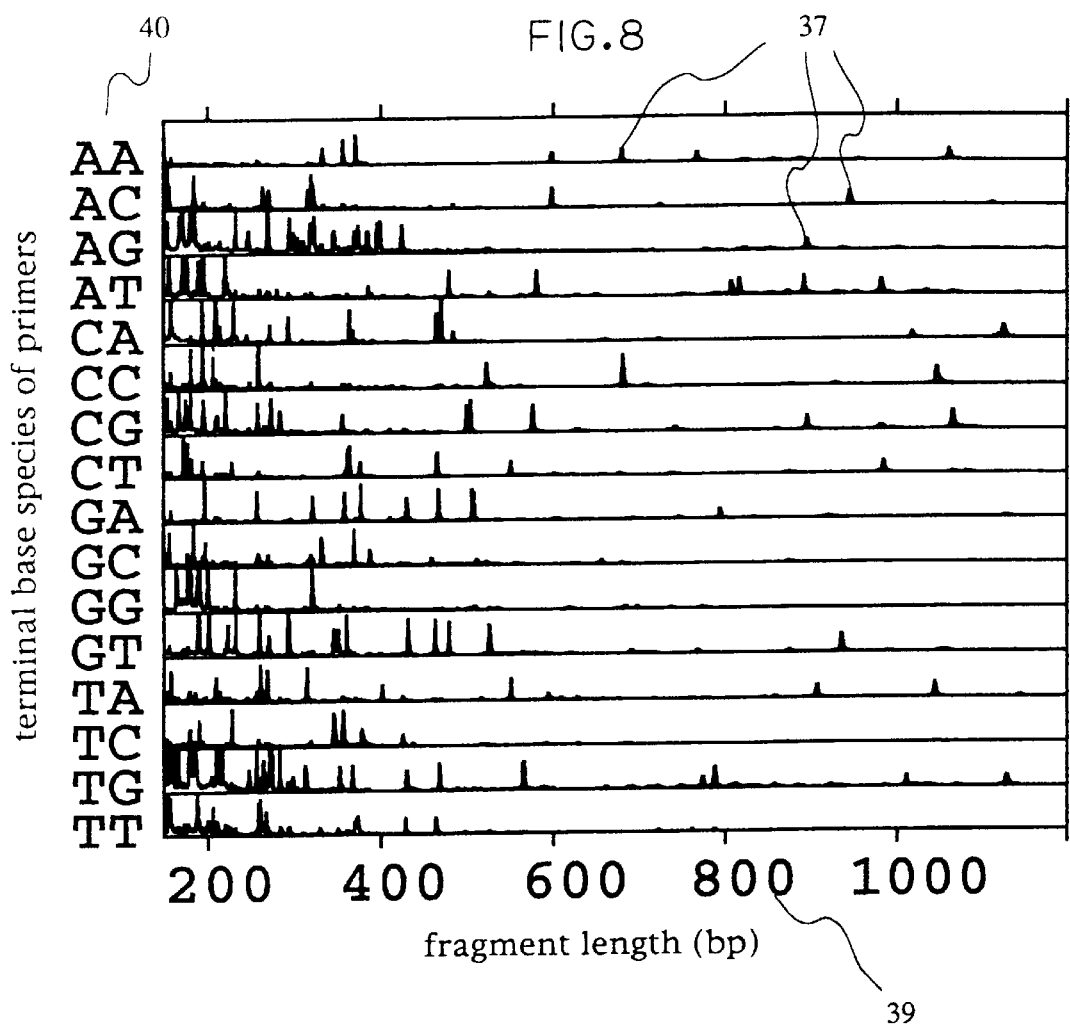
FIG. 8 shows electropherograms of the products by strand extension reaction in Example 2 of the present invention, using fluorophore tagged primers by using as templates the DNA fragments of lambda DNA digested with HhaI.

FIG. 8 shows electropherograms of the products obtained by strand extension reaction using fluorophore tagged primers, and using as templates the DNA fragments of lambda DNA (47.7 Kbp) digested with HhaI. When there are too many products as shown in FIG. 8, it is difficult to fractionate the DNA fragments. For sequencing of a huge sample DNA such as lambda DNA, it is desired to first digest the sample DNA with, e.g., a 6-base cutter restriction enzyme, separate and fractionate the resulting DNA fragments by electrophoresis and further digest each of the fractionated DNA fragments with a 4-base cutter restriction enzyme; thereafter, the base sequence can be determined as in the case of pUC19 in Example 1. For example, PstI and HhaI may be employed as the 6-base and 4-base cutter restriction enzymes, respectively.

EXAMPLE 3

In general, long DNAs obtained by cloning are stored in many research laboratories in the form of a DNA library. Alternatively, cloning in the region of a DNA to be sequenced in most cases has been completed. According to the present invention, the base sequence can be determined efficiently without subcloning even in the instance where cloning has already occurred. This embodiment will be explained with reference to, e.g., linear DNA as sample DNA 1 which is obtained by digesting pUC19 as a model with restriction enzyme PstI. This embodiment is different from Example 1 in that linear pUC19 digested with PstI is used as sample DNA 1. Hereinafter the procedures are explained by referring to the same numbering system as used in FIG. 1. With 100 units of PstI is digested 10 pmols of pUC19 at 37° C. for an hour. Ethanol precipitation is carried out in a conventional manner. Since PstI digests pUC19 at one site, linear pUC19 is obtained.

The base sequence is determined as in Example 1, which will be described below. The linear pUC19 is digested with restriction enzyme HhaI to prepare DNA fragments. The DNA fragments are fractionated into 3 fractions by agarose electrophoresis. A fluorophore tagged primer 31 used for sequencing is selected from 16 fluorophore tagged primers. Using fluorophore tagged primer 31, an extension reaction is carried out to obtain extended DNA strand 32. Next, the extended DNA strand 32 is extended using pUC19 as a template to obtain extended DNA strand 33 and the base sequence is determined as in Example 1. As the result, the base sequence of specific DNA fragment 3 and the sequence of sample DNA 1 (pUC19) adjacent to the 3' terminus of DNA fragment 3 can be determined.

EXAMPLE 4

Figure 9:
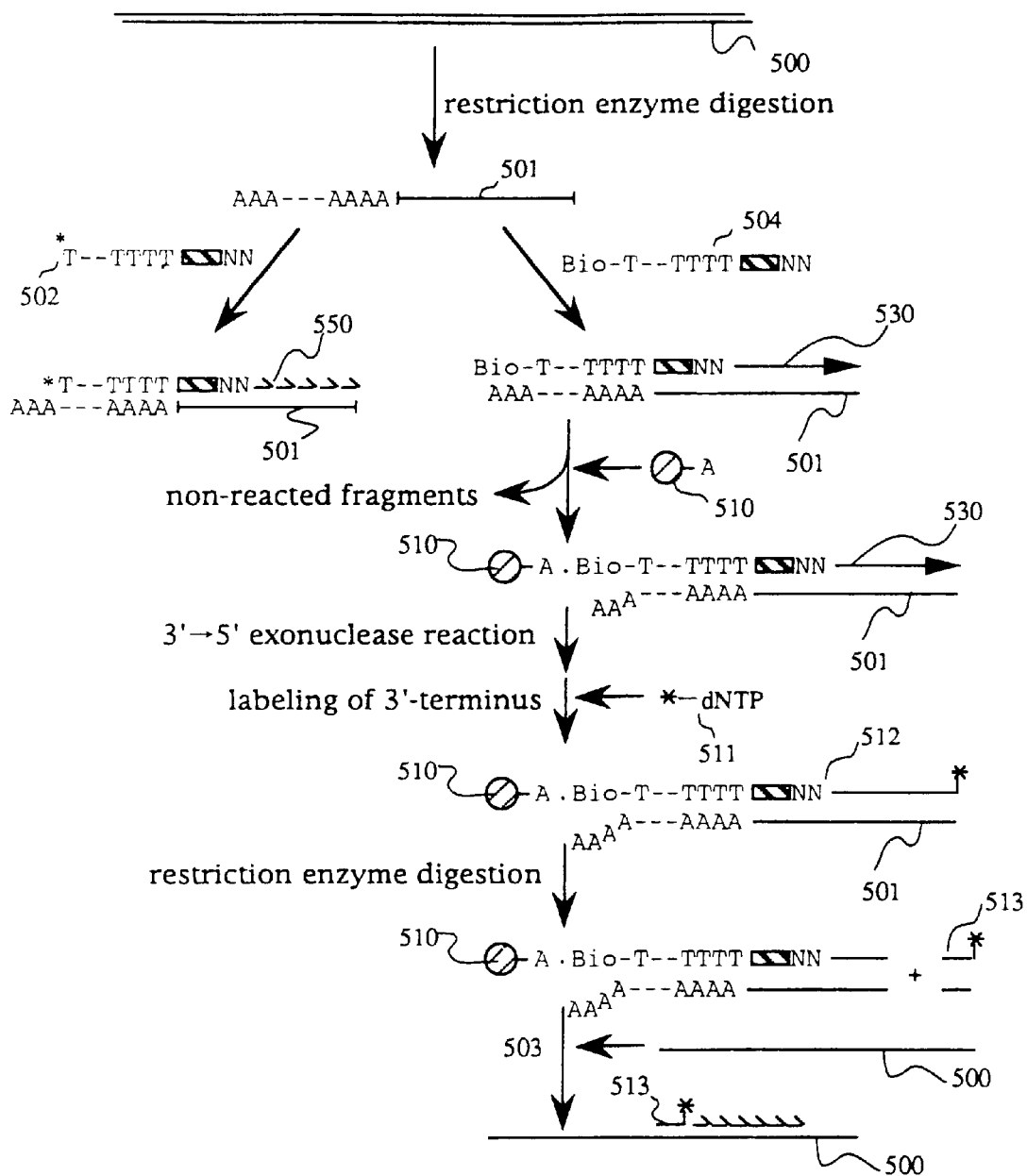
FIG. 9 is a flow chart showing the procedure of Example 4 of the present invention.

When the length of a DNA fragment reaches 400 to 500 bases or more, it is difficult to obtain a sufficient numbers of DNA fragments. In addition to decreased signal intensity from the DNA fragment, there is another problem that the ability of fractionating DNA strand length can also decrease. These problems can be solved by, e.g., the following procedures, which will be explained by referring to FIG. 9.

As in Example 1, poly A is tailed at the 3' end of DNA fragment 501 obtained by digesting sample DNA 500 with a first restriction enzyme. Using the poly A-tailed DNA fragment 501 as a template, sequencing is carried out by using fluorophore tagged primer 502 (called a first primer) which hybridizes to the recognition base sequence part by the restriction enzyme and the contiguous unknown base sequence part adjacent to the recognition base sequence part. The resulting DNA fragments 550 having various lengths are electrophoresed and the base sequence of DNA fragment 501 is determined with a fluorescent DNA sequencer. Then, biotinylated primer 504 obtained by labeling the first primer with biotin is prepared.

Using the poly A-tailed DNA fragment 501 as a template, complementary strand synthesis is carried out to obtain DNA fragment 530 by the complementary strand synthesis. The DNA fragment 530 obtained by complementary strand synthesis is trapped by avidin-immobilized beads 510 to remove the DNA fragment 530 from the reaction solution. Thereafter, the 3' terminus of DNA fragment 530 obtained by complementary strand synthesis is decomposed by fluorophore tagged dNTP 511 and DNA polymerase having a 3'-exonuclease activity (3'→5' exonuclease reaction). Fluorophore tagged dNTP 511 is newly added to the reaction mixture to obtain fluorophore tagged DNA strand 512 having a fluorescent label at the 3' terminus thereof (3'-terminal recognition reaction).

At this step, a second restriction enzyme for digesting double stranded DNA around the 3' terminus of DNA fragment 501 is determined based on the base sequence of DNA fragment 501 previously sequenced. The fluorophore tagged DNA strand 512 is digested with the second restriction enzyme to obtain second primer 513 used as a short fluorophore tagged primer. Using sample DNA 500 as a template, the second primer 513 is extended by sequencing reaction 500, and the base sequence is determined as in Example 1. Of course, the extension product of the second primer 513 may be digested with the second restriction enzyme after extension of fluorophore tagged DNA strand 512 having a fluorescent label at the 3' terminus through sequencing reaction using sample DNA 500 as a template. The second primer 513 is complementary to a part of sample DNA 500, and the extension product of second primer 513 produced by the sequencing reaction is shortened by the length digested with the second restriction enzyme. The products obtained by the sequencing reaction can be detected with a fluorescent DNA sequencer up to a longer DNA fragment length so that the base sequence can be determined more accurately.

EXAMPLE 5

Figure 10:
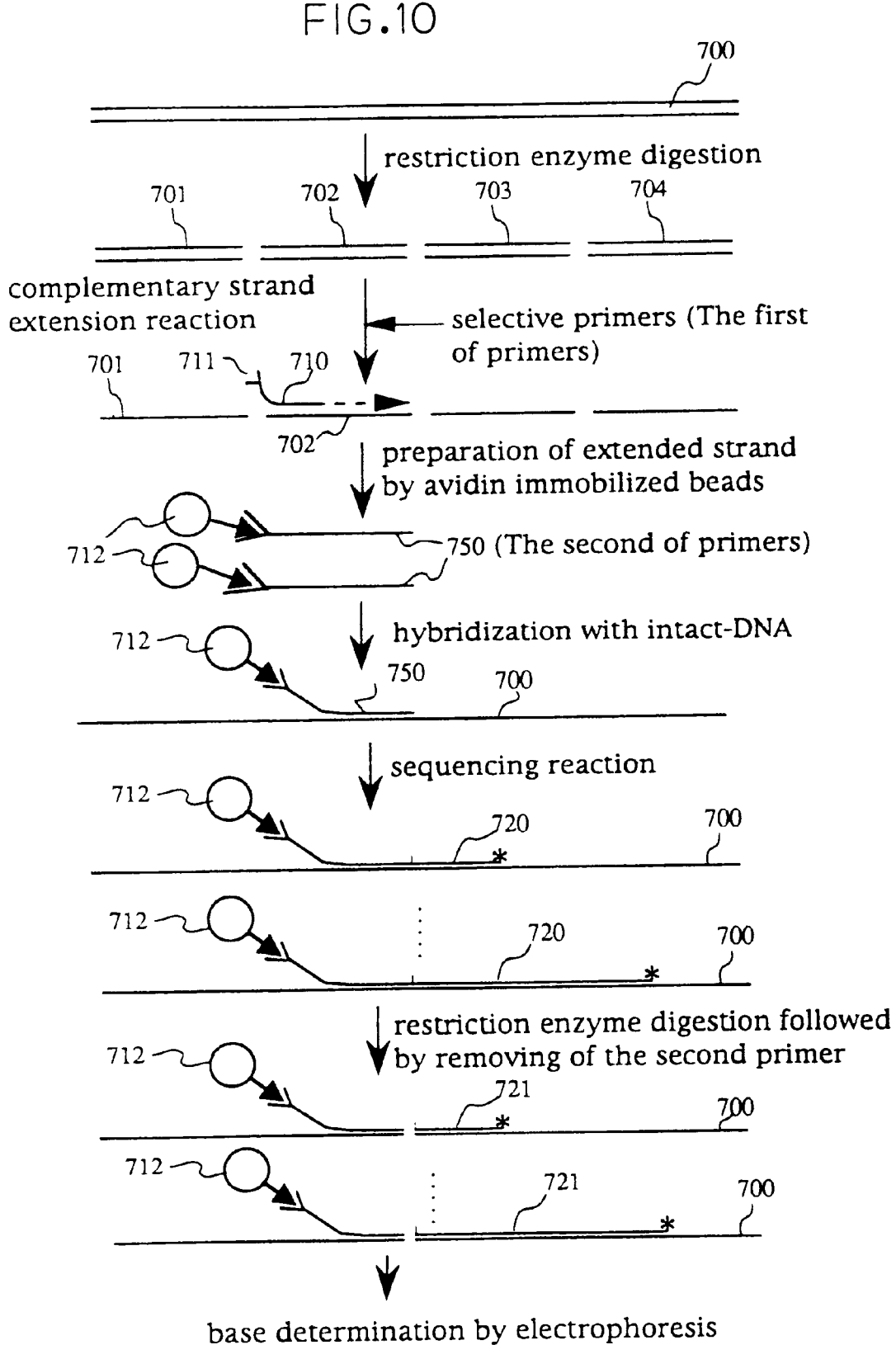
FIG. 10 is a flow chart showing the procedure of Example 5 of the present invention.

In Example 4 above, DNA strand 512 tagged with fluorophore at the terminus is digested with the second restriction enzyme which is different from the first restriction enzyme. In this embodiment, the DNA strand extended using a fluorophore tagged terminator is digested with the same restriction enzyme as used for producing DNA fragments and the base sequence adjacent to each DNA fragment is determined. The procedures of this embodiment are shown in FIG. 10.

Sample DNA 700 is digested with, e.g., restriction enzyme HhaI to give DNA fragments 701, 702, 703 and 704. Thereafter, the strand complementary to the objective DNA fragment 702 is prepared using a first primer 710 having a discrimination sequence at the 3' terminus thereof. The 5' terminus of the first primer 710 is labeled with biotin 711. Using avidin-immobilized beads 12, the first primer 750 extended by complementary strand extension reaction is isolated. After removing DNA fragment 702 used as the template, the extended single strand from the first primer 710 is used as a primer for sequencing, which is called second primer 750.

The second primer may also be isolated using magnetic beads instead of avidin-immobilized beads 712. The second primer 750 is mixed with sample DNA 700 and a sequencing reaction solution is added to the mixture followed by sequencing. Thus, DNA fragment 720 having a fluorescent label at the 3' end is obtained. Subsequently, DNA fragment 720 is digested with restriction enzyme HhaI and the second primer 750 is removed. The resulting DNA fragment 721 is electrophoresed and sequenced with a fluorescent DNA sequencer. According to this embodiment, the base sequence of sample DNA 700 adjacent to the 3' terminus of DNA fragment 702, to which the first primer 710 hybridizes, can be determined. That is, the base sequence of DNA fragment 703 can be determined.

EXAMPLE 6

As shown in Example 2, where the base sequence of a huge DNA sample of several ten kbp is determined, it is advantageous to first digest the sample DNA with a 6-base cutter restriction enzyme, separate and fractionate by electrophoresis, further digest each of the resulting DNA fragments with a 4-base restriction enzyme and apply to the DNA fragments the procedures explained in the Examples above. Thus, the overall base sequence can be determined. The fractionation and sequencing described above can be automatically processed under the control of a computer.

The whole system for performing the fractionation and sequencing above comprises a fractionation apparatus, a sequencing apparatus (robot) and a high-throughput DNA sequencer such as a capillary arrayed electrophoretic instrument. Therefore, the system can be operated without requiring any particular skill.

Figure 11:
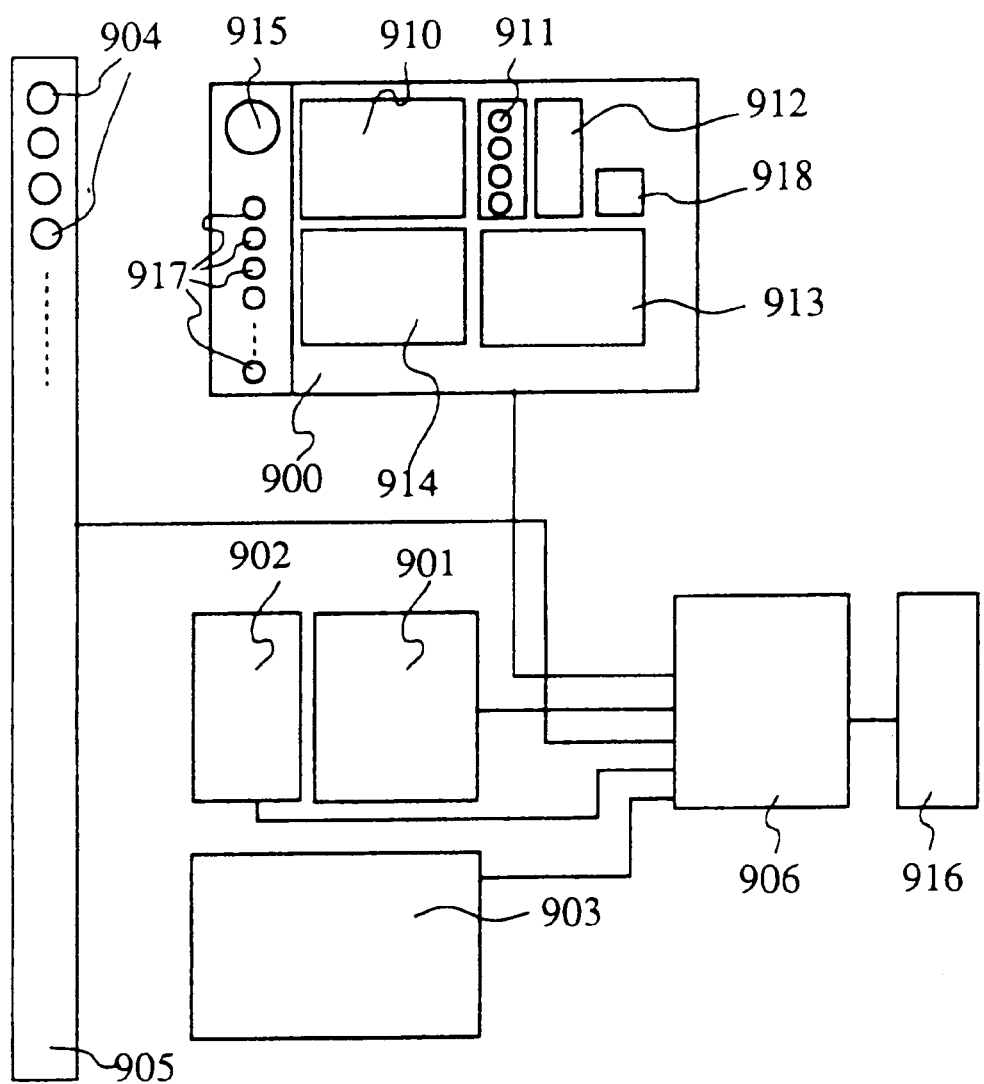
FIG. 11 shows a construction of the system for performing a series of procedures for fractionation and sequencing in Example 5 of the present invention.

FIG. 11 shows a construction of the system for performing a series of procedures for fractionation and sequencing. The system shown in FIG. 11 is constructed by enzyme reaction apparatus 900, fragment analysis apparatus 901, electrophoresis apparatus 902 for fractionating fragments, DNA sequencer 903, XYZ stage apparatus 905 for moving a plurality of pipettes 904 by holding these pipettes 904 for sending sample, reaction products, etc. between the apparatuses and instruments, and computer 906 for controlling the movement of each apparatus under the predetermined program.

The enzyme reaction apparatus 900 is constructed by primer set holding portion 910, holding 16 primers and having at least 16 sections; reacting reagent holding portion 911 for holding reagents such as enzyme, buffer, etc.; enzyme digesting reaction portion 912 for performing the digestion of a sample DNA with a restriction enzyme; DNA recovery portion 913 for recovering the reaction products at the enzyme digesting reaction portion, extension reaction portion 914 having at least 16 sections for extension reaction; sequencing reaction portion 918 in which sequencing is carried out; pipette washing portion 915 and sample holding portion 917 for holding sample DNA. Each portion constructing the enzyme reaction apparatus 900 is independently controlled by a temperature controlling apparatus (not shown) under the control of a computer 906. Movement of sample solutions, reagents and solutions containing reaction products between these portions is made through pipettes 904. The position and movement of pipettes 904 are controlled by XYZ stage apparatus 905. Control of the aspiration filling and discharging of solutions from and into the pipettes is made by control signal from the computer 906, together with the control of movement.

Sample DNA is taken from the sample holding portion 917 to the enzymedigesting reaction portion 912 through pipette. From the reacting reagent holding portion 911 restriction enzymes and the like are separated and added to the enzyme digesting reaction portion 912 and the reaction is carried out by maintaining at 37° C. for an hour. After completion of the reaction, the reaction solution is moved into the DNA recovery portion 913 through pipette 913, in which DNA digested with restriction enzyme is recovered. The DNA recovery portion 913 is constructed of a silica-beads membrane and a pump. DNA is recovered first by trapping DNA with a silica bead filter, washing and then washing with water. A part of the thus recovered digested DNA is divided into 16 aliquots followed by an extension reaction at the extension reaction portion 914, using a set of 16 primers. The reaction products are sent to the fragment analysis apparatus 901 through pipette, in which the reacted primers and fragment length are measured. The results of measurement are analyzed with the computer 906 and the range of the DNA fragment mixture for fractionation is determined so that each primer can utilize one fragment extension. The DNA fragment mixture remaining in the DNA recovery portion 913 is sent to the electrophoresis apparatus 902 for fractionation to fractionate the DNA fragment mixture into 2–5 fractions.

Each fraction is moved to the sequencing reaction portion 918, where a sequencing reaction is performed. Reagents necessary for the sequencing reaction are supplied from the reacting reagent holding portion 911 to the sequencing reaction portion through pipette. The sequencing reaction products obtained in the sequencing reaction portion 918 are sent to the DNA sequencer 903 and electrophoresed there, whereby the electrophoretic results necessary for sequencing are obtained. Based on the electrophoretic results from each fraction, the base sequence of sample DNA can be determined. DNA sequencing of the sample DNA can be made by computer 906 or a computer DNA sequencer 903 has independently. The computer 906 is equipped with display apparatus 916, on which the status of various controls, base sequence information and the like are displayed.

EXAMPLE 7

Figure 12:
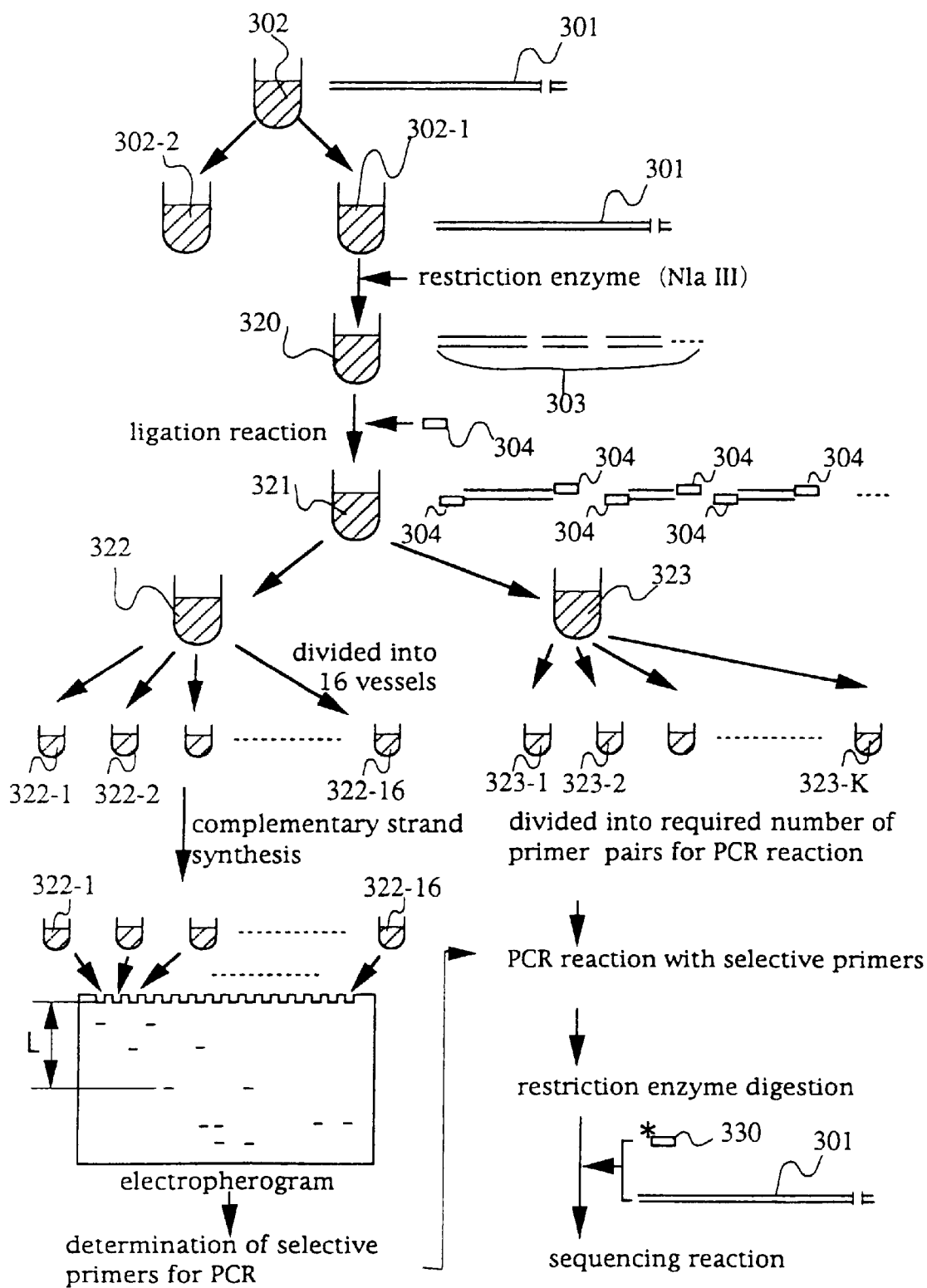
FIG. 12 is a drawing explaining a process for DNA analysis according to the method of the present invention for preparing a sample.

FIG. 12 is a drawing explaining a process for DNA analysis according to the method of the present invention for preparing a sample. Solution 302 containing sample DNA 301 (having several Kb to 10 Kb in length) is divided into two aliquots, which are then taken in first tube 302-1 and second tube 302-2, respectively. Sample DNA charged in the first tube 302-1 is digested with restriction enzyme NlaIII to obtain DNA fragment groups 303. NlaIII recognizes base sequence -CATG- and produces DNA fragments having 3'-terminal base sequence of -CATG(3'). The restriction enzyme employed may be any one of Sau3AI, HhaI, MaeI and others but a 4-base cutter restriction enzyme is preferred since its digestion site appears with high frequency. DNA oligonucleotide 304 is added to solution 320 containing DNA fragment groups 303 to bind DNA oligonucleotide 304 having a known base sequence at least at the 3' end of the digestion site by a restriction enzyme. Poly A tailing using terminal deoxynucleotidyl transferase and ligation is used to bind DNA polynucleotide 304. Herein, the procedure is explained by referring to ligation. Solution 321 containing the ligation reaction products is divided into two aliquots, which are charged in tubes 322 and 323.

Figure 13:
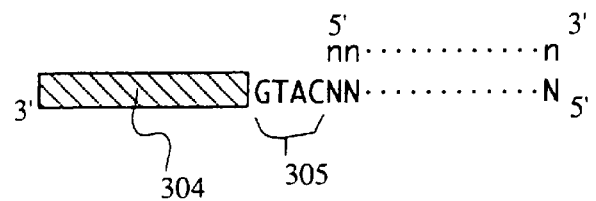
FIG. 13 shows a DNA fragment with which DNA oligonucleotide is ligated.

FIG. 13 shows a DNA fragment to which DNA oligonucleotide is ligated. In FIG. 13, symbols N and n represent nucleotide (any one of A, T, G and C) for constructing the DNA fragment to be sequenced and recognition sequence 305 recognized by NlaIII is -CATG-3'. The 3' terminal site of DNA strand after ligation of DNA oligonucleotide 304 is replaced with, e.g., dideoxynucleotide so that the complementary strand is not further extended. Of course, 3'-OH of the DNA oligonucleotide may be modified with an amino residue or a biotin residue to block the 3'-terminal extension. The reason why the 3'-terminal complementary strand synthesis is blocked in the DNA strand after ligation of DNA oligonucleotide 304 is to prevent the formation of a complementary strand to the anchor portion, where, in complementary strand synthesis using the anchored primer employed, the 3' terminus (portion having a base sequence for discriminating DNA fragments) of the anchored primer is not fully complementary to the DNA fragment. In a strand in which the 3' terminus of the anchored primer completely coincides with the DNA fragment, a part of the anchored primer hybridizes with the other terminus (3' terminus of the synthesized strand). By further extension, a DNA fragment having complementary base sequence to the anchored portion at the 3' terminus thereof is synthesized.

Figure 14A:
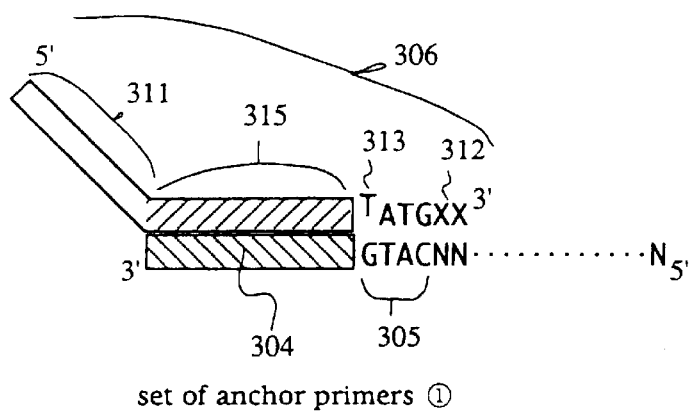
FIG. 14A is a conceptional drawing of a set of anchor primers which hybridize to the terminal DNA strand (single strand) after ligation of a DNA oligonucleotide.
Figure 14B:
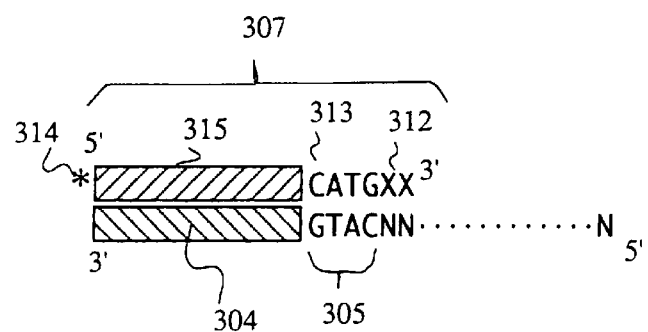
FIG. 14B is a conceptional drawing of a set of primers which hybridize to the terminal DNA strand (single strand) after ligation of DNA oligonucleotide.

FIG. 14A is a conceptional drawing of a set of anchor primers (anchor primer set (1)) which hybridize to the terminal DNA strand (single strand) after ligation of DNA oligonucleotide 304. FIG. 14B is a conceptional drawing of a primer set (2) which hybridize to the terminal DNA strand (single strand) after ligation of DNA oligonucleotide 304.

There are prepared 16 anchor primer set 306 (4 to 256 anchored primers in response to 1 to 4 bases) having complementary portion 315 to DNA oligonucleotide 304 introduced into the DNA fragment and anchor sequence 311 at the 5' terminus thereof and having 3'-terminal discrimination sequence 312 of 2 bases (which may be 1 to 4 bases) shown by XX. The discrimination sequence 312 is a base sequence for selecting a specific DNA fragment from a mixture of DNA fragments. The base sequence of the anchored portion 311 in the anchor primer set 306, or the portion containing the anchored portion 311, is substantially a universal sequence. In this case, as shown by 313 in FIG. 14A, there are prepared 16 anchored primers (anchor primer set (1)) in which the sixth base position at the 3' terminus in anchor primer set 306 (one of the recognition sequence by a restriction enzyme; C in this case) and primer set 307 (primer set (2)) in which C is kept as it is without any replacement. In this embodiment, there is no need to attach any anchor to the primer set (2) as shown in FIG. 14B but for convenience of later confirmation, the primer set (2) is labeled with Texas Red or FITC fluorophore tag 314.

Figure 15:
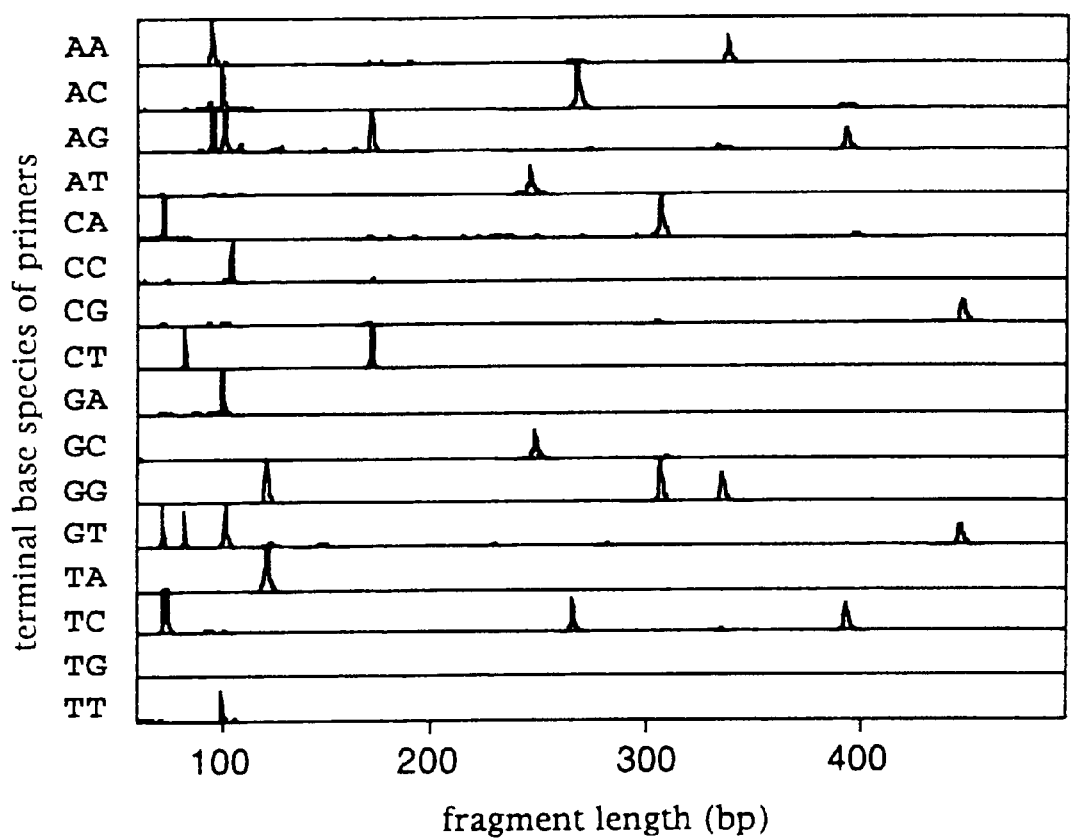
FIG. 15 shows gel electropherograms of the complementary strand synthesis reaction products of the DNA fragment obtained using 16 selective primers.
Figure 16:
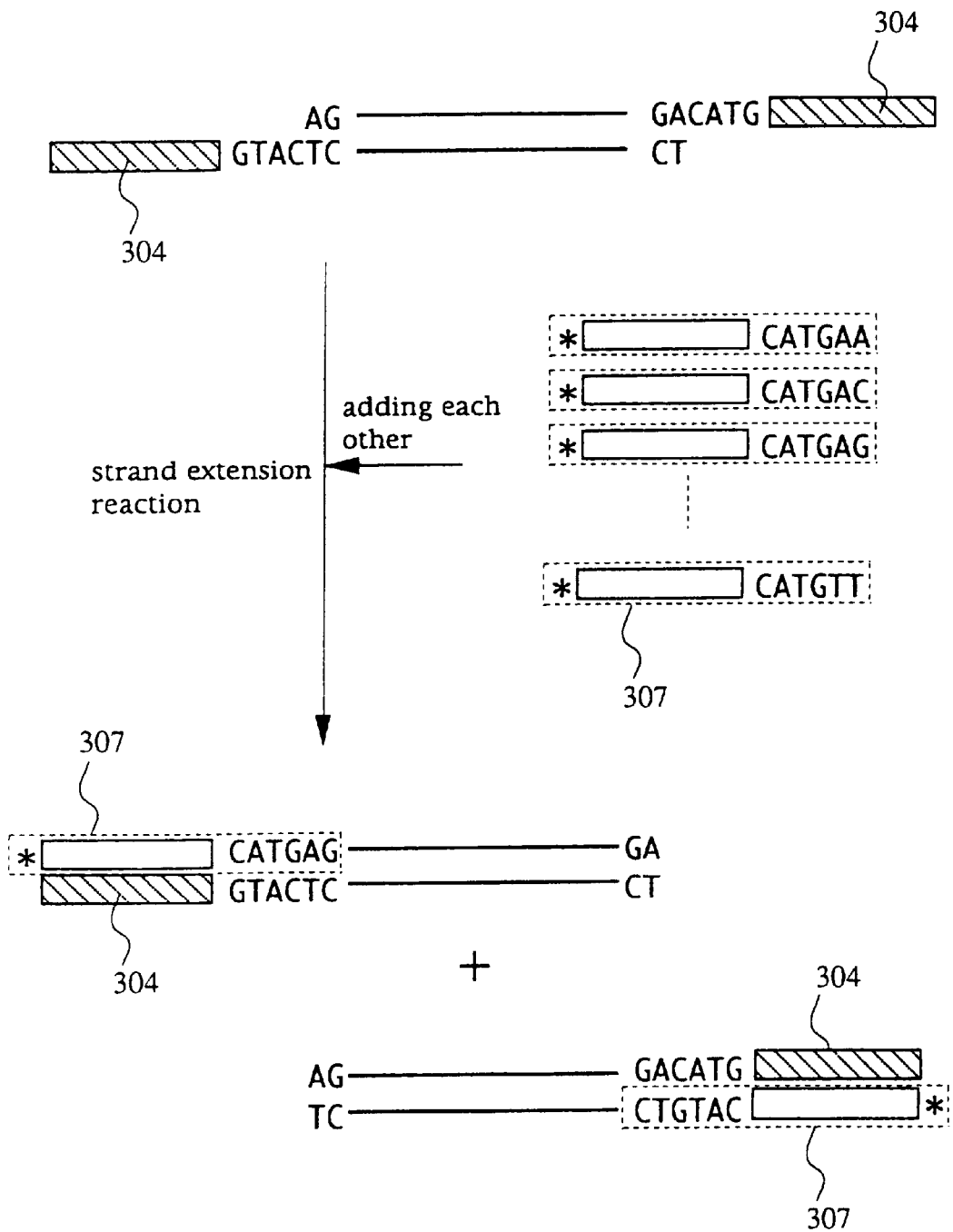
FIG. 16 shows a construction of the detected DNA fragment.

Using the primer set (2) tagged with one fluorophore and the DNA fragment mixture, primer extension reaction is carried out. That is, as shown in FIG. 12, the ligation products-containing solution charged in tube 322 is divided into 16 aliquots, which are charged in 16 tubes named 322-1, 322-2, . . . and 322-16, respectively. Each of the primers (which are different from each other) is added to each tube to perform complementary strand synthesis. That is, a primer of a variable and discrimination sequence 312 is added to each tube. The products of complementary strand synthesis are subjected to gel electrophoresis. FIG. 15 shows gel electropherograms of the complementary strand synthesis reaction products. In the migration patterns, the primer having variable and discrimination sequence 312 and the complementary strand synthesis reaction products from + and − strands in the double stranded DNA appear as a pair at equal distance L from the point when the migration starts. Where the 3-terminal two bases of the primer completely matches the DNA fragment, complementary strand synthesis occurs to produce fluorophore tagged DNA fragment having the same length as that of the DNA fragment. By obtaining the spectra shown in FIG. 15, it is thus appreciated that in the DNA fragment groups there are fragments reflecting the fragment length and the terminal base sequence. FIG. 16 shows a construction of the detected DNA fragment. For example, a DNA fragment having about 400 bp in fragment length appears in the electropherograms obtained using the primer having AG as a discrimination sequence (primer selecting sequence) and the primer having TC as a discrimination sequence (primer selecting sequence). The results reveal that the DNA fragment having a length of about 400 bp and having the respective 3'-terminal base sequences of 3'□ GTACTC . . . 5' and 3'□ GTACAG . . . 5' is contained in the double stranded DNA fragments obtained by digesting sample DNA with a restriction enzyme. Herein, symbols "'" and ". . ." indicate the base sequence of oligonucleotide introduced into the DNA fragments through ligation and the base sequence inherent to the DNA fragments, respectively. The 5'-terminal base sequences following the base sequence 3' GTAC 5' in the recognition base sequence recognized by a restriction enzyme become complementary base sequences to AG and TC, respectively. That is, the results reveal that the DNA fragments shown in FIG. 16 are present in the DNA fragment mixture. In order to remove only the specific DNA fragment, polymerase chain reaction (PCR) may be performed using anchored primers having AG and TC as the terminal base sequence, respectively, to increase the copy number of the specific DNA fragment by several figures as compared to the other DNA fragments.

The base sequence of the thus obtained DNA fragments and the base sequence of sample DNA associated therewith are determined using primers labeled with 4 fluorophore tags, respectively. To sequencing with the existing four fluorophore tagged primers, there is employed anchor primer set 306 (1) in which the primers are anchored at the 5' terminus. That is, the anchored primers are primers having anchor sequence 311 common to universal primers, the primer sequence 315 substantially complementary to DNA oligonucleotide 304 introduced at the 3' terminus of DNA fragments by ligation and common to the anchor primer set 306, a base sequence common partly or wholly to the base sequence recognized by a restriction enzyme, and variable and discriminating sequence 312 of 2 bases at the 3' terminus thereof. The anchor sequence 311 and the common primer sequence 315 may be common in part, but it is required that the length of the common part should be 8-mer or less and the existing known four fluorophore tagged primers cannot hybridize stably, by the primers alone, with the base sequence of the DNA oligonucleotide 304 introduced into the DNA fragments and hence, cannot effect complementary strand synthesis. Furthermore, it is required for stable hybridization that the base sequence of the anchor portion 311 should be 10-mer or more, preferably 15-mer or more.

The primer sequences need to be elaborated at this step. That is, in these anchored primers (1) having a complementary base sequence to DNA oligonucleotide 304 introduced into the DNA fragments and two base discrimination sequence (XX) 312 at the 3' end thereof, one of the 5' terminal bases in the base sequence -CATG- recognized by a restriction enzyme may be changed. In the embodiment shown in FIG. 14A, C in the base sequence -CATG- has been changed to T (which may be A or G in place of T). In this anchored primer, mismatching occurs at the sixth base T313 at the 3' terminus but the anchored primer stably hybridizes to DNA oligonucleotide 304 introduced into the DNA fragment at the terminus to form a complementary strand. The thus formed DNA strand cannot be digested with the restriction enzyme used in this embodiment. When A in the base sequence -CATG- is changed to any one of T, G and C, this anchored primer also causes mismatching at the fifth base position at the 3' end. However, the anchored primer hybridizes stably to DNA oligonucleotide 304 introduced at the terminus of the DNA fragment to form a complementary strand. Likewise, the thus formed DNA strand cannot be digested with the restriction enzyme used in this embodiment. Furthermore there are prepared 16 primers (primer set (2)). These primers lack any anchor sequence as shown in FIG. 14B but are primers having a variable and discriminating sequence (XX) 312. The base sequence of the sixth base position from the two bases at the 3' end is complementary to the base sequence -CATG- and hence, the 5'-terminus may or may not be labeled with fluorophore tag 314.

Based on the results shown in FIG. 15, there is determined a selective primer for PCR necessary for amplification of the DNA fragment longer than 130 bp. As shown in FIG. 12, the solution in tube 323 is divided and charged into vessels corresponding to the number (k) of the combinations for PCR (in the migration patterns, the number of the complementary strand synthesis reaction products is not greater than the number of pairs appearing at an equal distance from the starting point of the migration and equal to the number of the determined selective primers for PCR), i.e., vessels 323-1, 323-2, . . . 323-k. A variable and discriminating primer for PCR is added to each vessel to perform amplification by PCR using a selective primer. For this PCR amplification, the combination of anchors of anchor primer set (1) and primer set (2) is employed. At this stage, DNA fragments having 130 bp or less (150 bp in general) are not subjected to PCR amplification, since the overall base sequence can be determined by linking the respective DNA fragments, as described below.

Figure 17:
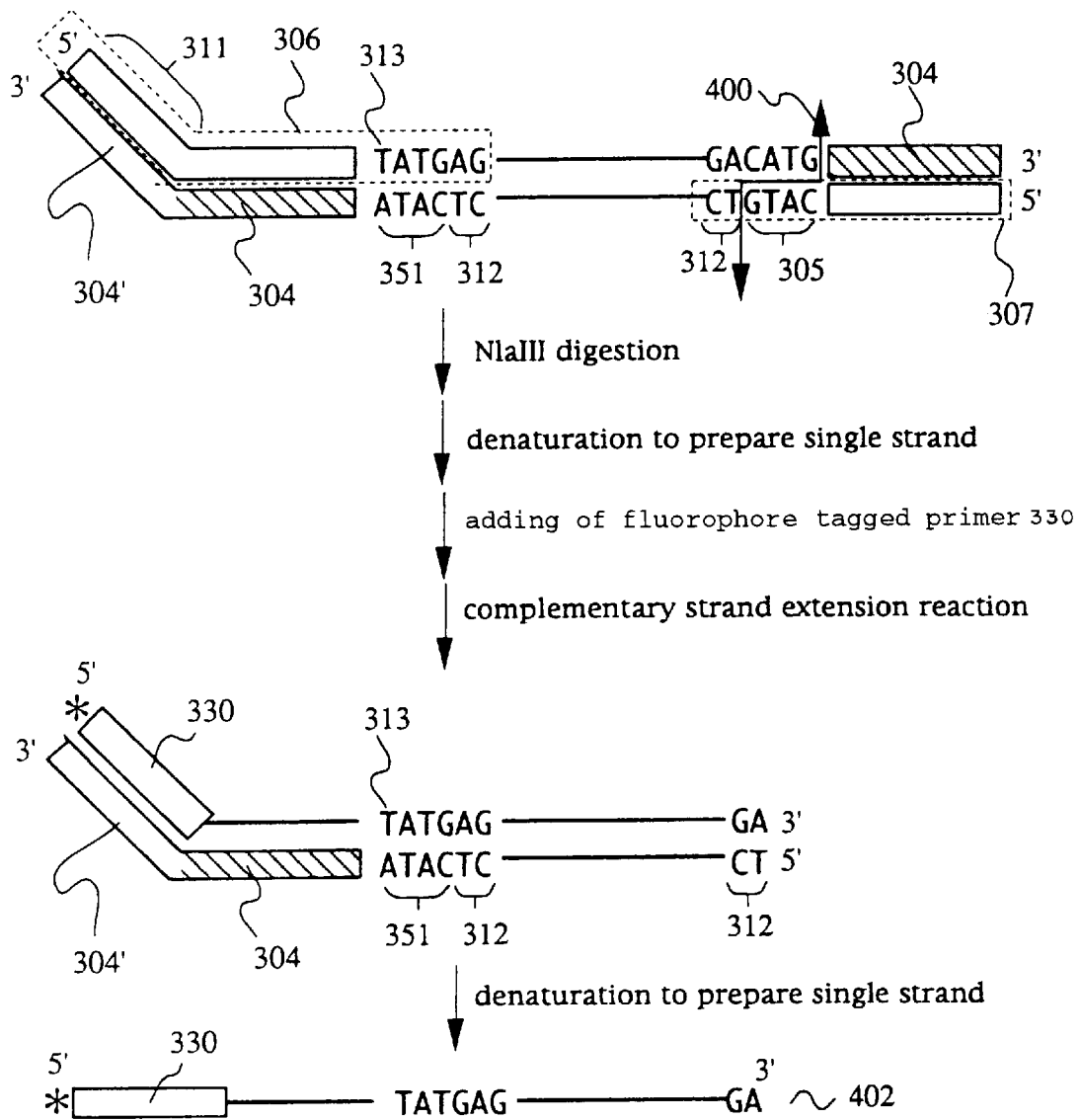
FIG. 17 shows an example of the product obtained by a complementary strand extension reaction (PCR amplification) using anchored primers.

The DNA fragments amplified by PCR are purified by, e.g., dialysis to provide as templates for sequencing. FIG. 17 shows an example of the product obtained by a complementary strand extension reaction (PCR amplification) using anchored primers (1). In FIG. 17, the portion 304' corresponds to the extended portion of DNA oligonucleotide 304. The DNA fragments obtained here are DNA fragments having anchored primers of anchor primer set 306 (anchor primer set (1)) and the primers of primer set 307 (primer set (2)) at the terminus, respectively. When the restriction enzyme previously used is acted on the base sequence portion -CATG- in the portion 305 with the primer of primer set 307, digestion occurs at the cutting site 400, but -CATA- in the portion 351 with the anchor primer of anchor primer set 306, is not digested with the restriction enzyme previously used, since the base sequence portion is different from -CATG-.

As the consequence, when the PCR amplification products are digested with the restriction enzyme and rendered single strands and complementary strand synthesis is then carried out using fluorophore tagged primer 330 (symbol * denotes a fluorophore tag) having the same base sequence as the anchor sequence 311, hybridization to the sample DNA strand occurs to form a further complementary strand extendable DNA fragment (fluorophore tagged primer 402 by complementary strand synthesis). Thereafter, intact sample DNA 301 taken in the second tube 302-2 and the reagent for sequencing (reagent containing ddNTP: dideoxynucleotide triphosphate) are added to perform sequencing. The base sequence of the DNA fragment amplified by PCR is determined from the sequencing reaction using the fluorophore tagged primer 330 and the base sequence with which the DNA fragment should be linked (linking base sequence) is determined by the sequencing reaction using the aforesaid fluorophore tagged primer 402 by complementary strand extension reaction which was previously prepared. That is, the base sequence of the DNA fragment and the contiguous base sequence adjacent to the base sequence can be determined as in Examples 1 to 5.

The DNA fragment shown in FIG. 17 is a DNA fragment having the anchored primer of anchor primer set 306 and the primer of primer set 307 (primer set (2)) at the termini, respectively. The base sequence of sample DNA 301 can be read from the reaction of variable and discriminating primers for PCR (in FIGS. 14A and 14B, primers 307 and 306 having variable and discriminating sequences in the primer set). In the sequencing reaction described above, so-called A, C, G and T termination reactions are carried out using primers having four fluorophore tags of different emission wavelengths. Since a four-color primer can be employed as fluorophore tagged primer 330, handling is simple and convenient. That is, it is advantageous in that it is unnecessary to prepare 16 fluorophore tagged primers (64 primers are required for 4 colors) having a discrimination sequence at the 3' end.

EXAMPLE 8

Figure 18:
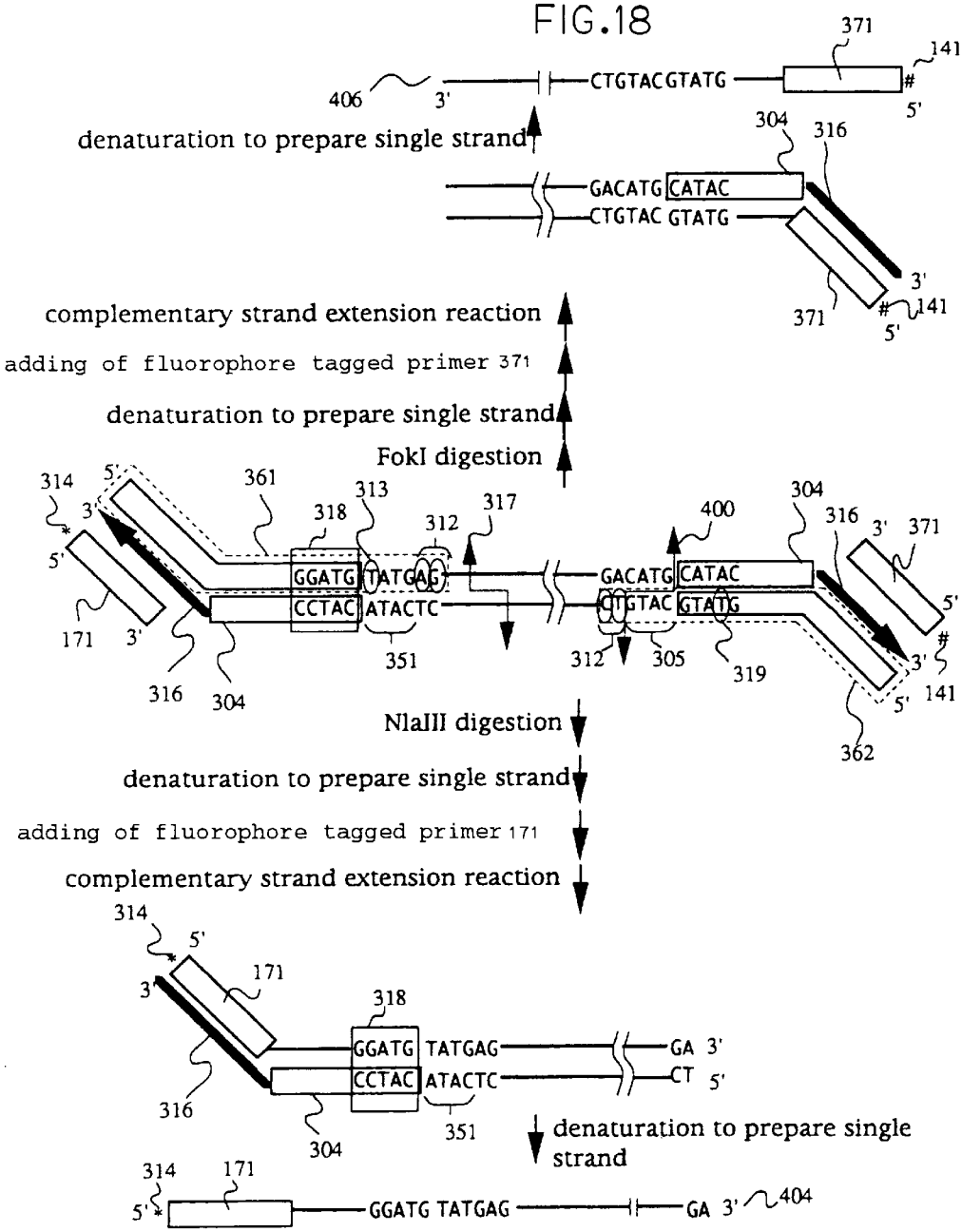
FIG. 18 shows the relationship among anchored primers having a discrimination sequence, tagged primers and DNA fragments.

In this embodiment, the base sequence of double stranded DNA is simultaneously determined from the both 5' and 3' ends. FIG. 18 shows the relationship among anchored primers having a discrimination sequence, tagged primers and DNA fragments. In this embodiment, there are employed fluorophore tagged forward primer 17 (primer used for complementary strand extension synthesis of strand +) and primer 371 (primer used for complementary strand extension synthesis of strand −); Texas Red (314, emission wavelength of 615 nm) and cy-5 (141, emission wavelength of 654 nm) are employed as fluorophore tags. Hereinafter these primers are called primer-a (171, forward primer) and primer-b (371). FIG. 18 shows the relationship between primer-a (171), primer-b (371) and anchor primers (361, 362) and the DNA fragments tailed with the DNA oligonucleotide 304. The base sequence of primer-a (171) is substantially similar to the anchor sequence of anchor primer-a (361) and the base sequence of primer-b (371) is substantially similar to the anchor sequence of anchor primer-b (362). Primer-a and primer-b hybridize partly with the DNA fragments but the hybridization is not stable. Thus, primer-a and primer-b do not cause complementary strand synthesis without any anchor primer. That is, hybridization stably occurs to produce sequencing products only at the DNA strand 316 produced by extension of the anchor primers.

Recognition portion 318 (-GGATG-) by restriction enzyme FokI of class 2A is inserted into the base sequence of DNA oligonucleotide ligated to the DNA fragment. This restriction enzyme FokI is a restriction enzyme for digesting the site 317 of the ninth base position at the 3' terminus from the recognition base sequence part 318 by restriction enzyme and can be used to remove the DNA oligonucleotide ligated to the DNA fragment, as will be later described. Anchor primer-a (361) is not digested with restriction enzyme NlaIII by modifying C, as shown by 313, of the base sequence -CATG- in the recognition base sequence part recognized by the restriction enzyme (recognition base sequence part in which one base has been replaced with another base) into T and thus to -TATG-, but is digested with FokI since the recognition base sequence part -GGATG- by restriction enzyme of class 2A. On the other hand, anchor primer-b (362) is designed to preserve the recognition base sequence part recognized by restriction enzyme -CATG- 305 but by modifying a part (319) of the recognition base sequence part (-GGATG-) recognized by restriction enzyme of class 2A into the sequence part -GTAGT- so that the anchor primer-b (362) is not digested with FokI. That is, the product amplified by PCR using anchor primer-a and anchor primer-b can be digested with restriction enzyme NlaII at one end and with a restriction enzyme of class 2A at another end, i.e., such an elaborative design is made so as to remove the DNA oligonucleotide introduced into the DNA fragment at the termini thereof. Of course, anchor primer-a and anchor primer-b have two base discrimination sequence 312 (AG and TC in FIG. 18) at the 3' end and provide anchor primer sets of 16 primers, respectively.

The procedures will be described below in more detail. A solution containing sample DNA (several Kb to 10 Kb) to be sequence is divided into two aliquots in a manner similar to Example 7. In one aliquot, sample DNA is digested with restriction enzyme NlaII (other 4-base cutter restriction enzyme may also be used). A DNA oligonucleotide having a known base sequence is ligated with the portion digested with the restriction enzyme. The DNA oligonucleotides used herein are helper oligonucleotide 101 having the following base sequence:

5'-GTAAAACGACGGCCAGTGGATGCATG-3', SEQ ID NO: 6 and linker oligonucleotide 102 having the following structure:

3'Bio-CATTTTGCTGCCGGTCACCTAC P-5' SEQ ID NO: 7 which is obtained by introducing biotin (Bio) at the 3' end and having phosphate (P) at the 5' end of an oligonucleotide having the following base sequence:

3'-CATTTTGCTGCCGGTCACCTAC-5' SEQ ID NO: 7.

The base sequence of helper oligonucleotide 101, except for CATG-3' which is the staggered end formed by NlaIII, is complementary to the base sequence of linker oligonucleotide 102, in which biotin (Bio) is introduced to block any further extension. For this purpose, the 3'-terminal OH residue may also be modified with a substance other than biotin (Bio). The DNA strand introduced with the DNA oligonucleotide has the recognition cutting sites with NlaIII around one end and with FokI around another end. The 3' terminus of the introduced linker oligonucleotide 102 is blocked with biotin from further strand extension. Where ligation is not efficient, helper oligonucleotide 101 alone is ligated using a 5'-P-missing linker and then complementary strand is synthesized by polymerase reaction. In this case, the 3' terminus is blocked by introducing dideoxynucleotide into the 3' terminus using terminal nucleotidyl transferase. By this procedure, one should avoid forming a dimer of the primers through ligation thereof with each other so that the base sequences of helper oligonucleotide 101 and linker oligonucleotide 102 can be inserted into the DNA strand with high efficiency. Self ligation of the DNA fragments can be prevented with use of the oligonucleotides in a large excess (100-fold). Anchor primer-a (anchor primer set a) and anchor primer-b (anchor primer set b) commonly hybridize to the introduced DNA oligonucleotides and to the recognition site by NlaIII but in anchor primer-a, the recognition base sequence by NlaIII changes from -CATGNN3' to -TATGNN3'. Turning to anchor primer-b, the recognition base sequence by FokI changes from -GGATGCATGNN, SEQ ID NO: 8, to -GTATGCATGNN, SEQ ID NO: 9. These changes are all point replacement that does not hinder complementary strand synthesis.

Figure 19:
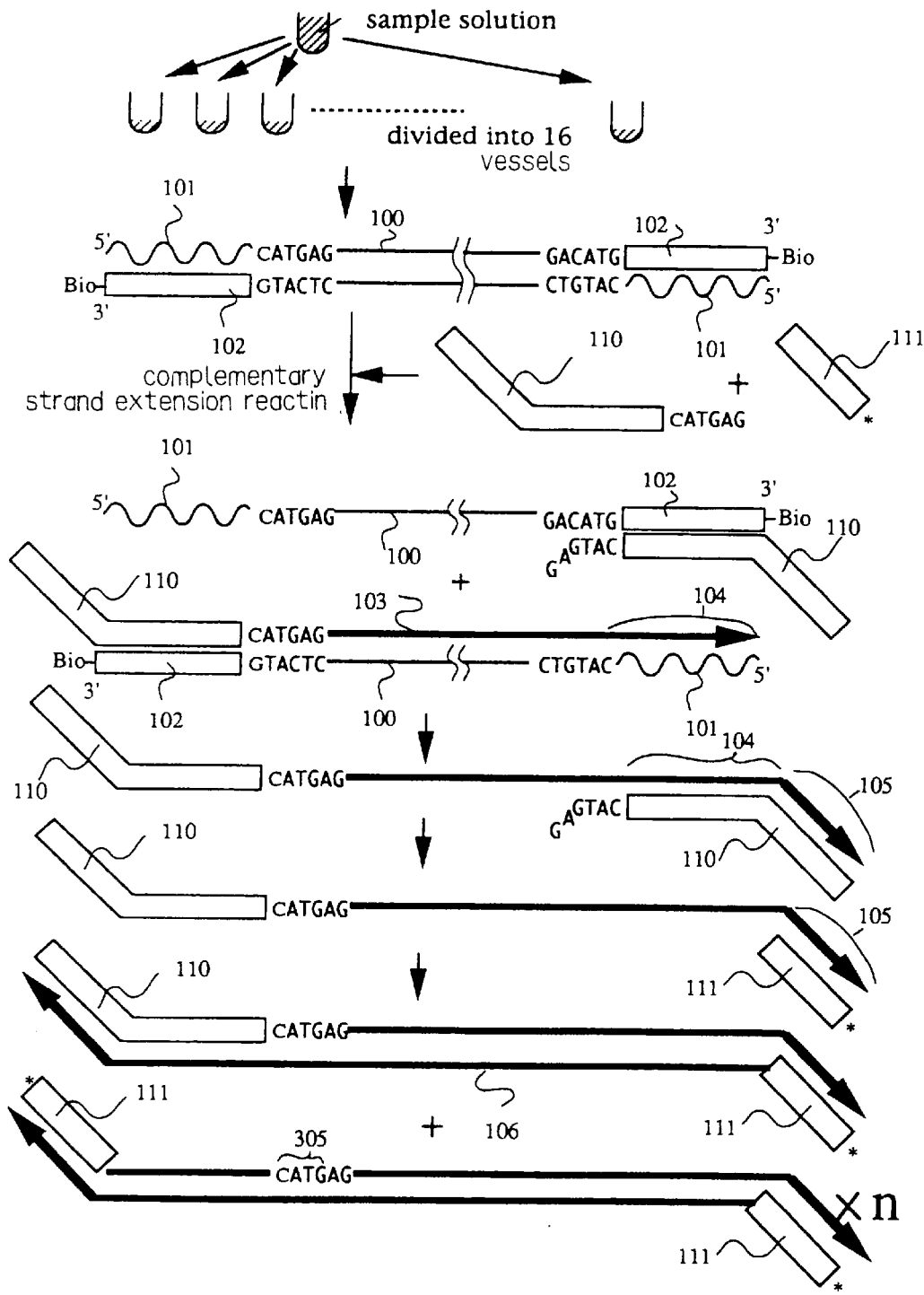
FIG. 19 is a drawing for explaining the method for determining a pair of primers by a small amount of DNA fragments prior to fractionation of the DNA fragments for PCR using anchored primers having a discrimination sequence.

FIG. 19 is a drawing for explaining the method for determining a pair of primers by a small amount of DNA fragments prior to discrimination of the DNA fragments for PCR using anchored primers having a discrimination sequence. In order to determine a pair of the primers for amplifying the DNA fragment mixture by PCR, electropherograms are prepared in a manner similar to Example 7. That is, one sample solution (containing DNA fragment groups digested by a restriction enzyme) of the two aliquots previously divided is further divided into 16 aliquots and charged in vessels, respectively, as shown in FIG. 19. One each of the 16 primers 110 in anchor primer set b is added to each of the vessels and forward primer 111 with a fluorophore tag (*) is further added thereto. Complementary strand synthesis is carried out under cycle sequencing conditions to form complementary strand 106 extended from the forward primer 111. In this embodiment, anchor primer-b is employed but anchor primer-a or even the primer set having no point replacement may be used likewise. In this reaction, anchor primer-b (110) hybridizes to DNA fragment 100; where the 3' terminus completely coincides, complementary strand extension reaction 103 occurs. The strand that does not coincide is not extended at this step. The complementary strand extension is performed to reach the introduced oligonucleotide (helper oligonucleotide 101) portion and as the result, the DNA fragment 104 that hybridizes with helper oligonucleotide 101 is formed at the 3' end of the extended strand. By a heat cycling reaction, this extended complementary strand 103 further forms at the 3' end thereof a DNA fragment having base sequence 105 complementary to the anchor sequence of primer 110. That is, the base sequence portion 105 to which forward primer 111 hybridizes is formed. Forward primer 111 hybridizes to the base sequence portion 105 to form the extended complementary strand 106. Hereinafter the reaction proceeds as in conventional PCR to obtain fluorophore tagged DNA fragment having substantially the same length (longer by the length corresponding to that of the anchor primers at the both ends) as that of the DNA fragment.

In this embodiment, the length of the DNA fragment mixture is determined on the every terminal two base species of the DNA fragments. This embodiment is also effective for PCR amplification of the DNA fragment mixture for the every terminal two base sequences. Where the discrimination sequence is increased from 2 bases to 3 or 4 bases, they may sometimes function as primers even though one base is mismatched. In order to prevent such undesired functioning, for example, where the discrimination sequence is composed of 3 bases, inosine is inserted at the fourth base position (base before the discrimination sequence) at the 3' end of the anchor primer to weaken the terminal binding force. In this case, additional mismatching in the discrimination sequence makes complementary strand synthesis very difficult. This is advantageous for enhancing selectivity.

The fluorophore tagged DNA strands obtained with every 16 anchor primers-b are electrophoresed, whereby the terminal base sequence and fragment length of the DNA strands contained in the mixture can be determined. Using the thus obtained terminal base sequence and length, primers for PCR are selected. As two primers one each is selected from anchor primer-a and anchor primer-b, respectively. Using the two primers (e.g., anchor primer-a (361) and anchor primer-b (362)), amplification is performed by PCR to obtain the DNA fragments having the cutting sites with NlaII around one end and with FokI around another end. After a variety of the DNA fragments obtained are purified by ethanol precipitation, the DNA fragments are dissolved in a buffer solution, respectively. Each solution is divided into two aliquots. Solutions (a) and (b) are obtained with respect to each DNA fragment. The DNA fragments are digested with NlaIII added to solution (a) and with FokI added to solution (b). The DNA fragments digested with NlaIII are denatured to form single strands. Complementary strand synthesis of the single strands is carried out under cycling conditions, using fluorophore tagged primer 171 (forward primer) to form the DNA fragment having a complementary base sequence to the intact sample DNA 301 which hybridizes to the intact sample DNA strand having a further extendable complementary strand (fluorophore tagged primer 404 produced by complementary strand extension reaction). Likewise, the DNA fragments digested with FokI are denatured to form single strands. Complementary strand synthesis of the single strands is carried out under cycling conditions, using fluorophore tagged primer 371 to form the DNA fragment having a complementary base sequence to the intact sample DNA 301 which hybridizes to the intact sample DNA strand having a further extendable complementary strand (fluorophore tagged primer 406 produced by complementary strand extension reaction). In such a manner, DNA fragments 404 and 406 having a further extendable complementary strand which hybridize to the intact sample DNA strand 301 are prepared beforehand.

The two DNA fragments are mixed with each other (the DNA fragments may also be in a separated state until the final step) and sample DNA 301 having full-length intact base sequence is added to the mixture. Reagent for sequencing (containing reagent ddNTP: dideoxynucleotide triphosphate) is further added to the mixture to perform cycle sequencing reaction. This reaction can provide information necessary for sequencing before and after the DNA strands. That is, the base sequence of the DNA fragment amplified by PCR is revealed by the sequencing reaction using fluorophore tagged primers 171 and 371. Using the sequencing reaction with the complementary strand extended fluorophore tagged primers 404 and 406 described above, the base sequence (linking base sequence) with which the DNA fragment should link is revealed. That is, the base sequence of the DNA fragment and the contiguous sequence adjacent thereto can be determined as in Examples 1 to 5.

The base sequence of the DNA fragment and the contiguous sequence adjacent thereto can be determined as in Examples 1 to 5 and Example 7.

In this embodiment, the primers are of two colors (primers labeled wit two fluorophore tags) in response to double stranded DNA (strands + and −). A, C, G and T are fractionated by different migration paths, i.e., electrophoresis is conducted in different migration paths for every terminal base species (Bio/Technology, 9, 648–651 (1991)).

On the other hand, in the case of using a 4 color fluorophore tagged primer (primer labeled with each of four fluorophore tags), the procedure is carried out in a manner similar to Example 7, without mixing solution (a) with solution (b). As stated above, sequencing can be advantageously made from both ends of the double strand, by performing PCR using the primers having different cutting sites at the both ends of the DNA strands. In addition, the present invention is advantageous in that the number of DNA fragments to be sequenced can be minimized since the contiguous sequences to the both ends can be determined simultaneously.

In the foregoing embodiments, it is sufficient that the sample DNA may be of several Kb to 10 Kb. Needless to say, DNA fragments fragmented from the extracted DNA to be sequenced may also be used as DNA samples for the present invention.

What is claimed is:

1. A DNA sequencing method comprising:
    (1) digesting a double stranded sample DNA with a restriction enzyme to form first double stranded DNA fragments;
    (2) forming second double stranded DNA fragments by connecting an oligonucleotide having a known base sequence to the first double stranded DNA fragments at 3' ends thereof;
    (3) performing a complementary strand synthesis using one strand of the second double stranded DNA fragments as a template, and using deoxynucleotides (dNTP), a labeled primer and a DNA polymerase to form a labeled extended primer having a base sequence complementary to the one strand of the second double stranded DNA fragments,
    wherein the labeled primer has, at a side of a 5' end thereof, a first base sequence complementary to at least a part of the base sequence of the oligonucleotide, a second base sequence which is complementary to the base sequence recognized by the restriction enzyme and is connected to at a 3' end of said first base sequence, and has, at a 3' end, a third base sequence which is selected from all possible combinations of 1 to 4 bases selected from the group consisting of A, T, G and C, to discriminate the base sequence of 1 to 4 bases contiguous to the base sequence recognized by the restriction enzyme of the one strand of the second double stranded DNA fragments;
    (4) performing a sequencing reaction using one strand of one of the second double stranded DNA fragments and one strand of the double stranded sample DNA as templates, and using the labeled primer and the labeled extended primer formed in step (3), the DNA polymerase, deoxynucleotides (dNTP), and dideoxynucleotides (ddNTP) as sequencing reagents; and
    (5) subjecting products of the sequencing reaction in step (4) to electrophoresis to determine the base sequence of the one strand of the one of the second double stranded DNA fragments and at least a part of the base sequence of the one strand of the double stranded sample DNA contiguous to a 3' end of the base sequence of the one strand of the one of the second double stranded DNA fragments.

2. A DNA sequencing method according to claim 1, wherein a single stranded DNA fragment having a part of a base sequence of the one strand of double stranded sample DNA is used in step (4) instead of the one strand of the double stranded sample DNA, and a base sequence of the single stranded DNA fragment includes a first base sequence being same as a base sequence of one strand of one of the first double stranded DNA fragments and a second base sequence contiguous to the first base sequence.

3. A DNA sequencing method according to claim 1, wherein said labeled primer is labeled with a fluorophore.

4. A DNA sequencing method according to claim 1, wherein said step (3) is repeated a plurality of times by varying temperature conditions.

5. A DNA sequencing method according to claim 1, wherein said step (3) is repeated a plurality of times in a thermal cycle to amplify the labeled extended primer.

6. A DNA sequencing method according to claim 1, wherein the DNA polymerase used in steps (3) and (4) is a thermostable DNA polymerase.

7. A DNA sequencing method according to claim 1, wherein said oligonucleotide comprises a same base species selected from the groups consisting of A, G, C and T.

8. A DNA sequencing method comprising:
    (1) digesting a double stranded sample DNA with a first restriction enzyme to form first double stranded DNA fragments;
    (2) performing complementary strand synthesis using one strand of the first double stranded DNA fragments as a template, and using deoxynucleotides (dNTP), a labeled primer and a DNA polymerase to form a second double stranded DNA fragment, and then decomposing the second double stranded DNA fragment by a DNA polymerase having 3'-exonuclease activity and connecting a fluorophore tagged deoxynucleotide (dNTP) at a 3' end of the second double stranded DNA fragment decomposed by the DNA polymerase to form a third double stranded DNA fragment;
    (3) digesting the third double stranded DNA fragment formed in step (2) with a second restriction enzyme different from the first restriction enzyme and denaturing the products of digesting to form a fluorophore tagged primer having a label at a 3' end thereof;
    (4) performing a sequencing reaction using one strand of the double stranded sample DNA as a template, and using the fluorophore tagged primer formed in step (3), the DNA polymerase, deoxynucleotides (dNTP), and dideoxynucleotides (ddNTP) as sequencing reagents; and
    (5) subjecting products of the sequencing reaction in step (4) to electrophoresis to determine at least a part of the base sequence of one strand of the first double stranded sample DNA contiguous to a 3' end of the base sequence complementary to the fluorophore tagged primer.

9. A DNA sequencing method according to claim 8, wherein a single stranded DNA fragment having a part of a base sequence of the one strand of double stranded sample DNA is used in step (4) instead of the one strand of the double stranded sample DNA, and a base sequence of the single stranded DNA fragment includes a first base sequence being same as a base sequence of one strand of one of the first double stranded DNA fragments and a second base sequence contiguous to the first base sequence.

10. A DNA sequencing method comprising:
    (1) digesting a double stranded sample DNA with a restriction enzyme to form double stranded DNA fragments;

(2) performing a complementary strand synthesis using one strand of the double stranded DNA fragments as template, and using deoxynucleotides (dNTP), a first primer and a DNA polymerase to form a second primer having a base sequence complementary to the one strand of one of the double stranded DNA fragments;

(3) performing a sequencing reaction using the one of the double stranded DNA fragments as a template, and using the second primer formed in step (2), DNA polymerase, deoxynucleotides (dNTP) and dideoxynucleotides (ddNTP) as sequencing reagents, to form fragments each having fluorophore label at a 3' end; and (4) digesting products of the sequencing reaction in step (3) with the restriction enzyme to form a third primer; and (5) subjecting the digested products in step (4) to electrophoresis to determine at least a part of the base sequence of the one strand of the double stranded sample DNA contiguous to a 3' end of the base sequence of the one strand of the one of the double stranded DNA fragments.

11. A DNA sequencing method according to claim 10, wherein a single stranded DNA fragment having a part of a base sequence of the one strand of double stranded sample DNA is used in step (3) instead of the one strand of the double stranded sample DNA, and a base sequence of the single stranded DNA fragment includes a first base sequence being same as a base sequence of one strand of one of the double stranded DNA fragments and a second base sequence contiguous to the first base sequence.

12. A DNA sequencing method comprising:

(1) digesting a double stranded sample DNA with a restriction enzyme to form first double stranded DNA fragments;

(2) forming second double stranded DNA fragments by connecting an oligonucleotide having a known base sequence to the first double stranded DNA fragments at 3' ends thereof;

(3) performing a complementary strand synthesis using one strand of the second double stranded DNA fragments as a template, and using deoxynucleotides (dNTP) a labeled primer and a DNA polymerase to form a labeled extended primer having a base sequence complementary to the one strand of one of the second double stranded DNA fragments, wherein the labeled primer has, at a side of a 5' end thereof, a first base sequence complementary to at least a part of the base sequence of the oligonucleotide, a second base sequence which is complementary to the base sequence recognized by the restriction enzyme and is connected to at a 3' end of said first base sequence, and has, at a 3' end, a third base sequence which is selected from possible combinations of 1 to 4 bases selected from the group consisting of A, T, G and C, to discriminate the base sequence of 1 to 4 bases contiguous to the base sequence recognized by the restriction enzyme of the one strand of the one of the second double stranded DNA fragments:

(4) performing a sequencing reaction using one strand of the double stranded sample DNA as a template, and using the extended labeled primer formed in step (3), the DNA polymerase, deoxynucleotides (dNTP) and Di deoxynucleotides (ddNTP) as sequencing reagents; and (5) subjecting products of the sequencing reaction in step (4) to electrophoresis to determine at least a part of the base sequence of the one strand of the first double stranded sample DNA contiguous to a 31 end of the base sequence of the one strand of the one of the second double stranded DNA fragments.

13. A DNA sequencing method according to claim 12, wherein a single stranded DNA fragment having a part of a base sequence of the one strand of double stranded sample DNA is used in step (4) instead of the one strand of the double stranded sample DNA, and a base sequence of the single stranded DNA fragment includes a first base sequence being same as a base sequence of one strand of one of the first double stranded DNA fragments and a second base sequence contiguous to the first base sequence.

14. A DNA sequencing method comprising:

(1) digesting a double stranded sample DNA with a restriction enzyme to form double stranded DNA fragments;

(2) performing an complementary strand synthesis using one strand of the double stranded DNA fragments as a template, and using deoxynucleotides (dNTP), a fluorophore tagged primer and a DNA polymerase to form a extended fluorophore tagged primer having a base sequence complementary to the one strand of one of the double stranded DNA fragments;

(3) performing a sequencing reaction using one strand of the double stranded sample DNA as a template, and using the extended fluorophore tagged primer formed in step (2), the DNA polymerase, deoxynucleotides (dNTP), and dideoxynucleotides (ddNTP) as sequencing reagents; and (4) subjecting products of the sequencing reaction in step (3) to electrophoresis to determine at least a part of the base sequence of the one strand of the double stranded sample DNA contiguous to a 3' end of the base sequence of the one strand of the one of the double stranded DNA fragments.

15. A DNA sequencing method according to claim 14, wherein a single stranded DNA fragment having a part of a base sequence of the one strand of double stranded sample DNA is used in step (3) instead of the one strand of the double stranded sample DNA, and a base sequence of the single stranded DNA fragment includes a first base sequence being same as a base sequence of one strand of one of the double stranded DNA fragments and a second base sequence contiguous to the first base sequence.

16. A DNA sequencing method comprising:

(1) digesting a double stranded sample DNA with a restriction enzyme to form double stranded DNA fragments;

(2) performing a sequencing reaction using one strand of the double stranded sample DNA and one strand of the double stranded DNA fragments as templates, and using a first primer labeled with a fluorophore which selectively hybridizes with one strand of the double stranded DNA fragments, a second primer labeled with a fluorophore, a DNA polymerase, deoxynucleotides (dNTP), and dideoxynucleotides (ddNTP) as sequencing reagents, wherein said second primer is formed by performing a complementary strand synthesis using the one strand of the second double stranded DNA fragments as a template, and using the first primer; and (3) subjecting products of the sequencing reaction in step (2) to electrophoresis to determine at least a part of the base sequence of the one strand of the double stranded sample DNA contiguous to a 3' end of the base sequence of the one strand of one of the double stranded DNA fragments.

17. A DNA sequencing method according to claim 16, wherein a single stranded DNA fragment having a part of a base sequence of the one strand of double stranded sample DNA is used in step (2) instead of the one strand of the double stranded sample DNA, and a base sequence of the single stranded DNA fragment includes a first base sequence being same as a base sequence of one strand of one of the double stranded DNA fragments and a second base sequence contiguous to the first base sequence.

18. A DNA sequencing method comprising:
(1) digesting a double stranded sample DNA with a restriction enzyme to form first double stranded DNA fragments;
(2) forming second double stranded DNA fragments by connecting an oligonucleotide having a known base sequence to the first double stranded DNA fragments at 3' ends thereof;
(3) performing a complementary strand synthesis using one strand of the second double stranded DNA fragments as a template, and using deoxynucleotides (dNTP), labeled primers and a DNA polymerase, and classifying the second double stranded DNA fragments into $4^1$ to $4^4$ groups of third double stranded DNA fragments by the difference of the base sequence of 1 to 4 bases contiguous to the base sequence recognized by the restriction enzyme of the one strand of the second double stranded DNA fragments by whether forming stable double strands by the complementary strand synthesis using the one strand of the second double stranded DNA fragments, and using the labeled primers, by measuring the length of the complementary strand synthesis products by electrophoresis, and selecting a fluorophore tagged primer used for a sequencing reaction,
wherein each of the labeled primers has, at a side of a 5' end, a first base sequence complementary to at least a part of the base sequence of the oligonucleotide, a second base sequence which is complementary to the base sequence recognized by the restriction enzyme and is connected to at a 3' end of said first base sequence, and has, at a 3' end, one of third base sequences which includes 1 to 4 bases selected from the group consisting of A, T, G and C, to discriminate the base sequence of 1 to 4 bases contiguous to the base sequence recognized by the restriction enzyme of the one strand of the second double stranded DNA fragments, and the third base sequences includes all possible $4^1$ to $4^4$ combinations of 1 to 4 bases out of A, C, G and T;
(4) subjecting the third double stranded DNA fragments to electrophoresis to fractionate the third double stranded DNA fragments depending upon fragment lengths;
(5) performing a complementary strand synthesis using the fractionated one strand of the third double stranded DNA fragments as a template, and using deoxynucleotides (dNTP), the selected fluorophore tagged primer in step (3) and the DNA polymerase to form complementary strands;
(6) performing a sequencing reaction using the fractionated one strand of one of the third double stranded DNA fragments in step (4) and one strand of the double stranded sample DNA as templates, and using the selected fluorophore tagged primer in step (3), the complementary strands formed in step (5), the DNA polymerase, deoxynucleotides (dNTP), and dideoxynucleotides (ddNTP) as sequencing reagents; and
(7) subjecting products of the sequencing reaction in step (6) to electrophoresis to determine the base sequence of the fractionated one strand of the one of the third double stranded DNA fragments and at least a part of the base sequence of the one strand of the double stranded sample DNA contiguous to a 3' end of the base sequence of the fractionated one strand of the one of the third double stranded DNA fragments.

19. A DNA sequencing method according to claim 18, wherein a single stranded DNA fragment having a part of a base sequence of the one strand of double stranded sample DNA is used in step (6) instead of the one strand of the double stranded sample DNA, and a base sequence of the single stranded DNA fragment includes a first base sequence being same as a base sequence of one strand of one of the first double stranded DNA fragments and a second base sequence contiguous to the first base sequence.

20. A DNA sequencing method comprising:
(1) digesting a double stranded sample DNA with a restriction enzyme to form double stranded DNA fragments;
(2) performing a complementary strand synthesis using one strand of the double stranded DNA fragments as a template,
and using deoxynucleotides (dNTP), a primer and a DNA polymerase to form a first single stranded DNA fragment;
(3) performing a sequencing reaction using one strand of the double stranded sample DNA as a template, and using the first single stranded DNA fragment, the DNA polymerase, deoxynucleotides (dNTP), and dideoxynucleotides (ddNTP) as sequencing reagents; and
(4) subjecting products of the sequencing reaction in step (3) to electrophoresis to determine at least a part of the base sequence of the one strand of the double stranded sample DNA contiguous to a 3' end of the base sequence of the one strand of the one of the double stranded DNA fragments.

21. A DNA sequencing method according to claim 20, wherein a single stranded DNA fragment having a part of a base sequence of the one strand of double stranded sample DNA is used in step (3) instead of the one strand of the double stranded sample DNA, and a base sequence of the single stranded DNA fragment includes a first base sequence being same as a base sequence of one strand of one of the double stranded DNA fragments and a second base sequence contiguous to the first base sequence.

22. A DNA sequencing method comprising:
(1) digesting a double stranded sample DNA with a restriction enzyme to form double stranded DNA fragments;
(2) performing a sequencing reaction using one strand of the double stranded DNA fragments and one strand of the double stranded sample DNA as templates, and using a first primer which selectively hybridizes with the one strand of one of the double stranded DNA fragments, a second primer which selectively hybridizes with a part of the one strand of the double stranded sample DNA, a DNA polymerase, deoxynucleotides (dNTP) and dideoxynucleotides (ddNTP) as sequencing reagents;
wherein said second primer is formed by performing a complementary strand synthesis using the one strand of the second double stranded DNA fragments as a template, and using the first primer: and (3) subjecting products of the sequencing reaction in step (2) to electrophoresis to simultaneously determine the base sequence of the one strand of the one of the double stranded DNA fragments and at least a part of the base sequence of the one strand of the double stranded sample DNA contiguous to a 3' end of the base sequence of the one strand of the one of the double stranded DNA fragments.

23. A DNA sequencing method according to claim 22, wherein a single stranded DNA fragment having a part of a base sequence of the one strand of double stranded sample DNA is used in step (2) instead of the one strand of the double stranded sample DNA, and a base sequence of the single stranded DNA fragment includes a first base sequence being same as a base sequence of one strand of one of the double stranded DNA fragments and a second base sequence contiguous to the first base sequence.

24. A DNA sequencing method comprising:
(1) digesting a double stranded sample DNA with a restriction enzyme to form first double stranded DNA fragments;
(2) forming second double stranded DNA fragments by connecting an oligonucleotide having a known base sequence to the first double stranded DNA fragments at 3' ends thereof;
(3) performing a sequencing reaction using one strand one of the second double stranded DNA fragments and one strand of the double stranded sample DNA as templates, and using a labeled primer,
wherein the labeled primer has, at a side of a 5' end thereof, a first base sequence complementary to at least a part of the base sequence of the oligonucleotide, a second base sequence which is complementary to the base sequence recognized by the restriction enzyme and is connected to at a 3' end of said first base sequence, and has, at a 3' end, a third base sequence which has an arbitrary known base sequence of 1 to 4 bases selected from the group consisting of A, T, G and C, to discriminate the base sequence of 1 to 4 bases contiguous to the base sequence recognized by the restriction enzyme of one strand of the one of the second double stranded DNA fragments; and
(4) subjecting products of the sequencing reaction in step (3) to electrophoresis to simultaneously determine the base sequence of the one strand of the one of the double stranded DNA fragments and at least a part of the base sequence of the one strand of the double stranded sample DNA contiguous to a 3' end of the base sequence of the one strand of the one of the double stranded DNA fragments.

25. A DNA sequencing method comprising:
(1) performing a complementary strand synthesis using one strand of double stranded DNA fragments formed by digesting a double stranded sample DNA with a restriction enzyme, as templates, and using deoxynucleotides (dNTP), a primer and a polymerase to form an extended primer having a base sequence complementary to the base sequence of the one strand of double stranded DNA fragments,
wherein the primer has, at a side of a 3' end thereof, a base sequence complementary to a part of the base sequence of the one strand of double stranded DNA fragments;
(2) performing a sequencing reaction using the one strand of double stranded DNA fragments and one strand of the double stranded sample DNA as templates, and using the primer, the extended primer formed in step (1), the DNA polymerase, deoxynucleotides (dNTP), and dideoxynucleotides (ddNTP) as sequencing reagents; and
(3) subjecting products of the sequencing reaction in step (2) to electrophoresis to determine the base sequence of the one strand of one of the double stranded DNA fragments and at least a part of the base sequence of the one strand of the double stranded sample DNA contiguous to a 3' end of the base sequence of the one strand of the one of the double stranded DNA fragments.

26. A DNA sequencing method according to claim 25, wherein a single stranded DNA fragment having a part of a base sequence of the one strand of double stranded sample DNA is used in step (2) instead of the one strand of the double stranded sample DNA, and a base sequence of the single stranded DNA fragment includes a first base sequence being same as a base sequence of one strand of one of the double stranded DNA fragments and a second base sequence contiguous to the first base sequence.

27. A method for preparing a sample which comprises:
(1) digesting a double stranded sample DNA with a first restriction enzyme to form first double stranded DNA fragments;
(2) connecting an oligonucleotide having a known base sequence to the first double stranded DNA fragments at 3' ends thereof to form second double stranded DNA fragments;
(3) performing a complementary strand synthesis using one strand of the second double stranded DNA fragments as template, and using a anchor primer, to form a single stranded DNA,
wherein the anchor primer has, at side of a 5' end thereof, an anchor base sequence which has a known base sequence having at least 8 bases and does not hybridize with one strand of the double stranded sample DNA, a first base sequence which is connected to a 3' end of the anchor base sequence and is complementary to the base sequence of the oligonucleotide, a second base sequence which is complementary to the base sequence recognized by the restriction enzyme and is connected to at a 3' end of the first base sequence, and has, at a 3' end, a third base sequence which has an arbitrary known base sequence of 1 to 4 bases selected from the group consisting of A, T, G and C, to discriminate the base sequence of 1 to 4 bases contiguous to the base sequence recognized by the restriction enzyme of the one strand of the second double stranded DNA fragments; and
(4) performing complementary strand synthesis using the one strand of the double stranded sample DNA and the single stranded DNA formed in step (3) as templates, and using a fluorophore tagged primer having the same base sequence of the anchor base sequence, to form a fluorophore labeled extended primer which hybridizes with the sample DNA.

28. A method for preparing a sample which comprises:
(1) digesting a double stranded sample DNA with a first restriction enzyme to form first double stranded DNA fragments;
(2) connecting an oligonucleotide having a known base sequence to the first double stranded DNA fragment at 3' ends thereof to form second double stranded DNA fragments; and
(3) fractionating one strand of the second double stranded DNA fragments depending upon 1 to 4 bases sequences contiguous to the base sequence recognized by the restriction enzyme and amplifying the one strand of the second double stranded DNA fragments, by PCR, using an anchor primer and a primer, wherein the anchor primer has, at a side of a 5' end thereof, an anchor base sequence which has a known base sequence having at least 8 bases and does not hybridize with one of the second double stranded DNA fragments, a first base sequence which is connected to a 3' end of the anchor base sequence and is complementary to the base sequence of the oligonucleotide, a second base sequence which is complementary to the base sequence recognized by the restriction enzyme and is connected to at a 3' end of the first base sequence, and has, at a 3' end, a third base sequence which has an arbitrary base sequence of 1 to 4 bases selected from the group consisting of A, T, G and C, to discriminate the base sequence of 1 to 4 bases contiguous to the base sequence recognized by the restriction enzyme of the one strand of the second double stranded DNA fragments, and wherein the primer has the same base sequence as the anchor base sequence.

29. A method for preparing a sample which comprises:
   (1) digesting a double stranded sample DNA with a first restriction enzyme to form first double stranded DNA fragments; and
   (2) performing complementary strand synthesis using one strand of the double stranded DNA fragments as a template, and using a first primer and a second primer, wherein the first primer has, at a side of a 5' end thereof, the recognition base sequence recognized by the first restriction enzyme, and has, at a 3' end, an arbitrary base sequence of 1 to 4 bases selected from the group consisting of A, T, G and C, to discriminate the base sequence of 1 to 4 bases contiguous to the base sequence recognized by the first restriction enzyme of the one strand of the double stranded DNA fragments, and wherein the second primer has the same base sequence as the first primer except for a part of bases in the recognition base sequence recognized by the first restriction enzyme, the part of bases is replaced with another base species not to be digested with the first restriction enzyme, to synthesize a double stranded DNA having, at one end, the recognition base sequence recognized by the first restriction enzyme, and having, at another end, a recognition base sequence recognized by a second restriction enzyme different from the first restriction enzyme.

30. A method for preparing a sample according to claim 29,
   wherein one side of the end of the double stranded DNA is digested with the first restriction enzyme to prepare a first template DNA for determining the base sequence of one strand of the double stranded sample DNA, and another side of the end of the double stranded DNA is digested with the second restriction enzyme to prepare a second template DNA for determining the base sequence of another strand of the double stranded sample DNA.

31. A method for preparing a sample according to claim 29,
   wherein the second restriction enzyme is a class 2A restriction enzyme, and the first restriction enzyme is a class II restriction enzyme.

32. A method for sequencing which comprises:
   (1) digesting a double stranded sample DNA with a restriction enzyme to form double stranded DNA fragments;
   (2) connecting an oligonucleotide having a known base sequence to the double stranded DNA fragments at 3' ends thereof;
   (3) amplifying a specific double stranded DNA fragment from the DNA fragments obtained in step (2), by PCR using an anchor primer and a primer, wherein the anchor primer has, at a side of a 5' end thereof, an anchor base sequence which has a known base sequence having at least 8 bases and does not hybridize with one strand of the double stranded sample DNA, a first base sequence which is connected to a 3' end of the anchor base sequence and is complementary to the base sequence of the oligonucleotide, a second base sequence which has the same base sequence as base sequence complementary to the base sequence recognized by the restriction enzyme except for a part of bases in the recognition base sequence recognized by the restriction enzyme, and is connected to at a 3' end of the first base sequence, and has, at a 3' end, a third base sequence which has an arbitrary base sequence of 1 to 4 bases selected from the group consisting of A, T, G and C, to discriminate the base sequence of 1 to 4 bases contiguous to the base sequence recognized by the restriction enzyme of the one strand of the specific double stranded DNA fragment, and wherein the primer has the base sequence recognized by the restriction enzyme and can be digested with the restriction enzyme, and wherein, in the anchor primer, the part of bases of the second base sequence is replaced with another base species not to be digested with the restriction enzyme;

(4) digesting at a side of the one end of the amplified specific double stranded DNA fragment in step (3) with the restriction enzyme to form a digested specific double stranded DNA fragment;
   (5) performing a complementary strand synthesis using one strand of the digested specific double stranded DNA fragment in step (4) as a template, and using a fluorophore tagged primer, to obtain a extended fluorophore tagged primer by the complementary strand extension synthesis, wherein the fluorophore tagged primer has the same base sequence as the anchor base sequence; and (6) performing a sequencing reaction using one strand of the digested specific double stranded DNA fragment in step (4) and the one strand of the double stranded sample DNA as templates, and using a fluorophore tagged primer and the extended fluorophore tagged primer.

33. A DNA method for sequencing according to claim 32, wherein said fluorophore tagged primer has substantially the same base sequence as the anchor base sequence.

34. A DNA sequencing method which comprises:
   (1) digesting a double stranded sample DNA with a restriction enzyme to form double stranded DNA fragments;
   (2) connecting an oligonucleotide having a known base sequence to the double stranded DNA fragments at 3' ends thereof;
   (3) amplifying a specific double stranded DNA fragment from the DNA fragments obtained in step (2), by PCR using an anchor primer and a primer, wherein the anchor primer has, at a side of a 5' end thereof, an anchor base sequence which has a known base sequence having at least 8 bases and does not hybridize with one strand of the double strand of sample DNA, a first base sequence which is connected to a 3' end of the anchor base sequence and is complementary to the base sequence of the oligonucleotide, a second base sequence which has the same base sequence as base sequence complementary to the base sequence recognized by the restriction enzyme except for a part of bases in the recognition base sequence recognized by the restriction enzyme, and is connected to at a 3' end of the first base sequence, and has, at a 3' end, a third base sequence which has an arbitrary base sequence of 1 to 4 bases selected from the group consisting of A, T, G and C, to discriminate the base sequence of 1 to 4 bases contiguous to the base sequence recognized by the restriction enzyme of the one strand of the specific double stranded DNA fragment, and wherein the primer has the base sequence recognized by the restriction enzyme and can be digested with the restriction enzyme, and wherein, in the anchor primer, the part of bases of the second base sequence is replaced with another base species not to be digested with the restriction enzyme;

(4) digesting at a side of the one end of the amplified specific double stranded DNA fragment in step (3) with the restriction enzyme to form a digested specific double stranded DNA fragment; and (5) performing a sequencing reaction using one strand of the digested specific double stranded DNA fragment in step (4) and the one strand of the double stranded sample DNA as templates, and using a fluorophore tagged primer having the same base sequence as the anchor base sequence which does not hybridize with one strand of the double stranded sample DNA, to determine the base sequence of the one strand of the digested specific double stranded DNA fragment and base sequence of the one strand of the double stranded sample DNA in the portion contiguous to the base sequence of the one strand of the specific double stranded DNA fragment.

35. A DNA sequencing method according to claim 34, wherein said fluorophore tagged primer has substantially the same base sequence as the anchor base sequence.

36. A DNA sequencing method which comprises:

(1) digesting a double stranded sample DNA with a restriction enzyme to form double stranded DNA fragments;

(2) connecting an oligonucleotide having a known base sequence to the double stranded DNA fragments at 3' ends thereof; and (3) amplifying a specific double stranded DNA fragment from the DNA fragments obtained in step (2), by PCR using an anchor primer and a primer, wherein the anchor primer has, at a side of a 5' end thereof, an anchor base sequence which has a known base sequence having at least 8 bases and does not hybridize with one strand of the double stranded sample DNA, a first base sequence which is connected to a 3' end of the anchor base sequence and is complementary to the base sequence of the oligonucleotide, a second base sequence which has the same base sequence as base sequence complementary to the base sequence recognized by the restriction enzyme except for a part of bases in the recognition base sequence recognized by the restriction enzyme, and is connected to at a 3' end of the first base sequence, and has, at a 3' end, a third base sequence which has an arbitrary base sequence of 1 to 4 bases selected from the group consisting of A, T, G and C, to discriminate the base sequence of 1 to 4 bases contiguous to the base sequence recognized by the restriction enzyme of the one strand of the amplified specific double stranded DNA fragment, and wherein the primer has the base sequence recognized by the restriction enzyme and can be digested with the restriction enzyme, and wherein, in the anchor primer, the part of bases of the second base sequence is replaced with another base species not to be digested with the restriction enzyme, whereby a base sequence of one strand of the amplified specific double stranded DNA fragment is determined.

37. A DNA sequencing method which comprises:

(1) digesting a double stranded sample DNA with a first restriction enzyme to form double stranded DNA fragments;

(2) connecting an oligonucleotide having a known base sequence and a recognition base sequence recognized by a second restriction enzyme to the DNA fragments at 3' ends thereof;

(3) amplifying a specific double stranded DNA fragment from the DNA fragments obtained in step (2), by PCR, using a first anchor primer and a second anchor primer, wherein the first anchor primer has, at side of a 5' end thereof, a first anchor base sequence having at least 8 bases and which has a known base sequence does not hybridize with one strand of the double stranded sample DNA, a first base sequence which is connected to a 3' end of the first anchor base sequence and is complementary to the base sequence of the oligonucleotide, a second base sequence which has the same base sequence as a base sequence complementary to the base sequence recognized by the first restriction enzyme except for a part of bases in the recognition base sequence recognized by the first restriction enzyme, and is connected to at a 3' end of the first base sequence, and has, at a 3' end, a third base sequence which has a first arbitrary base sequence of 1 to 4 bases selected from the croup consisting of A, T, G and C, to discriminate the base sequence of 1 to 4 bases contiguous to the base sequence recognized by the first restriction enzyme of the one strand of the specific double stranded DNA fragment, and, in the second anchor primer, the part of bases of the second base sequence is replaced with another base species not to be digested with the first restriction enzyme, and wherein the second anchor primer has, at a side of a 5' end thereof, a second anchor base sequence which has a known base sequence having at least 8 bases and does not hybridize with one strand of the double stranded sample DNA, a fourth base sequence which is connected to a 3' end of the second anchor base sequence and is complementary to the base sequence of the oligonucleotide, a fifth base sequence which has the same base sequence as base sequence complementary to the base sequence recognized by the second restriction enzyme except for a part of bases in the recognition base sequence recognized by the second restriction enzyme, and is connected to at a 3' end of the fourth base sequence, and has, at a 3' end, a sixth base sequence which has a second arbitrary base sequence of 1 to 4 bases selected from the group consisting of A, T, G and C, to discriminate the base sequence of 1 to 4 bases contiguous to the base sequence recognized by the first restriction enzyme of the one strand of the specific double stranded DNA fragment, and, in the second anchor primer, the part of bases of the fifth base sequence is replaced with another base species not to be digested with the second restriction enzyme;

(4) digesting the first end of the amplified specific double DNA fragment with the second restriction enzyme and digesting the second end of the amplified specific double stranded DNA fragment with the first restriction enzyme to form a first DNA strand and a second DNA strand, respectively;

(5) performing a complementary strand extension synthesis using the first DNA strand and the second DNA strand formed in step (4) as templates, and using a first fluorophore tagged primer and a second fluorophore tagged primer, to form a first extended DNA fragment and a second extended DNA fragment by the complementary strand extension synthesis, respectively, wherein the first fluorophore tagged primer has substantially the same base sequence as the first anchor base sequence that does not hybridize with the one strand of the double stranded of sample DNA, and wherein the second fluorophore tagged primer has substantially the same base sequence as the second anchor base sequence that does not hybridize with the one strand of the double stranded of sample DNA; and (6) performing a sequencing reaction using the first DNA strand and the second DNA strand formed in step (4) and each strand of the double stranded sample DNA as templates, and using the first fluorophore tagged primer, the second fluorophore tagged primer, the first extended DNA fragment and the second extended DNA fragment formed by the complementary strand extension reaction in step (5), whereby the base sequences of the first DNA strand and the second DNA strand and base sequences of the each of stranded of the double stranded sample DNA in a portion contiguous to the first DNA strand and second DNA strand are determined.

38. A primer set comprising:

a first anchor primer set; and a second anchor primer set, wherein each primer of the first anchor primer set has, at a side of a 5' end thereof, a first anchor base sequence which has a known base sequence having at least 8 bases and does not hybridize with one strand of a double stranded sample DNA, a first base sequence which is connected to a 3' end of the first anchor base sequence and is complementary to a base sequence of a oligonucleotide has a known base sequence and a recognition base sequence recognized by a second recognition restriction enzyme, and which is connected to double stranded DNA fragments formed by digesting the double stranded sample DNA with a first restriction enzyme, a second base sequence which has the same base sequence as a base sequence complementary to the base sequence recognized by the first restriction enzyme except for a part of bases in the recognition base sequence recognized by the first restriction enzyme, and is connected to at a 3' end of the first base sequence, and has, at a 3' end, a third base sequence which has two bases selected from the group consisting of A, T, G and C, to discriminate a base sequence of two bases contiguous to the base sequence recognized by the first restriction enzyme of one strand of a specific double stranded DNA fragment, and, in the first anchor primer, the part of bases of the second base sequence is replaced with another base species not to be digested with the first restriction enzyme, wherein the third base sequence has all possible sixteen combinations of two bases out of A, C, G and T, wherein each primer of a second anchor primer set has, at side of a 5' end thereof, a second anchor base sequence which has a known base sequence having at least 8 bases and does not hybridize with one strand of the double stranded sample DNA, a fourth base sequence which is connected to a 3' end of the second anchor base sequence and is complementary to the base sequence of the oligonucleotide, a fifth base sequence which has the same base sequence as a base sequence complementary to the base sequence recognized by the second restriction enzyme except for a part of bases in the recognition base sequence recognized by the second restriction enzyme, and is connected to at a 3' end of the fourth base sequence, and has, at a 3' end, a sixth base sequence which has two bases selected from the group consisting of A, T, G and C, to discriminate a base sequence of two bases contiguous to the base sequence recognized by the first restriction enzyme of the one strand of the specific double stranded DNA fragments, and, in the second anchor primer, the part of bases of the fifth base sequence is replaced with another base species not to be digested with the second restriction enzyme, wherein the sixth base sequence has all possible sixteen combinations of two bases out of A, C, G and T, and wherein the specific double stranded DNA fragment is amplified by PCR, using the primer of the first anchor primer set and the primer of the second anchor primer set.

39. A DNA sequencing method comprising:

(1) digesting a sample DNA with a restriction enzyme to obtain DNA fragments;

(2) connecting an oligonucleotide having a known sequence to the DNA fragments at 3' termini thereof;

(3) performing a complementary strand extension reaction of a labeled primer having a base sequence complementary to the oligonucleotide connected to the DNA fragments and a selective base sequence of 1 to 4 bases selected from the group consisting of A, T, G and C, at a 3' terminus, to discriminate a base sequence of 1 to 4 bases of the DNA fragments, by using the DNA fragment obtained in step (2) as a template for the complementary strand extension reaction to produce a labeled extended primer;

(4) performing a sequencing reaction using the labeled primer, the labeled extended primer, and the DNA fragment obtained in step (2) together with the sample DNA; and (5) subjecting the sequencing reaction products obtained in step (4) to electrophoresis for size separation to determine a base sequence of the DNA fragment and a base sequence of the sample DNA contiguous to a base of a 3' terminus of the DNA fragment.

40. A DNA sequencing method according to claim 39, wherein the sequencing reaction in step (4) is carried out using the labeled extended primer and the sample DNA to sequence just adjacent sequence of a cutting site of the restriction enzyme.

41. A DNA sequencing method according to claim 39, wherein said labeled primer is labeled with a fluorophore.

42. A DNA sequencing method according to claim 39, wherein said step (3) is repeated a plurality of times by varying temperature conditions.

43. A DNA sequencing method according to claim 39, wherein said step (3) is repeated a plurality of times in a thermal cycle to amplify the labeled extended primer.

44. A DNA sequencing method according to claim 39, wherein the DNA polymerase used in steps (3) and (4) is a thermostable DNA polymerase.

45. A method for preparing a sequencing primer used in a DNA sequencing comprising:

(1) digesting a sample DNA with a first restriction enzyme to obtain DNA fragments;

(2) connecting an oligonucleotide having a known base sequence to the DNA fragments at $_3$' termini thereof;

(3) performing a complementary strand extension reaction of a primer using the DNA fragment obtained in step (2) as a template to form a extended primer, and then decomposing the extended primer from a 3' terminus side and connecting a fluorophore tagged nucleotide at a 3' terminus of the decomposed extended primer; and (4) digesting the double stranded DNA fragment formed in step (3) with a second restriction enzyme to produce a fluorophore labeled sequencing primer, wherein said fluorophore labeled sequencing primer can hybridize to the sample DNA, and can be extended by a complementary strand extension reaction using a base sequence adjacent to a cutting site of the first restriction enzyme as a template.

46. A DNA sequencing method comprising:
(1) digesting a sample DNA with a first restriction enzyme to obtain DNA fragments;
(2) connecting an oligonucleotide having a known base sequence to the DNA fragments at 3' termini thereof;
(3) performing a complementary strand extension reaction of a primer using the DNA fragment obtained in step (2) as a template to form a extended primer, and then decomposing the extended primer from a 3' terminus side and connecting a fluorophore tagged nucleotide at a 3' terminus of the decomposed extended primer;
(4) digesting the double stranded DNA fragment formed in step (3) with a second restriction enzyme to produce a fluorophore labeled sequencing primer, wherein said fluorophore labeled sequencing primer can hybridize to the sample DNA, and can be extended by a complementary strand extension reaction using a base sequence adjacent to a cutting site of the first restriction enzyme as a template; and
(5) performing a sequencing reaction using said fluorophore labeled sequencing primer produced in step (4), and using the sample DNA as template.

47. A DNA sequencing method comprising:
(1) digesting a sample DNA with a restriction enzyme to obtain DNA fragments;
(2) performing a complementary strand extension reaction of a primer using the DNA fragment as a template to form a extended primer;
(3) performing a sequencing reaction using said extended primer produced in step (2) and dideoxynucleotides (ddNTP) tagged with a fluorophore, and using the sample DNA as template; and
(4) digesting the double stranded DNA fragment formed in step (3) with the restriction enzyme to produce shortened sequencing reaction products for gel electrophoresis to determine a base sequence at least adjacent to a cutting site of the restriction enzyme.

48. A DNA sequencing method comprising;
(1) digesting a sample DNA with a restriction enzyme to form DNA fragments;
(2) performing a complementary strand synthesis using the DNA fragments as a template, and using deoxynucleotides (dNTP), a fluorophore tagged primer and a DNA polymerase to form a extended fluorophore tagged primer having a base sequence complementary to the DNA fragments;
(3) performing a sequencing reaction using the sample DNA as a template, and using the extended fluorophore tagged primer formed in step (2), the DNA polymerase, deoxynucleotides (dNTP), and dideoxynucleotides (ddNTP) as sequencing reagents; and
(4) subjecting products of the sequencing reaction in step (3) to electrophoresis to determine at least a part of the base sequence of the sample DNA contiguous to a 3' end of the base sequence of the DNA fragments.

49. A method for preparing sequencing reaction products used for DNA sequencing comprising:

(1) producing, from a sample DNA, DNA fragments having a sequence including a priming sequence which does not exist in a sequence of the sample DNA and including a part of the sequence of the sample DNA; and,
(2) performing a sequencing reaction using a first primer having a base sequence complementary to the priming sequence and being labeled with a fluorophore, a second primer having a base sequence complementary to the DNA fragment and being labeled with a fluorophore, and using the DNA fragments and the sample DNA as templates, to sequence reaction products of the sequencing reaction and to determine a base sequence of the DNA fragment and a base sequence of the sample DNA contiguous to a base of a 3' terminus of the DNA fragment.

50. A DNA sequencing method comprising:
(1) digesting a sample DNA to obtain DNA fragments; and
(2) performing a sequencing reaction to obtain sequencing reaction products each of which is labeled with a fluorophore, using a primer which hybridizes with the DNA fragments, deoxynucleotides (dNTP), dideoxynucleotides (ddNTP) as sequencing reagents, and wherein the DNA fragments and the sample DNA before digestion are used as templates.

51. A method for preparing a sample which comprises:
(1) digesting a sample DNA with a restriction enzyme to obtain DNA fragments;
(2) connecting an oligonucleotide having a known base sequence to the DNA fragments at 3' termini thereof;
(3) performing synthesis of DNA strand complementary to DNA fragments produced in step (2) using an anchor primer comprising a constant base sequence complementary to the oligonucleotide, a selective base sequence of 1 to 4 bases selected from the group consisting of A, T, G and C, at a 3' terminus, to discriminate a base sequence of 1 to 4 bases of the DNA fragments, and an anchor base sequence which has a known base sequence having at least 8 bases at a 5' terminal and does not hybridize with the DNA fragments obtained in step (1), and
(4) performing complementary strand synthesis and a copy strand synthesis of the DNA strand obtained in step (3), using the DNA strand obtained in step (3) as a template, and then using a fluorophore tagged primer having the same sequence as the anchor sequence which does not hybridize with the DNA fragments obtained in step (1) and the DNA fragments obtained in step (2), to form a fluorophore tagged extended primer which hybridizes with the sample DNA.

52. A method for preparing sample which comprises:
(1) digesting a sample DNA with a restriction enzyme to form DNA fragments;
(2) connecting an oligonucleotide having a known base sequence to the DNA fragments at 3' termini thereof; and
(3) fractionating the DNA fragments obtained in step (2) depending upon their base sequence of 1 to 4 bases adjacent to a recognition sequence of the restriction enzyme and amplifying the DNA fragments obtained in step (2), by PCR, using anchor primers having a complementary sequence to a base sequence of the oligonucleotide and a base sequence of 1 to 4 bases comprising A, C, G and T at a 3' terminus to amplify selectively the DNA fragments obtained in step (2) and having an anchor base sequence which has a known base sequence at least 8 bases at a 5' terminal and does not hybridize with the DNA fragments obtained in step (1) and the DNA fragments obtained in step (2).

53. A method for preparing sample which comprises:
(1) digesting a sample DNA with a restriction enzymes to produce DNA fragments,
(2) connecting an oligonucleotide having a known base sequence to both ends of the fragments; and
(3) performing complementary strand synthesis of the fragments obtained in step (2) using a first primer and a second primer,
wherein each of the first and second primer has a selective base sequence part of 1 to 4 bases selected from the group consisting of A, T, G and C, at a 3' terminus, to discriminate the DNA fragments and a common base sequence being included in a recognition sequence site by the restriction enzyme and being identical for the first and second primer, and
wherein at least one nucleotide in the common sequence of the first primer is replaced with another nucleotide species different from a species of the one nucleotide to form a DNA strand which cannot be digested by the restriction enzyme at one side thereof, and which can be digested with the restriction enzyme at at another side thereof, to form a sequencing template having one priming site.

54. A method for preparing a sample according to claim 53,
wherein one terminus of the DNA strand is digested with the restriction enzyme to prepare the sequencing template DNA for determining a base sequence of the sample DNA.

55. A DNA sequencing method comprising:
(1) digesting a sample DNA with a restriction enzyme to form DNA fragments having a plurality of fragment lengths;
(2) connecting an oligonucleotide having a known base sequence to the DNA fragments at a 3' end thereof;
(3) amplifying the DNA fragments obtained in step (2), by PCR using an anchor primer and a primer,
wherein the anchor primer has, at side of a 5' end thereof, an anchor base sequence which has a known base sequence having at least 8 bases and does not hybridize with one strand of the sample DNA, a first common base sequence which is connected to a 3' end of the anchor base sequence and is complementary to the base sequence of the oligonucleotide, a second common base sequence which has the same base sequence as base sequence complementary to the base sequence recognized by the restriction enzyme except for a part of bases in the recognition base sequence recognized by the restriction enzyme, and is connected to at a 3' end of the first common base sequence, and has, at a 3' end, a selective base sequence of 1 to 4 bases selected from the group consisting of A, T, G and C, to discriminate fragments being amplified in PCR, and
wherein the primer has a base sequence to be digested with the restriction enzyme, and
wherein, in the anchor primer, the part of bases of the second common base sequence is replaced with another base species not to be digested by the restriction enzyme;
(4) obtaining a DNA strand in which one terminus of the amplified DNA fragment obtained in step (3) has been digested enzymatically;
(5) producing a fluorophore tagged extended primer by performing a complementary strand extension reaction of a fluorophore tagged primer having the same sequence as the anchor base sequence that does not hybridize with the sample DNA but hybridizes with the DNA fragments produced in step (4) by using the DNA fragments produced in step (4) as a template; and
(6) performing a sequencing reaction using the fluorophore tagged primer and the extended fluorophore tagged primer produced in step (5) by using the DNA fragment obtained in step (4)and the sample DNA as templates.

56. A DNA sequencing method comprising:
(1) digesting a sample DNA with a restriction enzyme to form DNA fragments having a plurality of fragment lengths;
(2) connecting an oligonucleotide having a known base sequence to the DNA fragments at least at 3' termini thereof; and
(3) amplifying a specific DNA fragment in DNA fragments obtained in step (2), by PCR, using an anchor primer having a complementary sequence to a base sequence of the oligonucleotide and a recognition sequence of the restriction enzyme, a selective base sequence of 1 to 4 bases selected from the group consisting of A, T, G and C, at a 3' terminus, and an anchor base sequence which has a known base sequence having at least 8 bases at a 5' terminus and does not hybridize with the DNA fragments obtained in step (1), and using a primer having a base sequence to be digested with the restriction enzyme,
wherein, in the anchor primer, a part of bases in the base sequence complementary to the recognition sequence has been replaced with another base species not to be digested with the restriction enzyme.

57. A DNA sequencing method comprising:
(1) digesting a sample DNA with a first restriction enzyme to form DNA fragments having a plurality of fragment lengths;
(2) connecting an oligonucleotide having a known base sequence and having a recognition base sequence of a second restriction enzyme to the DNA fragments at a 3' terminus thereof;
(3) amplifying DNA fragment obtained in step (2), by PCR using a first anchor primer and a second anchor primer,
wherein the first anchor primer has a base sequence complementary to a base sequence of the oligonucleotide and a first recognition sequence by the first restriction enzyme, a first selective sequence of 1 to 4 bases selected from the group consisting of A, T, G and C, at a 3' terminus, and a first anchor base sequence which has a known base sequence having at least 8 bases and does not hybridize with the DNA fragments obtained in step (1), at a 5' terminus,
wherein a complementary sequence of the first anchor base sequence is used as a priming sequence,
wherein, in the first anchor primer, a part of bases in the base sequence complementary to the first recognition sequence has been replaced with another base species not to be digested with the first restriction enzyme,
wherein the second anchor primer has a base sequence complementary to a base sequence of the oligonucleotide and a second recognition sequence by the second restriction enzyme, and a second selective base sequence of 1 to 4 bases selected from the group consisting of A, T, G and C, at a 3' terminus, and a second anchor base sequence which has a known base sequence having at least 8 bases different from the first anchor sequence and does not hybridize with the DNA fragments obtained in step (1), at a 5' terminus, and wherein, in the second anchor primer, a part of bases in the base sequence complementary to the second recognition sequence has been replaced with another base species not to be digested with the second restriction enzyme;

(4) dividing the PCR product in step (3) at least into two fractions, and digesting a first terminus of the amplified DNA fragment in a first fraction with the second restriction enzyme, and digesting a second terminus of the amplified DNA fragments in a second fraction with the first restriction enzyme to obtain a first and second DNA strands, respectively;

(5) performing a complementary strand extension reactions using a first fluorophore tagged primer having a base sequence including the same base sequence as the first anchor base sequence, and using a second fluorophore tagged primer having a base sequence including the same base sequence as the second anchor base sequence, and using the DNA fragments produced in step (4) as templates to obtain a first and second extended DNA fragments by the complementary strand extension reaction, respectively; and (6) performing a sequencing reaction using the first and second fluorophore tagged primers, the extended first and second fluorophore tagged primers, and using the first and second DNA strands obtained in step (4) and the sample DNA as templates.

58. A DNA sequencing method according to claim 57, wherein said first fluorophore tagged primer contains the same base sequence as the first anchor base sequence, and said second fluorophore tagged primer contains the same sequence as the second anchor base sequence.

59. A DNA sequencing method comprising:

(1) digesting a sample DNA with a first restriction enzyme to form DNA fragments having a plurality of fragment lengths;

(2) connecting an oligonucleotide having a known base sequence and having a recognition base sequence of a second restriction enzyme to the DNA fragments at a 3' terminus thereof;

(3) amplifying DNA fragment obtained in step (2), by PCR using a first anchor primer and a second anchor primer, wherein the first anchor primer has a base sequence complementary to a base sequence of the oligonucleotide and a first recognition sequence by the first restriction enzyme, a first selective sequence of 1 to 4 bases selected from the group consisting of A, T, G and C, at a 3' terminus, and a first anchor base sequence which has a known base sequence having at least 8 bases and does not hybridize the DNA fragments obtained in step (1), at a 5' terminus, wherein a complementary sequence of the first anchor base sequence is used as a priming sequence, wherein, in the first anchor primer, a part of bases in the base sequence complementary to the first recognition sequence has been replaced with another base species not to be digested with the first restriction enzyme, wherein the second anchor primer has a base sequence complementary to a base sequence of the oligonucleotide and a second recognition sequence by the second restriction enzyme, and a second selective base sequence of 1 to 4 bases selected from the group consisting of A, T, G and C, at a 3' terminus, and a second anchor base sequence which has a known base sequence having at least 8 bases different from the first anchor sequence and does not hybridize with the DNA fragments obtained in step (1), at a 5' terminus, and wherein, in the second anchor primer a part of bases in the base sequence complementary to the second recognition sequence in the second anchor primer has been replaced with another base species not to be digested with the second restriction enzyme;

(4) dividing the PCR product in step (3) at least into two fractions, and digesting a first terminus of the amplified DNA fragment in a first fraction with the second restriction enzyme, and digesting a second terminus of the amplified DNA fragments in a second fraction with the first restriction enzyme to obtain a first and second DNA strands, respectively;

(5) performing a sequencing reaction using a first fluorophore tagged primer, a second fluorophore tagged primer, an extended first fluorophore tagged primer formed by performing a complementary strand synthesis of the first fluorophore tagged primer using the first DNA strand as a template, and an extended second fluorophore tagged primer formed by performing a complementary strand synthesis of the second fluorophore tagged primer using the second DNA strand as a template, and using the first and second DNA strands obtained in step (4) and the sample DNA as templates, to determine a base sequences of the first and second DNA strands and a base sequences of the sample DNA adjacent to the base sequences of the first and second DNA strands.

60. A DNA sequencing method according to claim 59, wherein said first fluorophore tagged primer contains the same base sequence as the first anchor base sequence, and said second fluorophore tagged primer contains the same sequence as the second anchor base sequence.

61. A DNA sequencing method comprising:

(1) digesting a sample DNA with a first restriction enzyme to form DNA fragments having a plurality of fragment lengths;

(2) connecting an oligonucleotide having a known base sequence and having a recognition base sequence of a second restriction enzyme to the DNA fragments at a 3' terminus thereof;

(3) amplifying the DNA fragment obtained in step (2), by PCR using a first anchor primer and a second anchor primer, thereby to determine the base sequence of the DNA fragments amplified, wherein the first anchor primer has a base sequence complementary to a base sequence of the oligonucleotide and a first recognition sequence by the first restriction enzyme, a first selective sequence of 1 to 4 bases selected from the group consisting of A, T, G and C, at a 3' terminus, and a first anchor base sequence which has a known base sequence having at least 8 bases and does not hybridize with the DNA fragments obtained in step (1), at a 5' terminus, wherein the first anchor base sequence cannot hybridize the DNA fragments, and a complementary sequence of the first anchor base sequence is used as a priming sequence, wherein, in the first anchor primer, a part of bases in the base sequence complementary to the first recognition sequence has been replaced with another base species not to be digested with the first restriction enzyme, wherein the second anchor primer has a base sequence complementary to a base sequence of the oligonucleotide and a second recognition sequence by the second restriction enzyme, and a second selective base sequence of 1 to 4 bases selected from the group consisting of A, T, G and C, at a 3' terminus, and a second anchor base sequence which has a known base sequence having at least 8 bases different from the first anchor sequence and does not hybridize with the DNA fragments obtained in step (1), at a 5' terminus, and wherein, in the second anchor primer, a part of bases in the base sequence complementary to the second recognition sequence in the second anchor primer has been replaced with another base species not to be digested with the second restriction enzyme.

62. A reagent kit comprising:
a plurality of anchor primers each having a base sequence complementary to an oligonucleotide connected to DNA fragments obtained by enzymatic digestion from a sample DNA, a selective base sequence of 1 to 4 bases selected from the group consisting of A, T, G and C, at 3' termini thereof, to discriminate the DNA fragments to be duplicated by polymerase chain reaction (PCR), and an anchor base sequence which has a known base sequence having at least 8 bases and does not hybridize with the DNA fragments, at a 5' terminus, wherein primers for sequencing duplicated DNA fragments connected with the oligonucleotide are obtained using the plurality of anchor primers.

63. A reagent kit according to claim 62, wherein said anchor primers contain selective base sequences of two bases selected from the group consisting of A, T, G and C, to discriminate the DNA fragments to be duplicated by DNA polymerase chain reaction (PCR),
wherein the reagent kit includes said anchor primers having the selective base sequences including all possible combinations of the two bases selected from the group consisting of A, T, G and C.

64. A reagent kit comprising:
a first primer set comprising 16 primers having a complementary sequence to an oligonucleotide connected to DNA fragments produced by a digestion by a restriction enzyme and a complementary sequence to a recognition base sequence recognized by the restriction enzyme, and a selective base sequence of two bases selected from the group consisting of A, T, G and C, at a 3' terminus of the recognition base sequence to discriminate the DNA fragments; and
a second primer set comprising 16 primers having an anchor base sequence connected to a 5' terminus of each primer in the first primer set,
wherein, in the primers of the first primer set, a part of the bases in the base sequence complementary to the recognition base sequence has been replaced with another base species wherein the DNA fragments are amplified by PCR, using the primer of the first primer set and the primer of the second primer set.

65. A reagent kit comprising:
a first anchor primer set; and
a second anchor primer set,
wherein each primer of the first anchor primer set has a base sequence complementary to an oligonucleotide connected to DNA fragments digested by a first restriction enzyme and a recognition base sequence recognized by the first restriction enzyme, a first selective base sequence of 1 to 4 bases selected from the group consisting of A, T, G and C, at a 3' terminus, to discriminate the DNA fragments, and a first anchor base sequence which has a known base sequence having at least 8 bases at a 5' terminus and does not hybridize with the DNA fragments, and, in the primers of the first anchor primer set, a part of bases in the base sequence complementary to the recognition base sequence has been replaced with another base species to have a base sequence not to be digested with the first restriction enzyme,
wherein the first selective base sequence has all possible 4 to $4^4$ combinations of 1 to 4 bases out of A, C, G and T, wherein each primer of the second anchor primer set has a base sequence complementary to the oligonucleotide and the recognition base sequence, a second selective base sequence of 1 to 4 bases selected from the group consisting of A, T, G and C, at a 3' terminus, to discriminate the DNA fragments, and a second anchor base sequence which has a known base sequence having at least 8 bases at a 5' terminus and does not hybridize with the DNA fragments, and, in the primers of the second anchor primer set, a part of bases in the base sequence complementary to the oligonucleotide has been replaced with another base species to have a base sequence not to be digested with a second restriction enzyme,
wherein the second selective base sequence has all possible $4^1$ to $4^4$ combinations of 1 to 4 bases out of A, C, G and T, and
wherein the DNA fragments are amplified by PCR, using the primer of the first anchor primer set and the primer of the second anchor primer set.

66. A reagent kit according to claim 65, wherein said first and second selective base sequence comprise two bases and include all combination of two base sequences.

67. A method of DNA sequencing analysis which comprises;
(1) digesting a sample DNA with a restriction enzyme to obtain a DNA fragments;
(2) connecting an oligonucleotide having known base sequence to the DNA fragments at a 3' terminus thereof;
(3) performing synthesis of DNA strand complementary to DNA fragments produced in step (2) using an anchor primer comprising a constant base sequence complementary to the oligonucleotide, a selective base sequence of 1 to 4 bases selected from the group consisting of A, T, G and C, at a 3' terminus, to discriminate a base sequence of 1 to 4 bases of the DNA fragments, and an anchor base sequence which has a known base sequence having at least 8 bases at a 5' terminal and does not hybridize with the DNA fragments obtained in step (1), and
(4) performing complementary strand synthesis and a copy strand synthesis of the DNA strand obtained in step (3), using the DNA strand obtained in step (3) as a template, and using a fluorophore tagged primer having the same sequence as the anchor sequence which does not hybridize with the DNA fragments obtained in step (1) and DNA fragments obtained in step (2), to form a fluorophore tagged extended primer which hybridizes with the sample DNA.

68. A method for DNA sequencing analysis which comprises:
(1) digesting a sample DNA with a restriction enzyme to obtain DNA fragments having a plurality of fragment lengths;
(2) connecting an oligonucleotide having a known base sequence to the DNA fragments at least at 3' termini thereof; and
(3) fractionating DNA fragments obtained in step (2) depending upon their base sequence of 1 to 4 bases adjacent to a recognition sequence of the restriction enzyme and amplifying the DNA fragments obtained in step (2), by PCR, using anchor primers having a complementary sequence to the oligonucleotide and a base sequence of 1 to 4 bases comprising A, C, G and T at a 3' terminus,
wherein said PCR amplifies selectively the DNA fragments obtained in step (2) and said anchor primers have an anchor base sequence that does not hybridize with the DNA fragments obtained in step (2).

69. A method for sequencing DNA fragments comprises;
(1) digesting a sample DNA with a restriction enzyme to produce DNA fragments,
(2) connecting oligonucleotides to cutting sites by the restriction enzyme of the DNA fragments; and
(3) performing complementary strand synthesis of the DNA fragments produced in step (2) using a first primer and a second primer, wherein each of the first and second primers has a selective base sequence of 1 to 4 bases selected from the group consisting of A, T, G and C, at a 3' terminus, to discriminate DNA fragments obtained in step (2), and a common base sequence being included in a recognition sequence site by the restriction enzyme and being identical for the first primer and second primer, and wherein at least one nucleotide in the common sequence of the first primer is replaced another nucleotide species different from a species of the one nucleotide to form a DNA strand which cannot be digested by the restriction enzyme at one side thereof, and which can be digested with the restriction enzyme at another side thereof, to form a sequencing template having one priming site.

* * * * *